US008110093B2

(12) United States Patent
Friedman et al.

(10) Patent No.: US 8,110,093 B2
(45) Date of Patent: Feb. 7, 2012

(54) PROCESS FOR PRODUCING LOW MOLECULAR WEIGHT HYDROCARBONS FROM RENEWABLE RESOURCES

(75) Inventors: Lisa Friedman, So. San Francisco, CA (US); Mathew Rude, So. San Francisco, CA (US)

(73) Assignee: LS9, Inc., South San Francisco, CA (US)

( * ) Notice: Subject to any disclaimer, the term of this patent is extended or adjusted under 35 U.S.C. 154(b) by 0 days.

(21) Appl. No.: 12/278,961

(22) PCT Filed: Mar. 14, 2008

(86) PCT No.: PCT/US2008/057127
§ 371 (c)(1),
(2), (4) Date: Aug. 8, 2008

(87) PCT Pub. No.: WO2008/113041
PCT Pub. Date: Sep. 18, 2008

(65) Prior Publication Data
US 2010/0170826 A1 Jul. 8, 2010

Related U.S. Application Data

(60) Provisional application No. 60/894,907, filed on Mar. 14, 2007, provisional application No. 60/908,547, filed on Mar. 28, 2007, provisional application No. 60/931,370, filed on May 22, 2007, provisional application No. 60/931,939, filed on May 25, 2007, provisional application No. 60/951,944, filed on Jul. 25, 2007, provisional application No. 60/974,810, filed on Sep. 24, 2007.

(51) Int. Cl.
*C12P 5/00* (2006.01)
*C10G 11/00* (2006.01)

(52) U.S. Cl. ................... 208/118; 208/120.01; 435/166; 435/167; 585/16

(58) Field of Classification Search .................. 208/106, 208/118, 120.01; 435/166, 167
See application file for complete search history.

(56) References Cited

U.S. PATENT DOCUMENTS

| | | | | |
|---|---|---|---|---|
| 5,233,109 A | 8/1993 | Chow | | |
| 7,691,159 B2 * | 4/2010 | Li | 44/605 | |
| 2007/0192900 A1 * | 8/2007 | Sticklen | 800/280 | |
| 2009/0215140 A1 * | 8/2009 | Kurano et al. | 435/166 | |
| 2010/0185017 A1 * | 7/2010 | Yoshikuni et al. | 568/448 | |

FOREIGN PATENT DOCUMENTS

DE 10-2004-052115 A1 4/2006

OTHER PUBLICATIONS

Benson, et al., "Development of a Heterogeneous Catalytic Cracking Reactor Utilizing Online Mass Spectrometry Analysis", J.Chromatography, vol. 1172(2): 204-208 (2007).

(Continued)

*Primary Examiner* — Ellen McAvoy
(74) *Attorney, Agent, or Firm* — Linda R. Judge; LS9, Inc.

(57) ABSTRACT

Described herein are methods for cracking a biocrude, particularly catalytically cracking a biocrude that primarily includes olefinic hydrocarbons. Also described herein are compositions and methods of producing such compositions that are useful as fuels or fuel production feedstock.

27 Claims, 27 Drawing Sheets

OTHER PUBLICATIONS

James, E.S. et al., "Expression of Two *Escherichia coli* Acetyl-CoA Carboxylase Subunits is Autoregulated", J. Biol. Chem., vol. 279(4): 2520-2527 (2004).

Kalscheuer, R. et al., "Neutral Lipid Biosynthesis in Engineered *Escherichia coli*: Jojoba Oil-Like Wax Esters and Fatty Acid Butyl Esters", Applied & Environmental Microbiology, vol. 72(2): 1373-1379 (2006).

Kalscheuer, R. et al., "Microdiesel: *Escherichia coli* Engineered for Fuel Production", Microbiology, vol. 152(9): 2529-2536 (2006).

Kalscheuer, R. et al., "A Novel Bifunctional Wax Ester Synthase/Acyl-CoA:Diacylglycerol Acyltransferase Mediates Wax Ester & Triacylglycerol Biosynthesis in Acinetobacter calcoaceticus ADP1", J. Biol. Chem., vol. 278(10): 8075-8082 (2003).

Lardizabal, K.D. et al., "Purification of a Jojoba Embryo Wax Synthase, Cloning of its cDNA, & Production of High Levels of Wax in Seeds of Transgenic *Arabidopsis*", Plant Physiology, vol. 122(3): 645-655 (2000).

Twaig, Farouq A.A. et al., "Performance of Composite Catalysts in Palm Oil Cracking for the Production of Liquid Fuels and Chemicals", Fuel Processing Technology, vol. 85: 1283-1300 (2004).

Wu, X-Y. et al., "Studies of Biosynthesis of Waxes by Developing Jojoba *Simmondsia-Chinensis* Seed III. Biosynthesis of Wax Esters from Acyl Coenzyme A and Long Chain Alcohols", Lipids, vol. 16(12): 897-902 (1981).

International Search Report and Written Opinion from PCT/US2007/011923, mailed Feb. 22, 2008.

International Search Report and Written Opinion from PCT/US2008/057127, mailed Sep. 5, 2008.

* cited by examiner

FIGS. 4A-J
FIG. 4A C27 triene
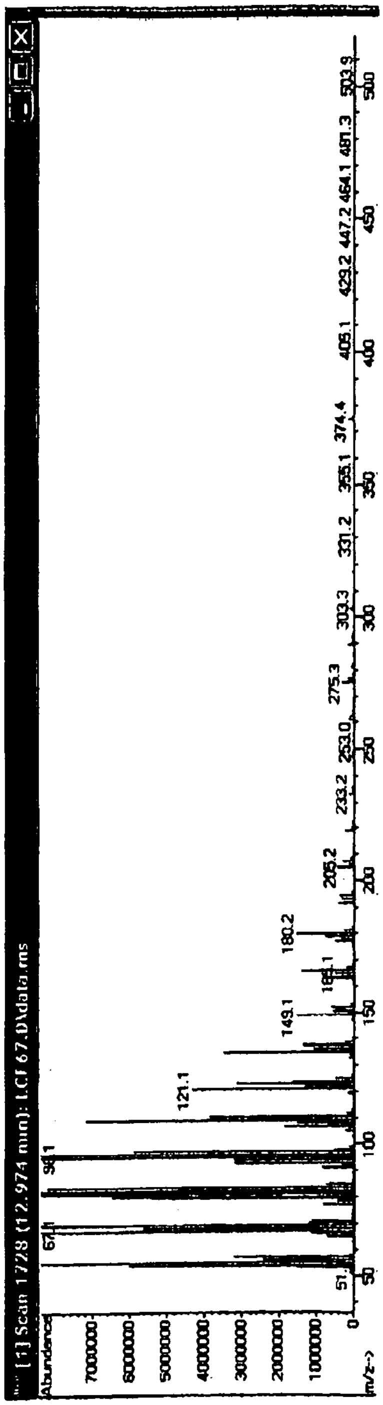
FIG. 4B C27 diene
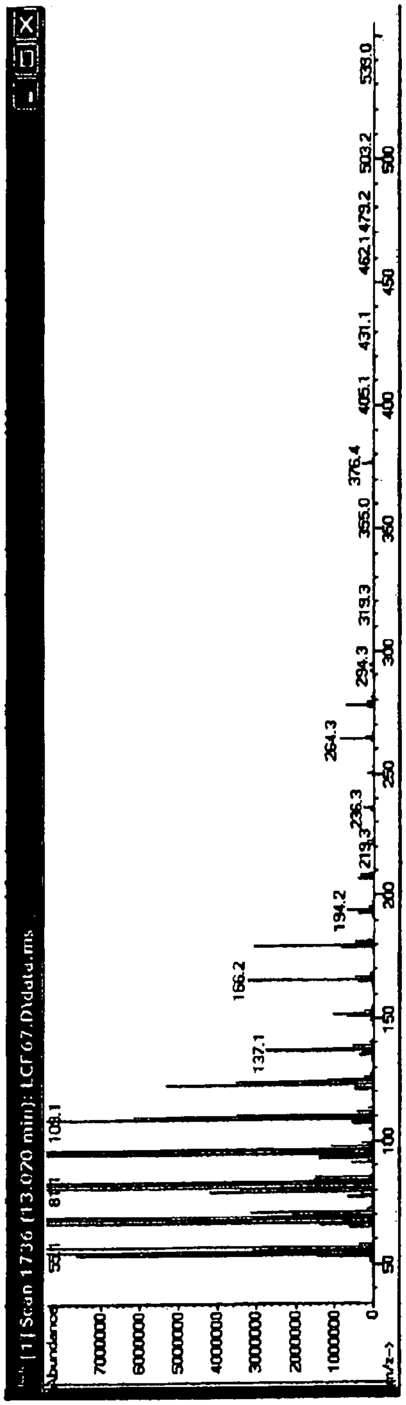

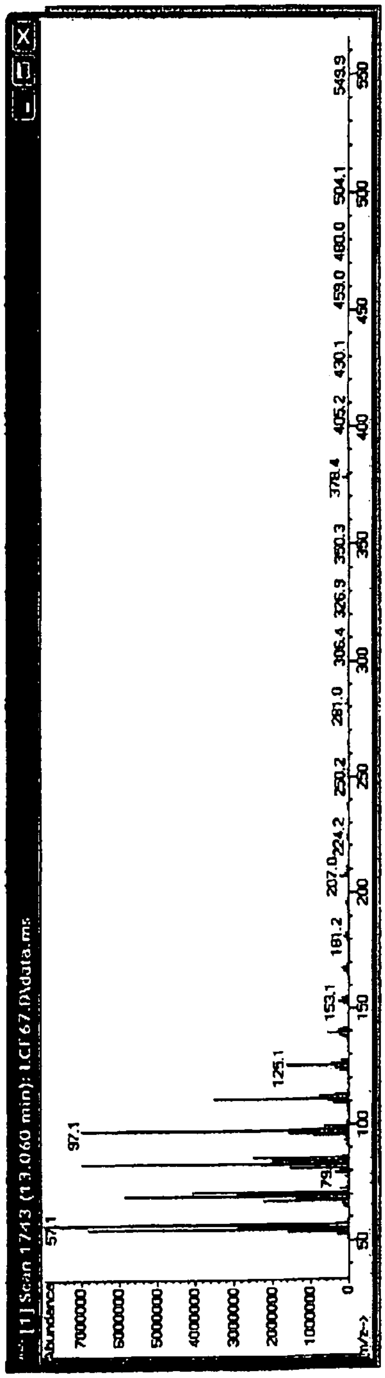
FIG. 4C C27 monoene
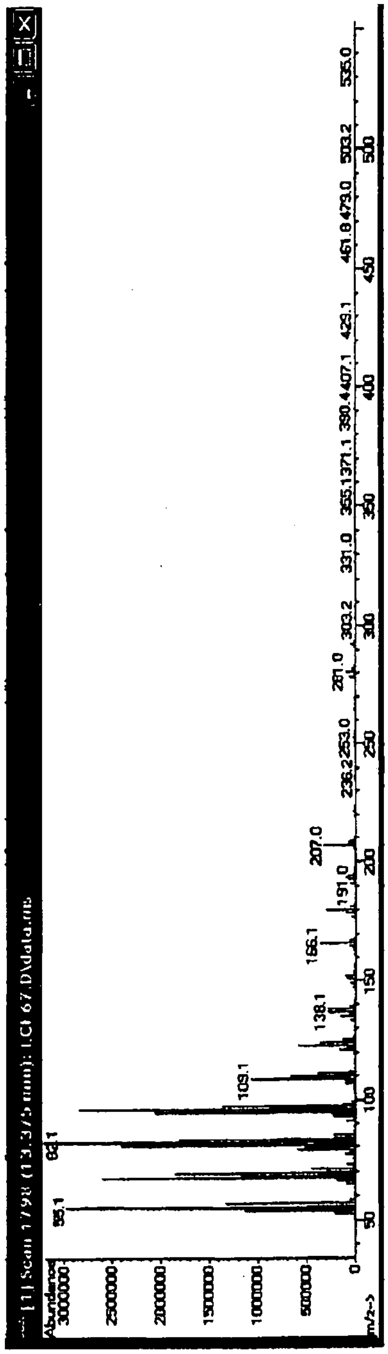
FIG. 4D C28 diene

FIG. 4E C29 triene
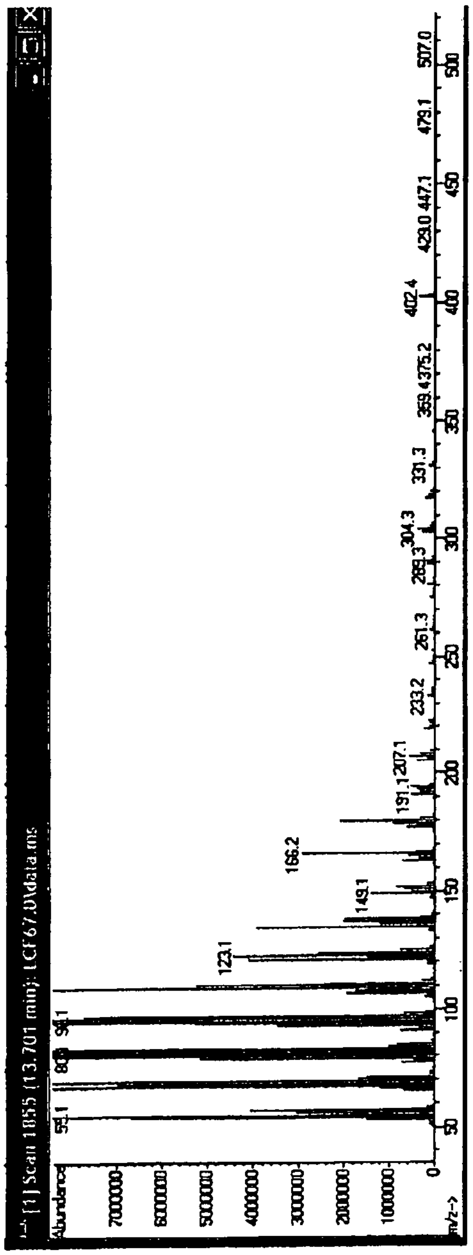
FIG. 4F C29 diene
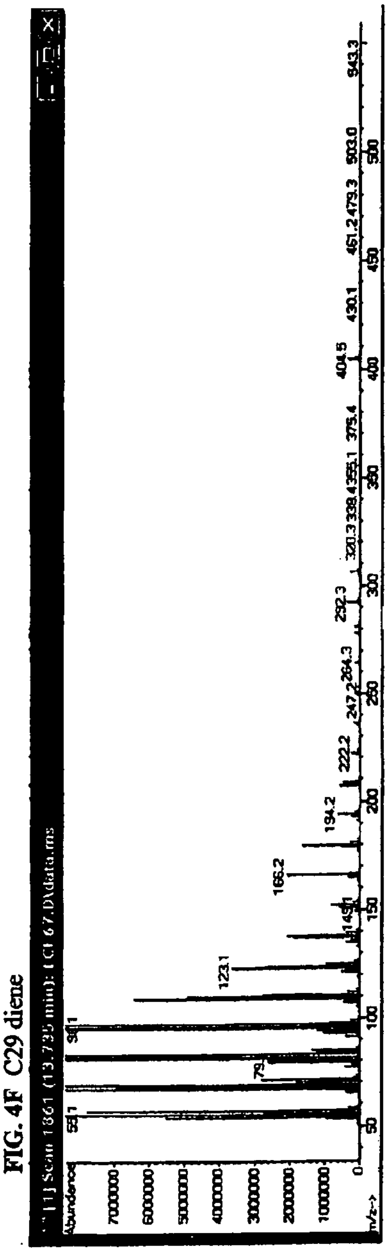

FIG. 4G C29 monoene
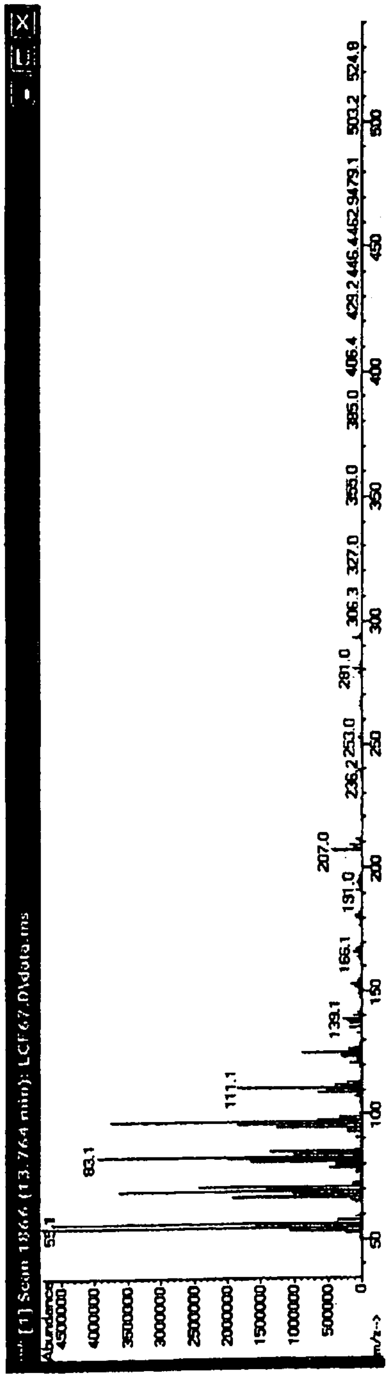
FIG. 4H C30 diene
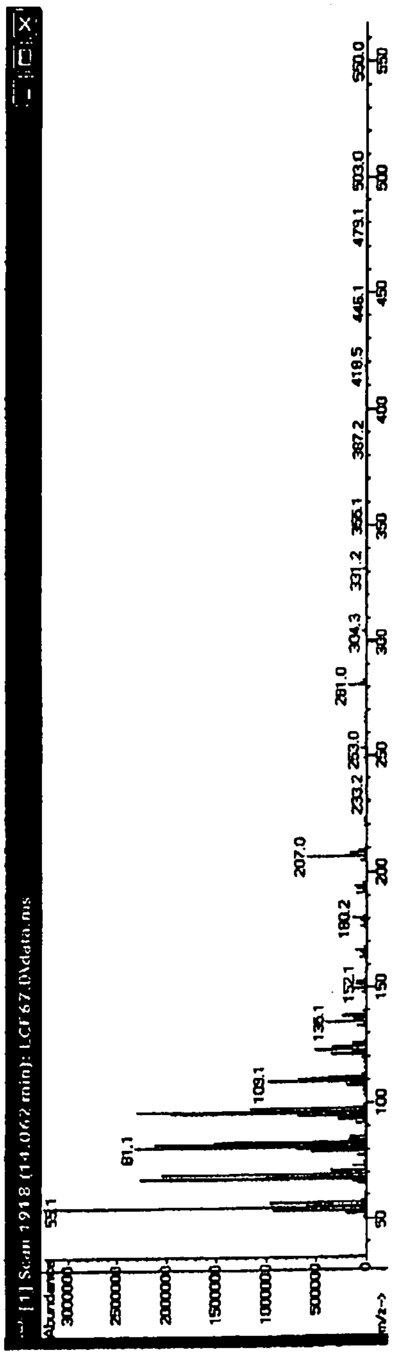

FIG. 4I C31 triene
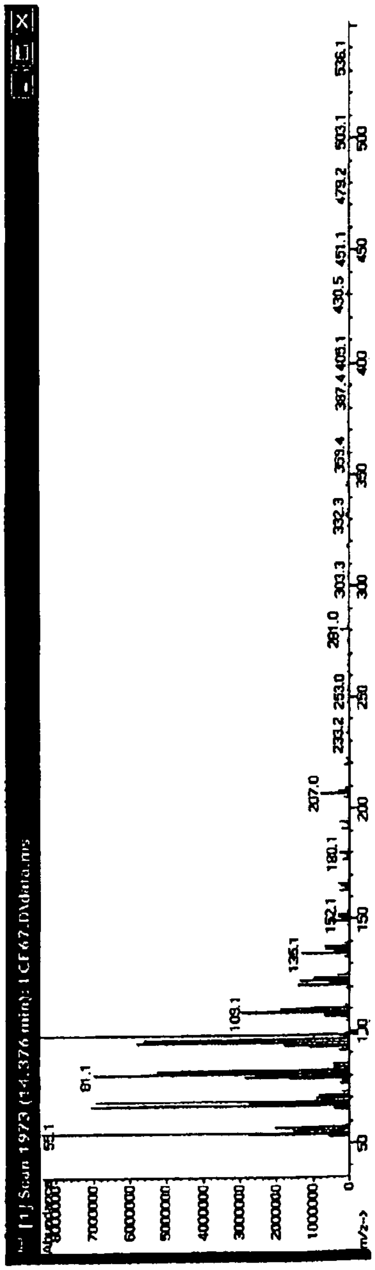
FIG. 4J C31 diene
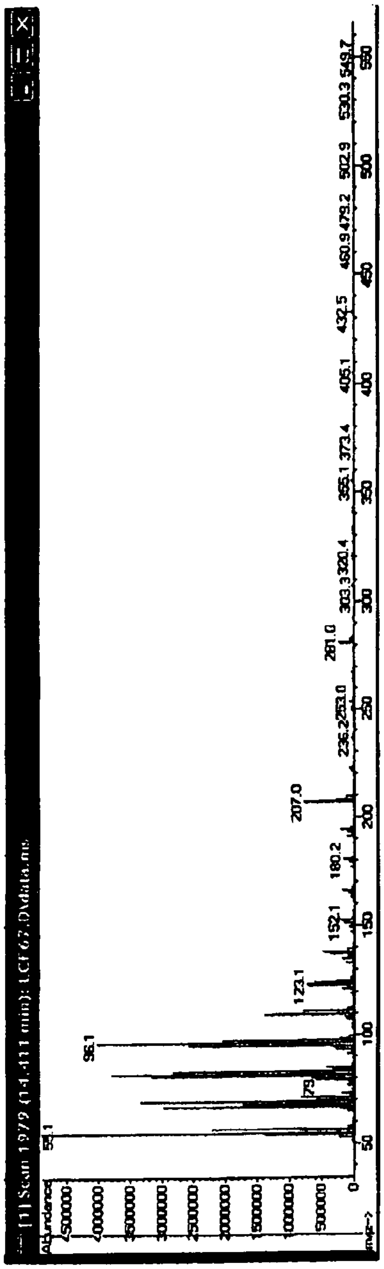

FIG. 7

| ORY | GENE | NAME | N | EC NUMBER | MODIFICATION | USE | ORGANISM |
|---|---|---|---|---|---|---|---|
| 1. Fatty Acid Production Increase / Product Production Increase<br><br>*increase acyl-CoA*<br>*reduce catabolism of derivatives and intermediates*<br>*reduce feedback inhibition*<br>*attenuate other pathways that consume fatty acids* | | | | | | | |
| | accA | Acetyl-CoA carboxylase, subunit A (carboxyltransferase alpha) | AAC73296, NP_414727 | 6.4.1.2 | Over-express | increase Malonyl-CoA production | *Escherichia coli, Lactococci* |
| | accB | Acetyl-CoA carboxylase, subunit B (BCCP: biotin carboxyl carrier protein) | NP_417721 | 6.4.1.2 | Over-express | increase Malonyl-CoA production | *Escherichia coli, Lactococci* |
| | accC | Acetyl-CoA carboxylase, subunit C (biotin carboxylase) | NP_417722 | 6.4.1.2, 6.3.4.14 | Over-express | increase Malonyl-CoA production | *Escherichia coli, Lactococci* |
| | accD | Acetyl-CoA carboxylase, subunit D (carboxyltransferase beta) | NP_416819 | 6.4.1.2 | Over-express | increase Malonyl-CoA production | *Escherichia coli, Lactococci* |
| | aceE | pyruvate dehydrogenase, subunit E1 | NP_414656, AAC73226 | 1.2.4.1 | Over-express | increase Acetyl-CoA production | *Escherichia coli* |
| | aceF | pyruvate dehydrogenase, subunit E2 | NP_414657 | 2.3.1.12 | Over-express | increase Acetyl-CoA production | *Escherichia coli* |
| | ackA | acetate kinase | AAC75356, NP_416799 | 2.7.2.1 | Delete or reduce | increase Acetyl-CoA production | *Escherichia coli* |

FIG. 7 (cont.)

| | | | | | | | |
|---|---|---|---|---|---|---|---|
| | ackB | acetate kinase AckB | BAB81430 | 2.7.2.1 | Delete or reduce | increase Acetyl-CoA production | *Escherichia coli* |
| | acpP | acyl carrier protein | AAC74178 | NONE | Over-express | increase Acetyl-CoA production | *Escherichia coli* |
| | fadD | acyl-CoA synthase | AP_002424 | 2.3.1.86, 6.2.1.3 | Over-express | increase Fatty acid production | *Escherichia coli W3110* |
| | adhE | alcohol dehydrogenase | CAA47743 | 1.1.1.1, 1.2.1.10 | Delete or reduce | increase Acetyl-CoA production | *Escherichia coli W3111* |
| | cer1 | Aldehyde decarbonylase | BAA11024 | 4.1.99.5 | Over-express | increase Acetyl-CoA production | *Arabidopsis thaliana* |
| | fabA | beta-hydroxydecanoyl thioester dehydrase | NP_415474 | 4.2.1.60 | express | fatty acyl-CoA production | *E. coli K12* |
| | fabD | [acyl-carrier-protein] S-malonyltransferase | AAC74176 | 2.3.1.39 | Over-express | increase Acetyl-CoA production | *E. coli K12* |
| | fabF | 3-oxoacyl-[acyl-carrier-protein] synthase II | AAC74179 | 2.3.1.179 | Delete or OverExpress | increase Acetyl-CoA production | *E. coli K12* |
| | fabG | 3-oxoacyl-[acyl-carrier protein] reductase | AAC74177 | 1.1.1.100 | Over-express | increase Acetyl-CoA production | *E. coli K12* |
| | fabH | 3-oxoacyl-[acyl-carrier-protein] synthase III | AAC74175 | 2.3.1.180 | Over-express | increase Acetyl-CoA production | *E. coli K12, lactococci* |
| | fabI | enoyl-[acyl-carrier-protein] reductase, NADH-dependent | NP_415804 | 1.3.1.9 | express | fatty acyl-CoA production | *E. coli K12, lactococci* |
| | fabR | Transcriptional Repressor | NP_418398 | NONE | Delete or reduce | modulate unsaturated fatty acid production | *E. coli K12* |
| | fabZ | (3R)-hydroxymyristol acyl carrier protein dehydratase | NP_414722 | 4.2.1.- | | | *E. coli K12* |
| | fadE | acyl-CoA dehydrogenase | AAC73325 | 1.3.99.3, 1.3.99.- | Delete or reduce | increase Acetyl-CoA production | |
| | acr1 | Fatty Acyl-CoA reductase | YP_047869, AAC45217 | 1.2.1.42 | Over-express | for fatty alcohol production | *Acinetobacter sp., i.e. calcoaceticus* |
| | GST, gshB | Glutathione synthase | P04425 | 6.3.2.3 | Delete or reduce | increase Acyl-CoA | *E. coli K12* |
| | gpsA | biosynthetic sn-glycerol 3-phosphate dehydrogenase | AAC76632, NP_418065 | EC: 1.1.1.94 | Delete or reduce | increase Acetyl-CoA production | *E. coli K12* |
| | ldhA | lactate dehydrogenase | AAC74462, NP_415898 | EC: 1.1.1.27, 1.1.1.28 | Delete or reduce | increase Acetyl-CoA production | *E. coli K12* |
| | Lipase | Triglyceride Lipase | CAA89087, CAA98876 | 3.1.1.3 | express | increase Fatty acid production | *Saccharomyces cerevisiae* |

FIG. 7 (cont.)

| | | | | | | | |
|---|---|---|---|---|---|---|---|
| | | Malonyl-CoA decarboxylase | AAA26500 | 4.1.1.9, 4.1.1.41 | Over-express | | *Saccharopolyspora erythraea* |
| | panD | aspartate 1-decarboxylase | BAB96708 | 4.1.1.11 | Over-express | increase Acyl-CoA | *Escherichia coli W3110* |
| | panK a.k.a. coaA | pantothenate kinase | AAC76952 | 2.7.1.33 | Over-express | increase Acetyl-CoA production | *E. coli* |
| | panK a.k.a. coaA, R106K | pantothenate kinase | AAC76952 | 2.7.1.33 | Express, Over-express, R106K mutation | increase Acetyl-CoA production | *E. coli* |
| | pdh | Pyruvate dehydrogenase | BAB34380, AAC73226, NP_415392 | 1.2.4.1 | Over-express | increase Acetyl-CoA production | |
| | pflB | formate acetyltransferase (pyruvate formate lyase) | AAC73989, P09373 | EC: 2.3.1.54 | Delete or reduce | increase Acetyl-CoA production | |
| | plsB | acyltransferase | AAC77011 | 2.3.1.15 | D311E mutation | reduce limits on Acyl-CoA pool | *E. coli K12* |
| | poxB | pyruvate oxidase | AAC73958, NP_415392 | 1.2.2.2 | Delete or reduce | increase Acetyl-CoA production | |
| | pta | phosphotransacetylase | AAC75357, NP_416800 | 2.3.1.8 | Delete or reduce | increase Acetyl-CoA production | |
| | udhA | pyridine nucleotide transhydrogenase | CAA46822 | 1.6.1.1 | Over-express | conversion NADH to NADPH or vice versa | |
| | fadB | fused 3-hydroxybutyryl-CoA epimerase/delta(3)-cis-delta(2)-trans-enoyl-CoA isomerase/enoyl-CoA hydratase and 3-hydroxyacyl-CoA dehydrogenase | AP_003956 | 4.2.1.17, 5.1.2.3, 5.3.3.8, 1.1.1.35 | Delete or reduce | Block fatty acid degradation | *E. coli* |
| | fadJ | 3-hydroxyacyl-CoA dehydrogenase; K01692 enoyl-CoA hydratase; K01782 3-hydroxybutyryl-CoA epimerase | AAC75401 | 1.1.1.35, 4.2.1.17, 5.1.2.3 | Delete or reduce | Block fatty acid degradation | *E. coli* |
| | fadA | 3-ketoacyl-CoA thiolase | BAE77458 | 2.3.1.16 | Delete or reduce | Block fatty acid degradation | *E. coli* |
| | fadI | beta-ketoacyl-CoA thiolase | AAC75402 | 2.3.1.16 | Delete or reduce | Block fatty acid degradation | *E. coli* |
| | YdiO | acyl-coA dehydrogenase | YP_852786 | 1.3.99.- | Delete or reduce | Block fatty acid degradation | *E. coli* |

FIG. 7 (cont.)

| | | | | | | | |
|---|---|---|---|---|---|---|---|
| 2. Structure Control | | | | | | | |
| | | | | | | | |
| 2A. Chain Length Control | | | | | | | |
| 2 | tesA | thioesterase | P0ADA1 | 3.1.2.-, 3.1.1.5 | Delete and/or express | C18 Chain Length | |
| | tesA without leader sequence | thioesterase | AAC73596, NP_415027 | 3.1.2.-, 3.1.1.5 | express or overexpress | C18:1 | *E.coli* |
| | tesA without leader | thioesterase | P0ADA1 | 3.1.2.-, 3.1.1.5 | Express and/or overexpress mutation | <C18 Chain Length | *E. coli* |
| | fatB1 (umbellularia) | thioesterase | Q41635 | 3.1.2.14 | express or overexpress | C12:0 | *Umbellularia californica* |
| | fatB2 (umbellularia)DELETE umbelluria) | thioesterase | AAC49269 | 3.1.2.14 | express or overexpress | C8:0 - C10:0 | *Cuphea hookeriana* |
| | fatB3 | thioesterase | AAC72881 | 3.1.2.14 | express or overexpress | C14:0 - C16:0 | *Cuphea hookeriana* |
| | fatB (cinnamonum) | thioesterase | Q39473 | 3.1.2.14 | express or overexpress | C14:0 | *Cinnamomum camphora* |
| | fatB[M141T]* | thioesterase | CAA85388 | 3.1.2.14 | express or overexpress | C16:1 | *Arabidopsis thaliana* |
| | fatA1 (Helianthus) | thioesterase | AAL79361 | 3.1.2.14 | express or overexpress | *C18:1* | *Helianthus annuus* |
| | atfata (ARABIDOPSIS FATA ACYL-ACP THIOESTERASE) | thioesterase | NP_189147, NP_193041 | 3.1.2.14 | express or overexpress | C18:1 | *Arabidopsis thaliana* |
| | fatA | thioesterase | CAC39106 | 3.1.2.14 | express or overexpress | C18:1 | *Brassica juncea* |
| | fatA (cuphea) | thioesterase | AAC72883 | 3.1.2.14 | express or overexpress | C18:1 | *Cuphea hookeriana* |
| | | | | | | | |
| 2B. Branching Control | | | | | | | |
| | *alternate FabH* | | | | | | |

FIG. 7 (cont.)

| | | | | | | | |
|---|---|---|---|---|---|---|---|
| | *express FabH from S. glaucescens or S. coelicolor and knock out endogenouse FabH* | | | | | increase branched chain fatty acid derivatives | |
| | *express FabH from B. subtilis and knock out endogenouse FabH* | | | | | | |
| | *bdk - E3 - dihydrolipoyl dehyrodgenase subunit* | | | EC 1.2.4.4 | | | |
| | *bkd - E1-alpha/beta subunit* | decarboxylase subunits of branched chain a-ketoacid dehydrogenase complex | | EC 1.2.4.4 | | | |
| | *bkd - E2 - dihydrolipoyl transacylase subunit* | | | EC 1.2.4.4 | | | |
| | bkdA1 | branched-chain a-ketoacid dehydrogenase a-subunit (E1a) | NP_628006 | EC 1.2.4.4 | express or Over-Express | make branched-chain acyl-CoA precursors | *Streptomyces coelicolor* |
| | bkdB1 | branched-chain a-ketoacid dehydrogenase a-subunit (E1b) | NP_628005 | EC 1.2.4.4 | express or Over-Express | make branched-chain acyl-CoA precursors | *Streptomyces coelicolor* |
| | bkdC1 | dihydrolipoyl transacetylase (E2) | NP_628004 | EC 2.3.1.168 | express or Over-Express | make branched-chain acyl-CoA precursors | *Streptomyces coelicolor* |
| | bkdA2 | branched-chain a-ketoacid dehydrogenase a-subunit (E1a) | NP_733618 | EC 1.2.4.4 | express or Over-Express | make branched-chain acyl-CoA precursors | *Streptomyces coelicolor* |
| | bkdB2 | branched-chain a-ketoacid dehydrogenase b-subunit (E1b) | NP_628019 | EC 1.2.4.4 | express or Over-Express | make branched-chain acyl-CoA precursors | *Streptomyces coelicolor* |
| | bkdC2 | dihydrolipoyl transacetylase (E2) | NP_628018 | EC 2.3.1.168 | express or Over-Express | make branched-chain acyl-CoA precursors | *Streptomyces coelicolor* |
| | bkdA | branched-chain a-ketoacid dehydrogenase a-subunit (E1a) | BAC72074 | EC 1.2.4.4 | express or Over-Express | make branched-chain acyl-CoA precursors | *Streptomyces avermitilis* |

FIG. 7 (cont.)

| | | | | | | | |
|---|---|---|---|---|---|---|---|
| | bkdB | branched-chain a-ketoacid dehydrogenase b-subunit (E1b) | BAC72075 | EC 1.2.4.4 | express or Over-Express | make branched-chain acyl-CoA precursors | *Streptomyces avermitilis* |
| | bkdC | dihydrolipoyl transacetylase (E2) | BAC72076 | EC 2.3.1.168 | express or Over-Express | make branched-chain acyl-CoA precursors | *Streptomyces avermitilis* |
| | bkdF | branched-chain a-ketoacid dehydrogenase a-subunit (E1a) | BAC72088 | EC 1.2.4.4 | express or Over-Express | make branched-chain acyl-CoA precursors | *Streptomyces avermitilis* |
| | bkdG | branched-chain a-ketoacid dehydrogenase b-subunit (E1b) | BAC72089 | EC 1.2.4.4 | express or Over-Express | make branched-chain acyl-CoA precursors | *Streptomyces avermitilis* |
| | bkdH | dihydrolipoyl transacetylase (E2) | BAC72090 | EC 2.3.1.168 | express or Over-Express | make branched-chain acyl-CoA precursors | *Streptomyces avermitilis* |
| | bkdAA | branched-chain a-ketoacid dehydrogenase a-subunit (E1a) | NP_390285 | EC 1.2.4.4 | express or Over-Express | make branched-chain acyl-CoA precursors | *Bacillus subtilis* |
| | bkdAB | branched-chain a-ketoacid dehydrogenase b-subunit (E1b) | NP_390284 | EC 1.2.4.4 | express or Over-Express | make branched-chain acyl-CoA precursors | *Bacillus subtilis* |
| | bkdB | dihydrolipoyl transacetylase (E2) | NP_390283 | EC 2.3.1.168 | express or Over-Express | make branched-chain acyl-CoA precursors | *Bacillus subtilis* |
| | bkdA1 | branched-chain a-ketoacid dehydrogenase a-subunit (E1a) | AAA65614 | EC 1.2.4.4 | express or Over-Express | make branched-chain acyl-CoA precursors | *Pseudomonas putida* |
| | bkdA2 | branched-chain a-ketoacid dehydrogenase b-subunit (E1b) | AAA65615 | EC 1.2.4.4 | express or Over-Express | make branched-chain acyl-CoA precursors | *Pseudomonas putida* |
| | bkdC | dihydrolipoyl transacetylase (E2) | AAA65617 | EC 2.3.1.168 | express or Over-Express | make branched-chain acyl-CoA precursors | *Pseudomonas putida* |
| | lpd | dihydrolipoamide dehydrogenase (E3) | NP_414658 | 1.8.1.4 | express or Over-Express | make branched-chain acyl-CoA precursors | *Escherichia coli* |
| | IlvE | branched-chain amino acid aminotransferase | YP_026247 | 2.6.1.42 | express or Over-Express | make branched a-ketoacids | *Escherichia coli* |
| | IlvE | branched-chain amino acid aminotransferase | AAF34406 | 2.6.1.42 | express or Over-Express | make branched a-ketoacids | *Lactococcus lactis* |
| | IlvE | branched-chain amino acid aminotransferase | NP_745648 | 2.6.1.42 | express or Over-Express | make branched a-ketoacids | *Pseudomonas putida* |
| | IlvE | branched-chain amino acid aminotransferase | NP_629657 | 2.6.1.42 | express or Over-Express | make branched a-ketoacids | *Streptomyces coelicolor* |
| | ccr | crotonyl-CoA reductase | NP_630556 | 1.6.5.5,1.1.1.1 | express or Over-Express | Converting crotonyl-CoA to butyryl-CoA | *Streptomyces coelicolor* |
| | ccr | crotonyl-CoA reductase | AAD53915 | 1.6.5.5,1.1.1.1 | express or Over-Express | Converting crotonyl-CoA to butyryl-CoA | *Streptomyces cinnamonensis* |

FIG. 7 (cont.)

| | | | | | | | |
|---|---|---|---|---|---|---|---|
| | IcmA, isobutyryl-CoA mutase | isobutyryl-CoA mutase, subunit A | NP_629554 | 5.4.99.2 | express or Over-Express | converting butyryl-CoA to isobutyryl-CoA | *Streptomyces coelicolor* |
| | IcmA, isobutyryl-CoA mutase | isobutyryl-CoA mutase, subunit A | AAC08713 | 5.4.99.2 | express or Over-Express | converting butyryl-CoA to isobutyryl-CoA | *Streptomyces cinnamonensis* |
| | IcmB, isobutyryl-CoA mutase | isobutyryl-CoA mutase, subunit B | NP_630904 | 5.4.99.2 | express or Over-Express | converting butyryl-CoA to isobutyryl-CoA | *Streptomyces coelicolor* |
| | IcmB, isobutyryl-CoA mutase | isobutyryl-CoA mutase, subunit B | CAB59633 | 5.4.99.2 | express or Over-Express | converting butyryl-CoA to isobutyryl-CoA | *Streptomyces cinnamonensis* |
| | FabH, ACPs and fabF genes with specificity for branched chain acyl-CoAs | | | | | | |
| | IlvE | branched-chain amino acid aminotransferase | CAC12788 | EC2.6.1.42 | over express | branched chain amino acid amino transferase | Staphylococcus carnosus |
| | FabH1 | beta-ketoacyl-ACP synthase III | NP_626634 | 2.3.1.180 | express or Over-Express | initiation of branched-chain fatty acid biosynthesis | Streptomyces coelicolor |
| | ACP | acyl-carrier protein | NP_626635 | NONE | express or Over-Express | initiation and elongation of branched-chain fatty acid biosynthesis | *Streptomyces coelicolor* |
| | FabF | beta-ketoacyl-ACP synthase II | NP_626636 | 2.3.1.179 | express or Over-Express | elongation of branched-chain fatty acid biosynthesis | *Streptomyces coelicolor* |
| | FabH3 | beta-ketoacyl-ACP synthase III | NP_823466 | 2.3.1.180 | express or Over-Express | initiation of branched-chain fatty acid biosynthesis | *Streptomyces avermitilis* |
| | FabC3 (ACP) | acyl-carrier protein | NP_823467 | NONE | express or Over-Express | initiation and elongation of branched-chain fatty acid biosynthesis | *Streptomyces avermitilis* |

FIG. 7 (cont.)

| | | | | | | | |
|---|---|---|---|---|---|---|---|
| | FabF | beta-ketoacyl-ACP synthase II | NP_823468 | 2.3.1.179 | express or Over-Express | elongation of branched-chain fatty acid biosynthesis | *Streptomyces avermitilis* |
| | FabH_A | beta-ketoacyl-ACP synthase III | NP_389015 | 2.3.1.180 | express or Over-Express | initiation of branched-chain fatty acid biosynthesis | *Bacillus subtillis* |
| | FabH_B | beta-ketoacyl-ACP synthase III | NP_388898 | 2.3.1.180 | express or Over-Express | initiation of branched-chain fatty acid biosynthesis | *Bacillus subtillis* |
| | ACP | acyl-carrier protein | NP_389474 | NONE | express or Over-Express | initiation and elongation of branched-chain fatty acid biosynthesis | *Bacillus subtillis* |
| | FabF | beta-ketoacyl-ACP synthase II | NP_389016 | 2.3.1.179 | express or Over-Express | elongation of branched-chain fatty acid biosynthesis | *Bacillus subtillis* |
| | SmalDRAFT_0818 | beta-ketoacyl-ACP synthase III | ZP_01643059 | 2.3.1.180 | express or Over-Express | initiation of branched-chain fatty acid biosynthesis | *Stenotrophomonas maltophilia* |
| | SmalDRAFT_0821 | acyl-carrier protein | ZP_01643063 | NONE | express or Over-Express | initiation and elongation of branched-chain fatty acid biosynthesis | *Stenotrophomonas maltophilia* |
| | SmalDRAFT_0822 | beta-ketoacyl-ACP synthase II | ZP_01643064 | 2.3.1.179 | express or Over-Express | elongation of branched-chain fatty acid biosynthesis | *Stenotrophomonas maltophilia* |
| | FabH | beta-ketoacyl-ACP synthase III | YP_123672 | 2.3.1.180 | express or Over-Express | initiation of branched-chain fatty acid biosynthesis | *Legionella pneumophila* |
| | ACP | acyl-carrier protein | YP_123675 | NONE | express or Over-Express | initiation and elongation of branched-chain fatty acid biosynthesis | *Legionella pneumophila* |
| | FabF | beta-ketoacyl-ACP synthase II | YP_123676 | 2.3.1.179 | express or Over-Express | elongation of branched-chain fatty acid biosynthesis | *Legionella pneumophila* |

FIG. 7 (cont.)

| | | | | | | | |
|---|---|---|---|---|---|---|---|
| | FabH | beta-ketoacyl-ACP synthase III | NP_415609 | 2.3.1.180 | delete or reduce | initiation of branched-chain fatty acid biosynthesis | *Escherichia coli* |
| | FabF | beta-ketoacyl-ACP synthase II | NP_415613 | 2.3.1.179 | delete or reduce | elongation of branched-chain fatty acid biosynthesis | *Escherichia coli* |
| *To Produce Cyclic Fatty Acids* | | | | | | | |
| | AnsJ | dehydratase (putative) | not available | not available | express or Over-Express | cyclohexylcarbonyl-CoA boiosynthesis | *Streptomyces collinus* |
| | AnsK | CoA ligase (putative) | not available | not available | express or Over-Express | cyclohexylcarbonyl-CoA boiosynthesis | *Streptomyces collinus* |
| | AnsL | dehydrogenase (putative) | not available | not available | express or Over-Express | cyclohexylcarbonyl-CoA boiosynthesis | *Streptomyces collinus* |
| | ChcA | enoyl-CoA reductase | U72144 | EC 1.3.1.34 | express or Over-Express | cyclohexylcarbonyl-CoA boiosynthesis | *Streptomyces collinus* |
| | AnsM | oxidoreductase (putative) | not available | not available | express or Over-Express | cyclohexylcarbonyl-CoA boiosynthesis | *Streptomyces collinus* |
| | PlmJ | dehydratase (putative) | AAQ84158 | not available | express or Over-Express | cyclohexylcarbonyl-CoA boiosynthesis | *Streptomyces sp. HK803* |
| | PlmK | CoA ligase (putative) | AAQ84158 | not available | express or Over-Express | cyclohexylcarbonyl-CoA boiosynthesis | *Streptomyces sp. HK803* |
| | PlmL | dehydrogenase (putative) | AAQ84159 | not available | express or Over-Express | cyclohexylcarbonyl-CoA boiosynthesis | *Streptomyces sp. HK803* |
| | ChcA | enoyl-CoA reductase | AAQ84160 | EC 1.3.1.34 | express or Over-Express | cyclohexylcarbonyl-CoA boiosynthesis | *Streptomyces sp. HK803* |
| | PlmM | oxidoreductase (putative) | AAQ84161 | not available | express or Over-Express | cyclohexylcarbonyl-CoA boiosynthesis | *Streptomyces sp. HK803* |
| | ChcB | enoyl-CoA isomerase | AF268489 | not available | express or Over-Express | cyclohexylcarbonyl-CoA boiosynthesis | *Streptomyces collinus* |
| | ChcB/CaiD | enoyl-CoA isomerase | NP_629292 | 4.2.1.- | express or Over-Express | cyclohexylcarbonyl-CoA boiosynthesis | *Streptomyces coelicolor* |
| | ChcB/CaiD | enoyl-CoA isomerase | NP_824296 | 4.2.1.- | express or Over-Express | cyclohexylcarbonyl-CoA boiosynthesis | *Streptomyces avermitilis* |
| | | | | | | | |
| 2C. Saturation Level Control | | | | | | | |
| | Sfa | Suppressor of FabA | AAN79592, AAC44390 | NONE | Over-express | increase monounsaturated fatty acids | *E.coli* |

FIG. 7 (cont.)

| | | | | | | | |
|---|---|---|---|---|---|---|---|
| | also see FabA in sec. 1 | | | | express | produce unsaturated fatty acids | |
| | GnsA | suppressors of the secG null mutation | ABD18647.1 | NONE | Over-express | increase unsaturated fatty acid esters | *E.coli* |
| | GnsB | suppressors of the secG null mutation | AAC74076.1 | NONE | Over-express | increase unsaturated fatty acid esters | *E.coli* |
| | also see section 2A - items with :0 are unsaturated (no double bonds) and with :1 are saturated (1 double bond) | | | | | | |
| | fabB | 3-oxoacyl-[acyl-carrier-protein] synthase I | BAA16180 | EC:2.3.1.41 | overexpress | modulate unsaturated fatty acid production | *Escherichia coli* |
| | fabK | trans-2-enoyl-ACP reductase II | AAF98273 | 1.3.1.9 | express | modulate unsaturated fatty acid production | *Streptococcus pneumoniae* |
| | fabL | enoyl-(acyl carrier protein) reductase | AAU39821 | 1.3.1.9 | express | modulate unsaturated fatty acid production | *Bacillus licheniformis DSM 13* |
| | fabM | trans-2, cis-3-decenoyl-ACP isomerase | DAA05501 | 4.2.1.17 | Over-express | modulate unsaturated fatty acid production | *Streptococcus mutans* |
| | | | | | | | |
| 3. Final Product Output | | | | | | | |
| | | | | | | | |
| 3A. Wax Output | | | | | | | |
| | AT3G51970 | long-chain-alcohol O-fatty-acyltransferase | NP_190765 | 2.3.1.26 | express | wax production | *Arabidopsis thaliana* |
| | | thioesterase (see chain length control section) | | | express | increase fatty acid production | |
| | | fatty alcohol forming acyl-CoA reductase | | 1.1.1.* | express | convert acyl-coa to fatty alcohol | |
| | acr1 | acyl-CoA reductase (ACR1) | YP_047869 | 1.2.1.42 | express | convert acyl-coa to fatty alcohol | *Acinetobacter sp. ADP1* |
| | yqhD | alcohol dehydrogenase | AP_003562 | 1.1.-.- | express | increase | *E. coli W3110* |

FIG. 7 (cont.)

| | | | | | | | |
|---|---|---|---|---|---|---|---|
| | ELO1 | Fatty acid elongase | BAD98251 | 2.3.1.- | express | produce very long chain length fatty acids | *Pichia angusta* |
| | plsC | acyltransferase | AAA16514 | 2.3.1.51 | express | | *Saccharomyces cerevisiae* |
| | DAGAT/DGAT | diacylglycerol acyltransferase | AAF19262 | 2.3.1.20 | express | wax production | *Arabidopsis thaliana* |
| | hWS | acyl-CoA wax alcohol acyltransferase | AAX48018 | 2.3.1.20 | express | wax production | *Homo sapiens* |
| | aft1 | bifunctional wax ester synthase/acyl-CoA:diacylglycerol acyltransferase | AAO17391 | 2.3.1.20 | express | wax production | *Acinetobacter sp. ADP1* |
| | mWS | wax ester synthase (simmondsia) | AAD38041 | 2.3.1.- | express | wax production | *Simmondsia chinensis* |
| | | | | | | | |
| 3B. Fatty Alcohol Output | | | | | | | |
| | | various thioesterases (refer to Sec. 2A) | | | express | produce | |
| | acr1 | acyl-CoA reductase | YP_047869 | 1.2.1.42 | express | produce | *Acinetobacter sp. ADP1* |
| | yqhD | alcohol dehydrogenase | AP_003562 | 1.1.-.- | express | produce | *Escherichia coli W3110* |
| | BmFAR | FAR (fatty alcohol forming acyl-CoA reductase) | BAC79425 | 1.1.1.* | express | reduce fatty acyl-CoA to fatty alcohol | *Bombyx mori* |
| | Akr1a4 | Mammalian microsomal aldehyde reductase | NP_067448 | 1.1.1.2 | express | produce | *Mus musculus* |
| | GTNG_1865 | Long-chain aldehyde dehydrogenase | YP_001125970 | 1.2.1.3 | express | produce | *Geobacillus thermodenitrificans NG80-2* |
| | FadD | acyl-CoA synthetase | NP_416319 | EC 6.2.1.3 | express | produce more | *E. Coli K12* |
| *To make Butanol* | | | | | | | |
| | atoB | acetyl-CoA acetyltransferase | YP_049388 | 2.3.1.9 | express | produce | *Erwinia carotovora* |
| | hbd | Beta-hydroxybutyryl-CoA dehydrogenase | BAD51424 | 1.1.1.157 | express | produce | *Butyrivibrio fibrisolvens* |
| | CPE0095 | crotonase | BAB79801 | 4.2.1.55 | express | produce | *Clostridium perfringens* |

FIG. 7 (cont.)

| | | | | | | | |
|---|---|---|---|---|---|---|---|
| | bcd | butyryl-CoA dehydrogenase | AAM14583 | 1.3.99.2 | express | produce | *Clostridium beijerinckii* |
| | ALDH | coenzyme A-acylating aldehyde dehydrogenase | AAT66436 | 1.2.1.3 | express | produce | *Clostridium beijerinckii* |
| | AdhE | aldehyde-alcohol dehydrogenase | AAN80172 | 1.1.1.1 1.2.1.10 | express | produce | *Escherichia coli CFT073* |
| | | | | | | | |
| | | | | | | | |
| 3C. Fatty Acid Ester Output | | | | | | | |
| | thioesterase | see chain length control section | | | express | produce | |
| | acr1 | acyl-CoA reductase | YP_047869 | 1.2.1.42 | express | produce | *Acinetobacter sp. ADP1* |
| | yqhD | alcohol dehydrogenase | AP_003562 | 1.1.-.- | express | produce | *E. Coli K12* |
| | AAT | alcohol O-acetyltransferase | AAG13130 | 2.3.1.84 | express | produce | *Fragaria x ananassa* |
| | | | | | | | |
| 4. Export | | | | | | | |
| | Wax ester exporter (FATP family, Fatty Acid (long chain) Transport Protein) | | NP_524723 | NONE | express | export wax | *Drosophila melanogaster* |
| | ABC transporter | putative alkane transporter | AAN73268 | NONE | express | export products | *Rhodococcus erythropolis* |
| | CER5 | wax transporter | At1g51500, AY734542, At3g21090, At1g51460 | NONE | express | export products | *Arabidopsis thaliana* |
| | AtMRP5 | Arabidopsis thaliana multidrug resistance-associated | NP_171908 | NONE | express | export products | *Arabidopsis thaliana* |
| | AmiS2 | ABC transporter AmiS2 | JC5491 | NONE | express | export products | *Rhodococcus sp.* |
| | AtPGP1 | ARABIDOPSIS THALIANA P GLYCOPROTEIN1 | NP_181228 | NONE | express | export products | *Arabidopsis thaliana* |

FIG. 7 (cont.)

| | | | | | | | |
|---|---|---|---|---|---|---|---|
| | AcrA | putative multidrug-efflux transport protein acrA | CAF23274 | NONE | express | export products | *Candidatus Protochlamydia amoebophila UWE25* |
| | AcrB | probable multidrug-efflux transport protein, acrB | CAF23275 | NONE | express | export products | *Candidatus Protochlamydia amoebophila UWE25* |
| | TolC | Outer membrane protein [Cell envelope biogenesis, | ABD59001 | NONE | express | export products | *Francisella tularensis subsp. novicida* |
| | AcrE | transmembrane protein affects septum formation and cell membrane permeability | YP_312213 | NONE | express | export products | *Shigella sonnei Ss046* |
| | AcrF | Acriflavine resistance protein F | P24181 | NONE | express | export products | *Escherichia coli* |
| | tll1618 | multidrug efflux transporter | NP_682408.1 | NONE | express | export products | *Thermosynechococcus elongatus BP-1]* |
| | tll1619 | multidrug efflux transporter | NP_682409.1 | NONE | express | export products | *Thermosynechococcus elongatus BP-1]* |
| | tll0139 | multidrug efflux transporter | NP_680930.1 | NONE | express | export products | *Thermosynechococcus elongatus BP-1]* |
| | | | | | | | |
| 5. Fermentation | | | | | | | |
| | replication checkpoint genes | | | | | increase output efficiency | |
| | umuD | DNA polymerase V, subunit | YP_310132 | 3.4.21.- | Over-express | increase output efficiency | *Shigella sonnei Ss046* |
| | umuC | DNA polymerase V, subunit | ABC42261 | 2.7.7.7 | Over-express | increase output efficiency | *Escherichia coli* |
| | NADH:NADPH transhydrogenase (alpha and beta subunits) (pntA, pntB) | | P07001, P0AB70 | 1.6.1.2 | express | increase output efficiency | *Shigella flexneri* |

SEQUENCE LISTING

```
<160> NUMBER OF SEQ ID NOS: 49

<210> SEQ ID NO 1
<211> LENGTH: 1017
<212> TYPE: DNA
<213> ORGANISM: Stenotrophomonas maltophilia

<400> SEQUENCE: 1
```

-continued atgctcttca agaatgtctc gatcgccggc ctggcacacg ttgatgcgcc gcatacgctg 60
acgaccaagg aaatcaacga gcggctgcag ccgacgttgg atcgcctcgg tatccgcacc 120
gacgtgctcg gcgatatcgc cggcatccat gcccgccgcc tgtgggacaa cggcgtgctt 180
gcgtccgatg ccgccaccat ggccggccgc aaggcgctgg aagacgcggg catcgatgcg 240
acgcaggtcg gcctgctggt caacacctcg gtcagccgcg actacctgga gccgtccacg 300
gcctccatcg tgtcgggcaa cctcggcgtc agcgacgagt gcatgacctt cgacgtcgcc 360
aatgcctgcc tggccttcat caacggcatg gacatcgcgg cgcgcatgat cgagcgcggc 420
gacatcgact acgcgctggt ggtggatggc gagaccgcca acctggtgta cgagaagacc 480
ctggagcgca tgaccgcccc ggacgtcacc gccgacgact tccgcaacga actggcggcg 540
ctgaccaccg gttcgggtgc tgcggcgatg gtgatggcgc gctcggagct ggtgccggac 600
gcgccgcgct acaagggcgg tgtcacccgt tcggccaccg agtggaacca gctgtgcctg 660
ggcaacctgg accggatggt caccgacacc cgcctgctgc tgatcgaagg catcaagctg 720
gcgcagaaga ccttcagcgc cgccaagatc gcactcggct gggctgtgga agaactggac 780
cagttcgtga tccaccaggt cagccagccg cacaccgccg cgttcatcaa gaacttcggc 840
atcgacccga agaaggtcat gaccatcttc ggcgagcacg gcaacatcgg cccggcctcg 900
gtgccgatcg tgctgagcaa gctcaagcag ctgggcaagc tgaagaaggg cgatcgcatc 960
gcgcttctgg gcattggctc gggcctgaac tgctcgatgg ctgaagtggt ctggtaa 1017

<210> SEQ ID NO 2
<211> LENGTH: 338
<212> TYPE: PRT
<213> ORGANISM: Stenotrophomonas maltophilia

<400> SEQUENCE: 2

Met Leu Phe Lys Asn Val Ser Ile Ala Gly Leu Ala His Val Asp Ala
1               5                   10                  15

Pro His Thr Leu Thr Thr Lys Glu Ile Asn Glu Arg Leu Gln Pro Thr
            20                  25                  30

Leu Asp Arg Leu Gly Ile Arg Thr Asp Val Leu Gly Asp Ile Ala Gly
        35                  40                  45

Ile His Ala Arg Arg Leu Trp Asp Asn Gly Val Leu Ala Ser Asp Ala
    50                  55                  60

Ala Thr Met Ala Gly Arg Lys Ala Leu Glu Asp Ala Gly Ile Asp Ala
65                  70                  75                  80

Thr Gln Val Gly Leu Leu Val Asn Thr Ser Val Ser Arg Asp Tyr Leu
                85                  90                  95

Glu Pro Ser Thr Ala Ser Ile Val Ser Gly Asn Leu Gly Val Ser Asp
            100                 105                 110

Glu Cys Met Thr Phe Asp Val Ala Asn Ala Cys Leu Ala Phe Ile Asn
        115                 120                 125

Gly Met Asp Ile Ala Ala Arg Met Ile Glu Arg Gly Asp Ile Asp Tyr
    130                 135                 140

Ala Leu Val Val Asp Gly Glu Thr Ala Asn Leu Val Tyr Glu Lys Thr
145                 150                 155                 160

Leu Glu Arg Met Thr Ala Pro Asp Val Thr Ala Asp Asp Phe Arg Asn
                165                 170                 175

Glu Leu Ala Ala Leu Thr Thr Gly Ser Gly Ala Ala Ala Met Val Met
            180                 185                 190

Ala Arg Ser Glu Leu Val Pro Asp Ala Pro Arg Tyr Lys Gly Gly Val
        195                 200                 205

```
Thr Arg Ser Ala Thr Glu Trp Asn Gln Leu Cys Leu Gly Asn Leu Asp
    210                 215                 220

Arg Met Val Thr Asp Thr Arg Leu Leu Leu Ile Glu Gly Ile Lys Leu
225                 230                 235                 240

Ala Gln Lys Thr Phe Ser Ala Ala Lys Ile Ala Leu Gly Trp Ala Val
                245                 250                 255

Glu Glu Leu Asp Gln Phe Val Ile His Gln Val Ser Gln Pro His Thr
            260                 265                 270

Ala Ala Phe Ile Lys Asn Phe Gly Ile Asp Pro Lys Lys Val Met Thr
        275                 280                 285

Ile Phe Gly Glu His Gly Asn Ile Gly Pro Ala Ser Val Pro Ile Val
    290                 295                 300

Leu Ser Lys Leu Lys Gln Leu Gly Lys Leu Lys Lys Gly Asp Arg Ile
305                 310                 315                 320

Ala Leu Leu Gly Ile Gly Ser Gly Leu Asn Cys Ser Met Ala Glu Val
                325                 330                 335

Val Trp


<210> SEQ ID NO 3
<211> LENGTH: 1017
<212> TYPE: DNA
<213> ORGANISM: Artificial sequence
<220> FEATURE:
<223> OTHER INFORMATION: Consensus sequence of optimized
      Stenotrophomonas maltophilia OleA

<400> SEQUENCE: 3

atgttattca aaaatgtatc tatcgctggt ctggctcatg tggatgctcc gcataccctg      60

accaccaagg agatcaacga acgcctgcaa ccgacgctgg atcgcctggg tatccgtacc     120

gacgtactgg gcgacatcgc tggtatccac gcacgtcgtc tgtgggacaa tggcgtactg     180

gcttctgatg ctgcaactat ggcaggccgt aaagcactgg aggacgctgg tattaacgcg     240

actcaggtag gcctgctggt aaacacctcc gtaagccgcg attacctgga gccttccacc     300

gcctccattg tgtctggcaa cctgggcgtg tctgatgaat gcatgacctt cgatgttgct     360

aacgcttgcc tggcattcat taacggtatg gatatcgcag cacgcatgat tgaacgcggt     420

gacatcgatt acgccctggt agtagacggt gaaaccgcaa atctggtgta cgaaaagacc     480

ctggaacgta tgactgcacc ggatgtgact gcagatgact tccgtaacga gctggctgct     540

ctgaccaccg gttctggcgc ggcagcgatg gtgatggctc gctccgagct ggtccctgat     600

gcgccgcgtt acaagggtgg tgtgacccgt agcgccaccg aatggaacca actgtgtctg     660

ggtaacctgg accgtatggt taccgacact cgtctgctgc tgatcgaagg tatcaagctg     720

gctcagaaaa cctttaccgc cgctaaaatt gctctgggtt gggcagtgga agaactggac     780

cagttcgtga ttcaccaggt cagccaaccg cacactgcgg cgttcatcaa gaacttcggt     840

atcgacccta aaaaggtgat gaccattttc ggtgagcacg gcaacatcgg cccagcttct     900

gtaccgatcg ttctgtctaa actgaaacag ctgggcaaac tgaaaaaggg cgaccgcatc     960

gcgctgctgg gcatcggtag cggcctgaac tgtagcatgg ctgaggttgt gtggtaa       1017


<210> SEQ ID NO 4
<211> LENGTH: 338
<212> TYPE: PRT
<213> ORGANISM: Artificial sequence
<220> FEATURE:
<223> OTHER INFORMATION: Consensus sequence of optimized
      Stenotrophomonas maltophilia OleA
```

<400> SEQUENCE: 4

```
Met Leu Phe Lys Asn Val Ser Ile Ala Gly Leu Ala His Val Asp Ala
1               5                   10                  15

Pro His Thr Leu Thr Thr Lys Glu Ile Asn Glu Arg Leu Gln Pro Thr
            20                  25                  30

Leu Asp Arg Leu Gly Ile Arg Thr Asp Val Leu Gly Asp Ile Ala Gly
        35                  40                  45

Ile His Ala Arg Arg Leu Trp Asp Asn Gly Val Leu Ala Ser Asp Ala
    50                  55                  60

Ala Thr Met Ala Gly Arg Lys Ala Leu Glu Asp Ala Gly Ile Asn Ala
65                  70                  75                  80

Thr Gln Val Gly Leu Leu Val Asn Thr Ser Val Ser Arg Asp Tyr Leu
                85                  90                  95

Glu Pro Ser Thr Ala Ser Ile Val Ser Gly Asn Leu Gly Val Ser Asp
            100                 105                 110

Glu Cys Met Thr Phe Asp Val Ala Asn Ala Cys Leu Ala Phe Ile Asn
        115                 120                 125

Gly Met Asp Ile Ala Ala Arg Met Ile Glu Arg Gly Asp Ile Asp Tyr
    130                 135                 140

Ala Leu Val Val Asp Gly Glu Thr Ala Asn Leu Val Tyr Glu Lys Thr
145                 150                 155                 160

Leu Glu Arg Met Thr Ala Pro Asp Val Thr Ala Asp Asp Phe Arg Asn
                165                 170                 175

Glu Leu Ala Ala Leu Thr Thr Gly Ser Gly Ala Ala Ala Met Val Met
            180                 185                 190

Ala Arg Ser Glu Leu Val Pro Asp Ala Pro Arg Tyr Lys Gly Gly Val
        195                 200                 205

Thr Arg Ser Ala Thr Glu Trp Asn Gln Leu Cys Leu Gly Asn Leu Asp
    210                 215                 220

Arg Met Val Thr Asp Thr Arg Leu Leu Leu Ile Glu Gly Ile Lys Leu
225                 230                 235                 240

Ala Gln Lys Thr Phe Thr Ala Ala Lys Ile Ala Leu Gly Trp Ala Val
                245                 250                 255

Glu Glu Leu Asp Gln Phe Val Ile His Gln Val Ser Gln Pro His Thr
            260                 265                 270

Ala Ala Phe Ile Lys Asn Phe Gly Ile Asp Pro Lys Lys Val Met Thr
        275                 280                 285

Ile Phe Gly Glu His Gly Asn Ile Gly Pro Ala Ser Val Pro Ile Val
    290                 295                 300

Leu Ser Lys Leu Lys Gln Leu Gly Lys Leu Lys Lys Gly Asp Arg Ile
305                 310                 315                 320

Ala Leu Leu Gly Ile Gly Ser Gly Leu Asn Cys Ser Met Ala Glu Val
                325                 330                 335

Val Trp
```

<210> SEQ ID NO 5
<211> LENGTH: 1659
<212> TYPE: DNA
<213> ORGANISM: Stenotrophomonas maltophilia

<400> SEQUENCE: 5

```
atgaaccgac cctgcaatat tgccgcccgc ttgcctgaac tggcgcgtga acggcccgac      60

cagatcgcca tccgctgccc gggccgccgt ggcgccggca acggcatggc cgcctacgac     120
```

gtgaccctgg attaccgcca gctggacgcc cgcagcgacg ccatggcggc tggcctggca 180
ggctacggga tcggtcgcgg ggtgcgcacg gtggtgatgg tgcggccgtc gccggagttc 240
ttcctgttga tgtttgccct gttcaaactg ggtgcggtgc cggtgctggt cgacccgggc 300
atcgacaaac gcgcgctgaa gcagtgcctg gatgaggcgc agccggaggc tttcattggc 360
attccgctgg cacacgtggc gcggttggcg ctgcgctggg cgcgctcggc gacccgcctg 420
gtcaccgtcg gccgccgcct cggctggggc gggaccacgc tggccgcgct ggagcgcgcc 480
ggtgccaacg ggggggcgat gctggccgcc accgatggcg aggacatggc cgcgatcctg 540
ttcaccagcg gctccaccgg cgtgcccaag ggcgtggtct accgccaccg tcatttcgtc 600
ggccagatcc agctgctggg cagtgccttt ggcatggaag cgggcggggt ggacctgccg 660
accttcccgc cgtttgcctt gttcgacccg gcgctgggcc tgacctcggt gatcccggac 720
atggacccga cccggccggc acaggccgac ccggcacgcc tgcatgacgc catccagcgc 780
ttcggcgtga cccagctgtt tggctcgcct gcgctgatgc gggtgctggc ccgtcacggc 840
cggccgttgc cgacggtgac ccgggtgacc tcggccggtg cgccggtgcc gccggatgtg 900
gtcgccacca tccgcagcct gttgccggcc gatgcgcagt tctggacccc gtacggcgcc 960
accgagtgcc tgccggtggc ggtggtggaa ggccgcgagc tggagcgcac ccgtgccgcc 1020
accgaggccg gtgccggtac ctgcgtgggc agcgtggttg aaccgaatga ggtgcgcatc 1080
atcggcatcg atgacggacc gttggccgac tggtcgcagg cgcgcgtgct ggccaccggc 1140
gaggtgggcg agatcaccgt ggccggaccg accgctaccg acagttactt caaccgcccg 1200
caggccaccg cggcggcgaa gatccgcgag accctggccg atggcagcac gcgcgtggtg 1260
caccgcatgg gtgacgtggg ctacttcgat gcgcagggcc gcctgtggtt ctgcggccgc 1320
aagacccatc gcgtggaaac cgcacggggg ccgctgtaca ccgaacaggt ggagccggtg 1380
ttcaataccg tgcccggggt ggcgcgcacg gcgctggtcg gtgttggtcc ggcgggagca 1440
caggtgccgg tgctgtgcgt ggagctgcag cgtggccagt cagacagccc ggcgctgcag 1500
gaggcgctgc gtgcgcacgc cgcagcccgc gcaccggaag ccggcctgca gcacttcctg 1560
gtgcatccgg cgttccccgt cgatatccgt cacaacgcca agatcggccg cgagaagctc 1620
gccgtctggg ccagcgccga actggagaag cgcgcatga 1659

<210> SEQ ID NO 6
<211> LENGTH: 552
<212> TYPE: PRT
<213> ORGANISM: Stenotrophomonas maltophilia

<400> SEQUENCE: 6

Met Asn Arg Pro Cys Asn Ile Ala Ala Arg Leu Pro Glu Leu Ala Arg
1 5 10 15

Glu Arg Pro Asp Gln Ile Ala Ile Arg Cys Pro Gly Arg Arg Gly Ala
20 25 30

Gly Asn Gly Met Ala Ala Tyr Asp Val Thr Leu Asp Tyr Arg Gln Leu
35 40 45

Asp Ala Arg Ser Asp Ala Met Ala Ala Gly Leu Ala Gly Tyr Gly Ile
50 55 60

Gly Arg Gly Val Arg Thr Val Val Met Val Arg Pro Ser Pro Glu Phe
65 70 75 80

Phe Leu Leu Met Phe Ala Leu Phe Lys Leu Gly Ala Val Pro Val Leu
85 90 95

Val Asp Pro Gly Ile Asp Lys Arg Ala Leu Lys Gln Cys Leu Asp Glu
100 105 110

-continued

```
Ala Gln Pro Glu Ala Phe Ile Gly Ile Pro Leu Ala His Val Ala Arg
        115                 120                 125

Leu Ala Leu Arg Trp Ala Arg Ser Ala Thr Arg Leu Val Thr Val Gly
    130                 135                 140

Arg Arg Leu Gly Trp Gly Gly Thr Thr Leu Ala Ala Leu Glu Arg Ala
145                 150                 155                 160

Gly Ala Asn Gly Gly Ala Met Leu Ala Ala Thr Asp Gly Glu Asp Met
                165                 170                 175

Ala Ala Ile Leu Phe Thr Ser Gly Ser Thr Gly Val Pro Lys Gly Val
            180                 185                 190

Val Tyr Arg His Arg His Phe Val Gly Gln Ile Gln Leu Leu Gly Ser
        195                 200                 205

Ala Phe Gly Met Glu Ala Gly Gly Val Asp Leu Pro Thr Phe Pro Pro
    210                 215                 220

Phe Ala Leu Phe Asp Pro Ala Leu Gly Leu Thr Ser Val Ile Pro Asp
225                 230                 235                 240

Met Asp Pro Thr Arg Pro Ala Gln Ala Asp Pro Ala Arg Leu His Asp
                245                 250                 255

Ala Ile Gln Arg Phe Gly Val Thr Gln Leu Phe Gly Ser Pro Ala Leu
            260                 265                 270

Met Arg Val Leu Ala Arg His Gly Arg Pro Leu Pro Thr Val Thr Arg
        275                 280                 285

Val Thr Ser Ala Gly Ala Pro Val Pro Pro Asp Val Val Ala Thr Ile
    290                 295                 300

Arg Ser Leu Leu Pro Ala Asp Ala Gln Phe Trp Thr Pro Tyr Gly Ala
305                 310                 315                 320

Thr Glu Cys Leu Pro Val Ala Val Val Glu Gly Arg Glu Leu Glu Arg
                325                 330                 335

Thr Arg Ala Ala Thr Glu Ala Gly Ala Gly Thr Cys Val Gly Ser Val
            340                 345                 350

Val Glu Pro Asn Glu Val Arg Ile Ile Gly Ile Asp Asp Gly Pro Leu
        355                 360                 365

Ala Asp Trp Ser Gln Ala Arg Val Leu Ala Thr Gly Glu Val Gly Glu
    370                 375                 380

Ile Thr Val Ala Gly Pro Thr Ala Thr Asp Ser Tyr Phe Asn Arg Pro
385                 390                 395                 400

Gln Ala Thr Ala Ala Ala Lys Ile Arg Glu Thr Leu Ala Asp Gly Ser
                405                 410                 415

Thr Arg Val Val His Arg Met Gly Asp Val Gly Tyr Phe Asp Ala Gln
            420                 425                 430

Gly Arg Leu Trp Phe Cys Gly Arg Lys Thr His Arg Val Glu Thr Ala
        435                 440                 445

Arg Gly Pro Leu Tyr Thr Glu Gln Val Glu Pro Val Phe Asn Thr Val
    450                 455                 460

Pro Gly Val Ala Arg Thr Ala Leu Val Gly Val Gly Pro Ala Gly Ala
465                 470                 475                 480

Gln Val Pro Val Leu Cys Val Glu Leu Gln Arg Gly Gln Ser Asp Ser
                485                 490                 495

Pro Ala Leu Gln Glu Ala Leu Arg Ala His Ala Ala Ala Arg Ala Pro
            500                 505                 510

Glu Ala Gly Leu Gln His Phe Leu Val His Pro Ala Phe Pro Val Asp
        515                 520                 525

Ile Arg His Asn Ala Lys Ile Gly Arg Glu Lys Leu Ala Val Trp Ala
```

530 535 540

Ser Ala Glu Leu Glu Lys Arg Ala
545 550

<210> SEQ ID NO 7
<211> LENGTH: 993
<212> TYPE: DNA
<213> ORGANISM: Stenotrophomonas maltophilia

<400> SEQUENCE: 7
atgaagatcc tggtcaccgg tggtggtggt ttccttggcc aggcgctgtg ccgtgggctg 60
gtcgaacgtg gccaccaggt gctggcgttc aaccgcagcc actacccgga actgcaggcc 120
atgggcgtgg gccagatccg cggcgatctg gccgatgcgc aggcggtgct gcatgcagtg 180
gccggcgtcg atgcggtatt tcacaacggc gccaaggccg gcgcctgggg cagctatgac 240
agctaccacc aggccaacgt ggtcggcacc gacaacgtga tcgccgcctg ccgcgcgcac 300
ggcatcagcc ggctggtcta cacctccacg cccagcgtga cccaccgcgc gacccacccg 360
gtggaaggcc tgggggctga tgaggtgccg tacggcgagg acttccaggc gccgtatgcg 420
gcgaccaagg cgattgccga acagcgcgtg ctggccgcca acgatgccac gctggcgacg 480
gtggcgctgc gcccgcgcct gatctggggc ccgggcgatc agcaactggt gccacgcctg 540
gcagaacgtg cgcggcaggg ccgcctgcgt ctggtgggcg atggcaacaa caaggtggat 600
accacttaca tcgacaacgc cgcgctcgcg catttcctcg ccttcgaagc gttggcaccg 660
ggtgccgcgt gtgcgggcaa ggcctacttc atttccaacg gcgaaccgct gcccatgcgc 720
gagctggtca acaagctgct ggccgcggtt ggcgcgccga cggtggacaa ggcgatcagt 780
ttcaagaccg cctatcgcat cggtgcggtc tgcgagcggc tgtggccgct gctgcgcctg 840
cgtggcgagc cgccgctgac ccgcttcctg gccgagcagc tgtgcacgcc gcactggtac 900
agcatggagc cggcgcgccg tgacttcggc tacgtgccgc aggtcagcat tgaagaaggg 960
ctgcgcaggc tgaaggcttc atctgccgca tag 993

<210> SEQ ID NO 8
<211> LENGTH: 330
<212> TYPE: PRT
<213> ORGANISM: Stenotrophomonas maltophilia

<400> SEQUENCE: 8

Met Lys Ile Leu Val Thr Gly Gly Gly Gly Phe Leu Gly Gln Ala Leu
1 5 10 15

Cys Arg Gly Leu Val Glu Arg Gly His Gln Val Leu Ala Phe Asn Arg
20 25 30

Ser His Tyr Pro Glu Leu Gln Ala Met Gly Val Gly Gln Ile Arg Gly
35 40 45

Asp Leu Ala Asp Ala Gln Ala Val Leu His Ala Val Ala Gly Val Asp
50 55 60

Ala Val Phe His Asn Gly Ala Lys Ala Gly Ala Trp Gly Ser Tyr Asp
65 70 75 80

Ser Tyr His Gln Ala Asn Val Val Gly Thr Asp Asn Val Ile Ala Ala
85 90 95

Cys Arg Ala His Gly Ile Ser Arg Leu Val Tyr Thr Ser Thr Pro Ser
100 105 110

Val Thr His Arg Ala Thr His Pro Val Glu Gly Leu Gly Ala Asp Glu
115 120 125

Val Pro Tyr Gly Glu Asp Phe Gln Ala Pro Tyr Ala Ala Thr Lys Ala

```
    130                 135                 140

Ile Ala Glu Gln Arg Val Leu Ala Ala Asn Asp Ala Thr Leu Ala Thr
145                 150                 155                 160

Val Ala Leu Arg Pro Arg Leu Ile Trp Gly Pro Gly Asp Gln Gln Leu
                165                 170                 175

Val Pro Arg Leu Ala Glu Arg Ala Arg Gln Gly Arg Leu Arg Leu Val
            180                 185                 190

Gly Asp Gly Asn Asn Lys Val Asp Thr Thr Tyr Ile Asp Asn Ala Ala
        195                 200                 205

Leu Ala His Phe Leu Ala Phe Glu Ala Leu Ala Pro Gly Ala Ala Cys
    210                 215                 220

Ala Gly Lys Ala Tyr Phe Ile Ser Asn Gly Glu Pro Leu Pro Met Arg
225                 230                 235                 240

Glu Leu Val Asn Lys Leu Leu Ala Ala Val Gly Ala Pro Thr Val Asp
                245                 250                 255

Lys Ala Ile Ser Phe Lys Thr Ala Tyr Arg Ile Gly Ala Val Cys Glu
            260                 265                 270

Arg Leu Trp Pro Leu Leu Arg Leu Arg Gly Glu Pro Pro Leu Thr Arg
        275                 280                 285

Phe Leu Ala Glu Gln Leu Cys Thr Pro His Trp Tyr Ser Met Glu Pro
    290                 295                 300

Ala Arg Arg Asp Phe Gly Tyr Val Pro Gln Val Ser Ile Glu Glu Gly
305                 310                 315                 320

Leu Arg Arg Leu Lys Ala Ser Ser Ala Ala
                325                 330
```

<210> SEQ ID NO 9
<211> LENGTH: 891
<212> TYPE: DNA
<213> ORGANISM: Stenotrophomonas maltophilia

<400> SEQUENCE: 9

```
atgtcccagc ttcccggtta ccccgcccac ccgcagcgct tcgaggtacg ccccggcctg      60

tcgatgaact atctcgacga aggcccgcgc gatggcgaag tggtggtgat ggtgcacggc     120

aacccgtcgt ggagctatta ctggcgcacg ctggtcgccg gcctgtcgga cacgtaccgc     180

tgcatcgtgc cggaccacat cggcatgggc ctgtcggaca agcccgatga cagccgctac     240

gagtacacgc tgcagtcgcg cgttgacgac ctcgatgcgc tgctcaagca tctgggcata     300

accggcccgg tgaccctggc ggtgcacgac tggggcggca tgatcggttt cggctgggcg     360

ctgtcgcacc acgaccaggt caagcgcctg gtggtgctca ataccgctgc attcccgatg     420

ccggcggcga agaagatgcc gtggcagatc gcgctgggcc gccactggaa gatcggcgag     480

tggatcatcc gcaccttcaa cgcgttctcc tccggtgcct cgtggctggg cgtggagcgg     540

aagatgccgg ccgacgtgcg ccgcgcctac gtgtcgccgt acaacagctg ggccaaccgc     600

atcagcacca tccgcttcat gcaggacatc ccgctgtcgc cggccgacaa ggcgtggtcg     660

ctgctggagc atgccggcaa ggcgctgccg tcgttcgccg accggccggc cttcctcggc     720

tggggcctgc gcgacttcgt gttcgaccac cacttcctga agggcttcca ggccgcgctg     780

ccgcaggccc aggtacatgc gttcgaggac gccggccact acgtgctgga agacaagcac     840

gaagtgctgg tgccggaaat ccgcgcgttc ctggacaaga acccgatctg a              891
```

<210> SEQ ID NO 10
<211> LENGTH: 296
<212> TYPE: PRT

<213> ORGANISM: Stenotrophomonas maltophilia

<400> SEQUENCE: 10

```
Met Ser Gln Leu Pro Gly Tyr Pro Ala His Pro Gln Arg Phe Glu Val
1               5                   10                  15

Arg Pro Gly Leu Ser Met Asn Tyr Leu Asp Glu Gly Pro Arg Asp Gly
            20                  25                  30

Glu Val Val Val Met Val His Gly Asn Pro Ser Trp Ser Tyr Tyr Trp
        35                  40                  45

Arg Thr Leu Val Ala Gly Leu Ser Asp Thr Tyr Arg Cys Ile Val Pro
    50                  55                  60

Asp His Ile Gly Met Gly Leu Ser Asp Lys Pro Asp Asp Ser Arg Tyr
65                  70                  75                  80

Glu Tyr Thr Leu Gln Ser Arg Val Asp Asp Leu Asp Ala Leu Leu Lys
                85                  90                  95

His Leu Gly Ile Thr Gly Pro Val Thr Leu Ala Val His Asp Trp Gly
            100                 105                 110

Gly Met Ile Gly Phe Gly Trp Ala Leu Ser His His Asp Gln Val Lys
        115                 120                 125

Arg Leu Val Val Leu Asn Thr Ala Ala Phe Pro Met Pro Ala Ala Lys
    130                 135                 140

Lys Met Pro Trp Gln Ile Ala Leu Gly Arg His Trp Lys Ile Gly Glu
145                 150                 155                 160

Trp Ile Ile Arg Thr Phe Asn Ala Phe Ser Ser Gly Ala Ser Trp Leu
                165                 170                 175

Gly Val Glu Arg Lys Met Pro Ala Asp Val Arg Arg Ala Tyr Val Ser
            180                 185                 190

Pro Tyr Asn Ser Trp Ala Asn Arg Ile Ser Thr Ile Arg Phe Met Gln
        195                 200                 205

Asp Ile Pro Leu Ser Pro Ala Asp Lys Ala Trp Ser Leu Leu Glu His
    210                 215                 220

Ala Gly Lys Ala Leu Pro Ser Phe Ala Asp Arg Pro Ala Phe Leu Gly
225                 230                 235                 240

Trp Gly Leu Arg Asp Phe Val Phe Asp His His Phe Leu Lys Gly Phe
                245                 250                 255

Gln Ala Ala Leu Pro Gln Ala Gln Val His Ala Phe Glu Asp Ala Gly
            260                 265                 270

His Tyr Val Leu Glu Asp Lys His Glu Val Leu Val Pro Glu Ile Arg
        275                 280                 285

Ala Phe Leu Asp Lys Asn Pro Ile
    290                 295
```

<210> SEQ ID NO 11
<211> LENGTH: 1017
<212> TYPE: DNA
<213> ORGANISM: Xanthomonas axonopodis

<400> SEQUENCE: 11

```
atgttatttc agaatgtttc tatcgcaggc ctggcccacg ttgatgctcc gcacactctg      60

accagcaaag aaattaacga acgtctgcag ccgacttacg accgtctggg catcaagacc     120

gacgttctgg gtgacgtagc tggtatccac gcgcgtcgtc tgtgggacca ggatgttcag     180

gcgagcgacg cggctaccca ggcagctcgt aaagcactga tcgacgctgg tatcggcatc     240

gagaagatcg gtctgctggt taacacgagc gtttcccgtg actatctgga gccgtccacg     300

gcgtccatcg ttagcggcaa cctgggcgta ggcgaccact gcgttacctt tgacgttgct     360
```

```
aacgcatgtc tggcattcat caacggcatg gatatcgctg ctcgtatgct ggaacgtggc    420

gagatcgatt acgccctggt agttgatggc gagacggcga acctggtgta tgagaaaacc    480

ctggagcgca tgacttcccc ggacgttact gaagaagagt tccgtaacga actggccgcg    540

ctgaccctgg gctgcggtgc ggctgcgatg gttatggcgc gtaccgagct ggtcccggat    600

gcgccgcgtt acaaaggtgg tgttacccgt agcgcaacgg agtggaacaa actgtgccgt    660

ggtaacctgg accgcatggt aactgacacc cgtctgctgc tgatcgaggg catcaaactg    720

gctcagaaaa ccttcatggc agctcgccaa gtcctgggtt gggctgttga tgaactggat    780

cagtttgtga tccatcaggt ttcccgtccg cacacggctg ctttcgttaa atcctttggt    840

attgatccgg ctaaagtgat gactatcttc ggcgaacacg gcaacatcgg tccggcctct    900

gttccgattg ttctgtctaa actgaaagaa ctgggtcgtc tgaagaaagg tgatcgtatc    960

gcgctgctgg gcatcggcag cggcctgaac tgcagcatgg ccgaagtggt ttggtaa      1017


<210> SEQ ID NO 12
<211> LENGTH: 338
<212> TYPE: PRT
<213> ORGANISM: Xanthomonas axonopodis

<400> SEQUENCE: 12

Met Leu Phe Gln Asn Val Ser Ile Ala Gly Leu Ala His Val Asp Ala
1               5                   10                  15

Pro His Thr Leu Thr Ser Lys Glu Ile Asn Glu Arg Leu Gln Pro Thr
            20                  25                  30

Tyr Asp Arg Leu Gly Ile Lys Thr Asp Val Leu Gly Asp Val Ala Gly
        35                  40                  45

Ile His Ala Arg Arg Leu Trp Asp Gln Asp Val Gln Ala Ser Asp Ala
    50                  55                  60

Ala Thr Gln Ala Ala Arg Lys Ala Leu Ile Asp Ala Gly Ile Gly Ile
65                  70                  75                  80

Glu Lys Ile Gly Leu Leu Val Asn Thr Ser Val Ser Arg Asp Tyr Leu
                85                  90                  95

Glu Pro Ser Thr Ala Ser Ile Val Ser Gly Asn Leu Gly Val Gly Asp
            100                 105                 110

His Cys Val Thr Phe Asp Val Ala Asn Ala Cys Leu Ala Phe Ile Asn
        115                 120                 125

Gly Met Asp Ile Ala Ala Arg Met Leu Glu Arg Gly Glu Ile Asp Tyr
    130                 135                 140

Ala Leu Val Val Asp Gly Glu Thr Ala Asn Leu Val Tyr Glu Lys Thr
145                 150                 155                 160

Leu Glu Arg Met Thr Ser Pro Asp Val Thr Glu Glu Glu Phe Arg Asn
                165                 170                 175

Glu Leu Ala Ala Leu Thr Leu Gly Cys Gly Ala Ala Ala Met Val Met
            180                 185                 190

Ala Arg Thr Glu Leu Val Pro Asp Ala Pro Arg Tyr Lys Gly Gly Val
        195                 200                 205

Thr Arg Ser Ala Thr Glu Trp Asn Lys Leu Cys Arg Gly Asn Leu Asp
    210                 215                 220

Arg Met Val Thr Asp Thr Arg Leu Leu Leu Ile Glu Gly Ile Lys Leu
225                 230                 235                 240

Ala Gln Lys Thr Phe Met Ala Ala Arg Gln Val Leu Gly Trp Ala Val
                245                 250                 255

Asp Glu Leu Asp Gln Phe Val Ile His Gln Val Ser Arg Pro His Thr
```

-continued

```
            260                 265                 270

Ala Ala Phe Val Lys Ser Phe Gly Ile Asp Pro Ala Lys Val Met Thr
        275                 280                 285

Ile Phe Gly Glu His Gly Asn Ile Gly Pro Ala Ser Val Pro Ile Val
    290                 295                 300

Leu Ser Lys Leu Lys Glu Leu Gly Arg Leu Lys Lys Gly Asp Arg Ile
305                 310                 315                 320

Ala Leu Leu Gly Ile Gly Ser Gly Leu Asn Cys Ser Met Ala Glu Val
                325                 330                 335

Val Trp


<210> SEQ ID NO 13
<211> LENGTH: 1680
<212> TYPE: DNA
<213> ORGANISM: Xanthomonas axonopodis

<400> SEQUENCE: 13

atggctacta ctctgtgtaa tattgctgct actctgcctc aactggctcg tgagcgcccg      60

gaccaaatcg ctatccgttg tccgggcggt cgcggcgcaa acggctttgc agcttatgac     120

gttaccctgt cttacgctga gctggacgca cgctctgatg ccatcgcggc tggtctggct     180

cgtcacggta ttggtcgcgg tgctcgcgca gtggtaatgg ttcgcccgag cccggagttc     240

ttcctgctga tgtttgctct gttcaaagct ggtgcagtgc cggttctggt tgatccgggt     300

atcgacaaac gcgcgctgaa gcagtgtctg gacgaagccc agccgcaggc gttcattggc     360

attgcgctgg cgcagctggc tcgccgtctg ctgcgctggg cccgtagcgc cacccagatt     420

gtcactgtag gcggccgtta tggctggggc ggtgttactc tggcgcgtgt agagcgtgat     480

ggtgccggtg ctggttccca gctggctgat acggcgccag acgatgttgc cgcaatcctg     540

ttcacgtccg gttccactgg tgtaccaaag ggcgtagtct accgtcaccg tcactttgtg     600

ggccagatcg agctgctgcg caacgcgttt ggtatgcagc ctggcggcgt agatctgccg     660

actttcccgc cgttcgccct gttcgatcca gcactgggtc tgacctctgt gattccagat     720

atggacccaa cccgccctgg ctccgcggac ccgcgcaaac tgcatgacgc tatcaaccgt     780

ttcggcgtta cccaactgtt cggttctccg gcgctgatgc gtgtactggc agactacggt     840

cagccgctgc cgaacgtccg tctggcgacg tccgcgggtg ctccggttcc gccggatgtt     900

gtggctaaaa tccgtgcgct gctgcctgcg gatgctcagt tttggactcc gtatggtgcc     960

accgagtgtc tgccggttgc agcaatcgag ggccgtacgc tggacgctac tcgtgcagcg    1020

accgaggccg gcgcaggcac ctgtgtcggt cacgttgtac cgccgaacca ggtacgtatt    1080

atcgcaattg acgatgcggc aatcgcagac tggagcggtg tccgtgagct ggcaaccggt    1140

gaagttggcg agatcacggt agccggccct acggcgaccg acacctactt taaccgcgac    1200

gcagcaactc gtattgcaaa aatccgcgag tgctgctctg acggctctga gcgtgtcgta    1260

caccgtatgg gcgatgttgg ctacgtcgac gctgaaggcc gtctgtggtt ctgtggtcgc    1320

aagacccacc gtgtagaggc cgcctctggc ccgctgtaca ccgagcaggt cgaaccggtc    1380

ttcaacgtac accgccaggt ccgtcgcact gccctggttg gtgttggcgc acctggtcaa    1440

cagcaaccgg ttctgtgcgt ggaactgcag ccaggcgtat ctgcgtctgc tttcgcacag    1500

gtagagtccg atctgcgtgc actgggcgcc gctcacccgc ataccgcggg tgttgcgcgc    1560

ttcctgcgtc attctggctt ccctgtcgac atccgtcaca acgccaaaat cggccgtgaa    1620

accctggctg tttgggcggc tcagcaactg cacaagcgtg gcaagcttgc ggccgcataa    1680
```

<210> SEQ ID NO 14
<211> LENGTH: 559
<212> TYPE: PRT
<213> ORGANISM: Xanthomonas axonopodis

<400> SEQUENCE: 14

```
Met Ala Thr Thr Leu Cys Asn Ile Ala Ala Thr Leu Pro Gln Leu Ala
1               5                   10                  15

Arg Glu Arg Pro Asp Gln Ile Ala Ile Arg Cys Pro Gly Gly Arg Gly
            20                  25                  30

Ala Asn Gly Phe Ala Ala Tyr Asp Val Thr Leu Ser Tyr Ala Glu Leu
        35                  40                  45

Asp Ala Arg Ser Asp Ala Ile Ala Ala Gly Leu Ala Arg His Gly Ile
    50                  55                  60

Gly Arg Gly Ala Arg Ala Val Val Met Val Arg Pro Ser Pro Glu Phe
65                  70                  75                  80

Phe Leu Leu Met Phe Ala Leu Phe Lys Ala Gly Ala Val Pro Val Leu
                85                  90                  95

Val Asp Pro Gly Ile Asp Lys Arg Ala Leu Lys Gln Cys Leu Asp Glu
            100                 105                 110

Ala Gln Pro Gln Ala Phe Ile Gly Ile Ala Leu Ala Gln Leu Ala Arg
        115                 120                 125

Arg Leu Leu Arg Trp Ala Arg Ser Ala Thr Gln Ile Val Thr Val Gly
    130                 135                 140

Gly Arg Tyr Gly Trp Gly Gly Val Thr Leu Ala Arg Val Glu Arg Asp
145                 150                 155                 160

Gly Ala Gly Ala Gly Ser Gln Leu Ala Asp Thr Ala Pro Asp Asp Val
                165                 170                 175

Ala Ala Ile Leu Phe Thr Ser Gly Ser Thr Gly Val Pro Lys Gly Val
            180                 185                 190

Val Tyr Arg His Arg His Phe Val Gly Gln Ile Glu Leu Leu Arg Asn
        195                 200                 205

Ala Phe Gly Met Gln Pro Gly Gly Val Asp Leu Pro Thr Phe Pro Pro
    210                 215                 220

Phe Ala Leu Phe Asp Pro Ala Leu Gly Leu Thr Ser Val Ile Pro Asp
225                 230                 235                 240

Met Asp Pro Thr Arg Pro Gly Ser Ala Asp Pro Arg Lys Leu His Asp
                245                 250                 255

Ala Ile Asn Arg Phe Gly Val Thr Gln Leu Phe Gly Ser Pro Ala Leu
            260                 265                 270

Met Arg Val Leu Ala Asp Tyr Gly Gln Pro Leu Pro Asn Val Arg Leu
        275                 280                 285

Ala Thr Ser Ala Gly Ala Pro Val Pro Pro Asp Val Val Ala Lys Ile
    290                 295                 300

Arg Ala Leu Leu Pro Ala Asp Ala Gln Phe Trp Thr Pro Tyr Gly Ala
305                 310                 315                 320

Thr Glu Cys Leu Pro Val Ala Ala Ile Glu Gly Arg Thr Leu Asp Ala
                325                 330                 335

Thr Arg Ala Ala Thr Glu Ala Gly Ala Gly Thr Cys Val Gly His Val
            340                 345                 350

Val Pro Pro Asn Gln Val Arg Ile Ile Ala Ile Asp Asp Ala Ala Ile
        355                 360                 365

Ala Asp Trp Ser Gly Val Arg Glu Leu Ala Thr Gly Glu Val Gly Glu
    370                 375                 380
```

```
Ile Thr Val Ala Gly Pro Thr Ala Thr Asp Thr Tyr Phe Asn Arg Asp
385                 390                 395                 400

Ala Ala Thr Arg Ile Ala Lys Ile Arg Glu Cys Cys Ser Asp Gly Ser
                405                 410                 415

Glu Arg Val Val His Arg Met Gly Asp Val Gly Tyr Val Asp Ala Glu
            420                 425                 430

Gly Arg Leu Trp Phe Cys Gly Arg Lys Thr His Arg Val Glu Ala Ala
        435                 440                 445

Ser Gly Pro Leu Tyr Thr Glu Gln Val Glu Pro Val Phe Asn Val His
    450                 455                 460

Arg Gln Val Arg Arg Thr Ala Leu Val Gly Val Gly Ala Pro Gly Gln
465                 470                 475                 480

Gln Gln Pro Val Leu Cys Val Glu Leu Gln Pro Gly Val Ser Ala Ser
                485                 490                 495

Ala Phe Ala Gln Val Glu Ser Asp Leu Arg Ala Leu Gly Ala Ala His
            500                 505                 510

Pro His Thr Ala Gly Val Ala Arg Phe Leu Arg His Ser Gly Phe Pro
        515                 520                 525

Val Asp Ile Arg His Asn Ala Lys Ile Gly Arg Glu Thr Leu Ala Val
    530                 535                 540

Trp Ala Ala Gln Gln Leu His Lys Arg Gly Lys Leu Ala Ala Ala
545                 550                 555
```

<210> SEQ ID NO 15
<211> LENGTH: 1029
<212> TYPE: DNA
<213> ORGANISM: Xanthomonas axonopodis

<400> SEQUENCE: 15

```
atggctaaag tactggttac cggtggtggt ggttttctgg gtcaagcact gtgccgtggt     60

ctgcgcgcac gtggtcacga ggttgtttct tttcagcgtg gtgactaccc ggtactgcaa    120

cgtctgggtg ttggccagat tcgtggcgac ctggccgatc cgcaggcggt gcgtcacgca    180

tttgccggca ttgatgcagt cttccacaac gcggcaaaag cgggtgcgtg gggttcctat    240

gatagctacc accaagccaa cgtagttggt actcaaaacg tgatcgaagc atgtcgcgca    300

aacggcgttc cgcgtctgat ctacacctcc accccgtccg taactcatcg tgcgaccaac    360

ccagtagagg gtctgggcgc ggatgaggtt ccgtatggtg atgacctgcg tgcggcgtac    420

gcagctacta aagccatcgc ggaacgtgct gtactggcgg caaacgacgc tcagctggca    480

accgtagcgc tgcgtccgcg cctgatctgg ggtccgggcg ataaccatct gctgccacgt    540

ctggctgccc gtgcacgcgc gggccgtctg cgtatggttg gtgatggtgg caacctggta    600

gactctacct atatcgataa cgcggcgcag gcgcacttcg atgcgtttga acatctggcg    660

gttggtgctg cctgcgctgg ccgtgcttac tttatctcca acggcgaacc gctgccgatg    720

cgtgaactgc tgaaccgtct gctggcggct gtcgatgcgc cggcagtcac ctgcagcctg    780

tctttcaaca ctgcataccg tattggtgct gtttgtgaga cgctgtggcc tctgctgcgc    840

ctgccgggtg aggtaccgct gactcgtttc ctggttgaac agctgtgtac tccgcactgg    900

tactctatgg aaccggcccg tcgcgatttc ggctatgtac cgcgcatctc tatcgaggag    960

ggtctgcagc gtctgcgttc ttctagctcc aacgatatcg ccattactcg taagcttgcg   1020

gccgcataa                                                           1029
```

<210> SEQ ID NO 16
<211> LENGTH: 342

<212> TYPE: PRT
<213> ORGANISM: Xanthomonas axonopodis

<400> SEQUENCE: 16

```
Met Ala Lys Val Leu Val Thr Gly Gly Gly Gly Phe Leu Gly Gln Ala
1               5                   10                  15

Leu Cys Arg Gly Leu Arg Ala Arg Gly His Glu Val Val Ser Phe Gln
            20                  25                  30

Arg Gly Asp Tyr Pro Val Leu Gln Arg Leu Gly Val Gly Gln Ile Arg
        35                  40                  45

Gly Asp Leu Ala Asp Pro Gln Ala Val Arg His Ala Phe Ala Gly Ile
    50                  55                  60

Asp Ala Val Phe His Asn Ala Ala Lys Ala Gly Ala Trp Gly Ser Tyr
65                  70                  75                  80

Asp Ser Tyr His Gln Ala Asn Val Val Gly Thr Gln Asn Val Ile Glu
                85                  90                  95

Ala Cys Arg Ala Asn Gly Val Pro Arg Leu Ile Tyr Thr Ser Thr Pro
            100                 105                 110

Ser Val Thr His Arg Ala Thr Asn Pro Val Glu Gly Leu Gly Ala Asp
        115                 120                 125

Glu Val Pro Tyr Gly Asp Asp Leu Arg Ala Ala Tyr Ala Ala Thr Lys
    130                 135                 140

Ala Ile Ala Glu Arg Ala Val Leu Ala Ala Asn Asp Ala Gln Leu Ala
145                 150                 155                 160

Thr Val Ala Leu Arg Pro Arg Leu Ile Trp Gly Pro Gly Asp Asn His
                165                 170                 175

Leu Leu Pro Arg Leu Ala Ala Arg Ala Arg Ala Gly Arg Leu Arg Met
            180                 185                 190

Val Gly Asp Gly Gly Asn Leu Val Asp Ser Thr Tyr Ile Asp Asn Ala
        195                 200                 205

Ala Gln Ala His Phe Asp Ala Phe Glu His Leu Ala Val Gly Ala Ala
    210                 215                 220

Cys Ala Gly Arg Ala Tyr Phe Ile Ser Asn Gly Glu Pro Leu Pro Met
225                 230                 235                 240

Arg Glu Leu Leu Asn Arg Leu Leu Ala Ala Val Asp Ala Pro Ala Val
                245                 250                 255

Thr Cys Ser Leu Ser Phe Asn Thr Ala Tyr Arg Ile Gly Ala Val Cys
            260                 265                 270

Glu Thr Leu Trp Pro Leu Leu Arg Leu Pro Gly Glu Val Pro Leu Thr
        275                 280                 285

Arg Phe Leu Val Glu Gln Leu Cys Thr Pro His Trp Tyr Ser Met Glu
    290                 295                 300

Pro Ala Arg Arg Asp Phe Gly Tyr Val Pro Arg Ile Ser Ile Glu Glu
305                 310                 315                 320

Gly Leu Gln Arg Leu Arg Ser Ser Ser Ser Asn Asp Ile Ala Ile Thr
                325                 330                 335

Arg Lys Leu Ala Ala Ala
            340
```

<210> SEQ ID NO 17
<211> LENGTH: 1020
<212> TYPE: DNA
<213> ORGANISM: Chloroflexus aggregans

<400> SEQUENCE: 17

```
atgttattca agcacgtcat gatcgaagct gtttcctacg tactggcacc tcatcgtatc      60
```

-continued

```
acctctgcgt ggatcgaaga ccagatcgca gagacgatgg agcgcctgcg tttcccgcgt    120

ggcaaactgg aggctctgtc tggcattcgt gagcgccgct tctgggacga aggcaccctg    180

ccgtctactg ttgctacgat ggctgctgaa cagctgctgc aacaagtatc tgttgatcgt    240

gaccgcattg gcctgctgat caacacctcc gtatgtcagg attacctgga gccgtccact    300

gcatgttttg tgcaccgcaa cctgggtctg tctccgcgtg cgatcaattt tgatgtgcgt    360

aacgcttgcc tgggcttcct gaatggtatg gcgatcgcag gtatgatgat tgaggcgggc    420

actatcgagt atgccctgat cgttgacggc gaaggctccc aggatgcggt gatggcgact    480

atccgccgtc tgcgtcgtcc ggagactacc aaacaggacc tgcgtgacaa cttcgcaacg    540

ctgactctgg gctctggtgg tgcggcgatg ctgctgaccc atgaatgtct gagccgttct    600

ggtcaccgtc tgaacggcgt agttaccctg gcagccaccc agtataacca cctgtgtctg    660

ggccagcctg actacatgaa aactgatgct ggcgccctga tgcacgcggg tgttgagctg    720

gcaaccgcga cctggcgcct ggcgcaagaa accctgccga actggagcga tcgtcagatc    780

gctctgtacg ctccacatca ggttggcgca cgtcacatgg cggctgtaac gaaggcgctg    840

ggcatcactc cgagcaaact gttcctgaac ttcccgaccc tgggcaatat tggtccggct    900

gctctgccga ttagcctggc ccaggcggtt gaagcgggtc gcctgcgtcc gggtgaccac    960

gtaggcctgc tgggtatcgg ttccggtctg aattgctcta tgatgtccgt tacgtggtaa   1020
```

<210> SEQ ID NO 18
<211> LENGTH: 339
<212> TYPE: PRT
<213> ORGANISM: Chloroflexus aggregans

<400> SEQUENCE: 18

```
Met Leu Phe Lys His Val Met Ile Glu Ala Val Ser Tyr Val Leu Ala
1               5                   10                  15

Pro His Arg Ile Thr Ser Ala Trp Ile Glu Asp Gln Ile Ala Glu Thr
            20                  25                  30

Met Glu Arg Leu Arg Phe Pro Arg Gly Lys Leu Glu Ala Leu Ser Gly
        35                  40                  45

Ile Arg Glu Arg Arg Phe Trp Asp Glu Gly Thr Leu Pro Ser Thr Val
    50                  55                  60

Ala Thr Met Ala Ala Glu Gln Leu Leu Gln Gln Val Ser Val Asp Arg
65                  70                  75                  80

Asp Arg Ile Gly Leu Leu Ile Asn Thr Ser Val Cys Gln Asp Tyr Leu
                85                  90                  95

Glu Pro Ser Thr Ala Cys Phe Val His Arg Asn Leu Gly Leu Ser Pro
            100                 105                 110

Arg Ala Ile Asn Phe Asp Val Arg Asn Ala Cys Leu Gly Phe Leu Asn
        115                 120                 125

Gly Met Ala Ile Ala Gly Met Met Ile Glu Ala Gly Thr Ile Glu Tyr
    130                 135                 140

Ala Leu Ile Val Asp Gly Glu Gly Ser Gln Asp Ala Val Met Ala Thr
145                 150                 155                 160

Ile Arg Arg Leu Arg Arg Pro Glu Thr Thr Lys Gln Asp Leu Arg Asp
                165                 170                 175

Asn Phe Ala Thr Leu Thr Leu Gly Ser Gly Gly Ala Ala Met Leu Leu
            180                 185                 190

Thr His Glu Cys Leu Ser Arg Ser Gly His Arg Leu Asn Gly Val Val
        195                 200                 205
```

```
Thr Leu Ala Ala Thr Gln Tyr Asn His Leu Cys Leu Gly Gln Pro Asp
    210                 215                 220

Tyr Met Lys Thr Asp Ala Gly Ala Leu Met His Ala Gly Val Glu Leu
225                 230                 235                 240

Ala Thr Ala Thr Trp Arg Leu Ala Gln Glu Thr Leu Pro Asn Trp Ser
                245                 250                 255

Asp Arg Gln Ile Ala Leu Tyr Ala Pro His Gln Val Gly Ala Arg His
            260                 265                 270

Met Ala Ala Val Thr Lys Ala Leu Gly Ile Thr Pro Ser Lys Leu Phe
        275                 280                 285

Leu Asn Phe Pro Thr Leu Gly Asn Ile Gly Pro Ala Ala Leu Pro Ile
    290                 295                 300

Ser Leu Ala Gln Ala Val Glu Ala Gly Arg Leu Arg Pro Gly Asp His
305                 310                 315                 320

Val Gly Leu Leu Gly Ile Gly Ser Gly Leu Asn Cys Ser Met Met Ser
                325                 330                 335

Val Thr Trp


<210> SEQ ID NO 19
<211> LENGTH: 1695
<212> TYPE: DNA
<213> ORGANISM: Chloroflexus aggregans

<400> SEQUENCE: 19

atgagagatc tgtctcaacg tggtggtact gaagtatggc cagcagttgc tggtgctaat      60

gttgctcgtt atctgccgtg gatggcacag cacatgccaa cccagaccgc gattatcacc     120

ggcgtcggcc gcgaccgttc cggtaaagtg atttatcgcc gtcagtcctt cgctggcctg     180

aacaccgctt ctgatcgcct ggcgtggggt ctgaccgcct acggtttccg tccgggtatg     240

cgtgtgctgc tgatggtgcc ggcaggtgag ccactgatcc gcctgacgtt cgctctgctg     300

aaagcgggtt gtgtgccgat tctgattgac ccagcgatgg gccgtcgtaa cctggctcag     360

tgcattgcgg aatctgcacc ggaagctctg gtcggcgtac cacgtgcgca cctgctgcgt     420

ctgatcttcc cgcgtgcctg tgctaccatt aaacacgctg tttctgtggg tcctgctctg     480

ccgggtgtgg ccgccctgca cgaactggag gttaccgtga acgcaccgtt cgcgctggca     540

gaggttgctc cgaccgatcc ggctgcgatc gttttcacct ctggctccac tggcaccccg     600

aaaggcgtgc tgtacaccca cggtatgttc gaagctcaga tccatgtact gcgtgagctg     660

ttcggtatcg aaccgggtga aatcgaaatg ccggcgttcc cactgttcgc actgttcaac     720

gtagctctgg gtgttacctc tgcgatcccg ccgatcgacc cgactcgtcc ggcacagtgc     780

gatccagcgg cggtagttga gtttatccgt gatctgggtg taacttccac cttcggctcc     840

cctgcgattt gggaaaaagt gacggcgtat tgcctggagc acggcatgca gctgccatct     900

ctgcgtcgtg ttctgatggc tggcgcccct gttccggcat acctgcacga gcgtctgcat     960

cagatcctga ttcctccggc ggacagcttc accccgtacg gcgcgactga ggcgctgccg    1020

gtcacctcta ttagcggtcg tgaggtactg gcagcgcgct cccagtaccc ttctccgatg    1080

gctggcacct gcgttggtta tccggttcca aaggtaaaag tggctatcat cccgatctct    1140

gatgagccga tccaggcttg gtctgatatc cgtccgctgc caccgggtgt agttggtgaa    1200

atttgcgttt ccggtccggc ggttacgcgt gagtatgtcg gccgtccaca ggcaaccgtc    1260

ctggcaaaaa tcgcggatgg tgaccaggtg tggcatcgca tgggcgatct gggttatttc    1320

gatgagtacg gccgtctgtg gttttatggc cgcaaatccc agcgcgtaat cactgcgcac    1380
```

-continued

```
cgtaccctgt tcactgagcc ggtggagctg ctgttcaacc aacacccagc ggtggcccgc   1440

agcgctctgg tgggcgttgg ccctagcggc gcacagctgc cagtggtagt ggttgagcgt   1500

cgtccgcaga tcacgattgc gcctacccag ctgattgcgg aactgcgtca gctggcagcc   1560

accactgaga tgaccgcgtc catccatgat tttctgatcc atccggcttt cccggttgac   1620

atccgtcaca acgctaagat tttccgcgaa cagctggctg tgtgggctgc aaaacaactg   1680

cgtgttccgg gttaa                                                    1695


<210> SEQ ID NO 20
<211> LENGTH: 564
<212> TYPE: PRT
<213> ORGANISM: Chloroflexus aggregans

<400> SEQUENCE: 20

Met Arg Asp Leu Ser Gln Arg Gly Gly Thr Glu Val Trp Pro Ala Val
1               5                   10                  15

Ala Gly Ala Asn Val Ala Arg Tyr Leu Pro Trp Met Ala Gln His Met
            20                  25                  30

Pro Thr Gln Thr Ala Ile Ile Thr Gly Val Gly Arg Asp Arg Ser Gly
        35                  40                  45

Lys Val Ile Tyr Arg Arg Gln Ser Phe Ala Gly Leu Asn Thr Ala Ser
    50                  55                  60

Asp Arg Leu Ala Trp Gly Leu Thr Ala Tyr Gly Phe Arg Pro Gly Met
65                  70                  75                  80

Arg Val Leu Leu Met Val Pro Ala Gly Glu Pro Leu Ile Arg Leu Thr
                85                  90                  95

Phe Ala Leu Leu Lys Ala Gly Cys Val Pro Ile Leu Ile Asp Pro Ala
            100                 105                 110

Met Gly Arg Arg Asn Leu Ala Gln Cys Ile Ala Glu Ser Ala Pro Glu
        115                 120                 125

Ala Leu Val Gly Val Pro Arg Ala His Leu Leu Arg Leu Ile Phe Pro
    130                 135                 140

Arg Ala Cys Ala Thr Ile Lys His Ala Val Ser Val Gly Pro Ala Leu
145                 150                 155                 160

Pro Gly Val Ala Ala Leu His Glu Leu Glu Val Thr Val Asn Ala Pro
                165                 170                 175

Phe Ala Leu Ala Glu Val Ala Pro Thr Asp Pro Ala Ala Ile Val Phe
            180                 185                 190

Thr Ser Gly Ser Thr Gly Thr Pro Lys Gly Val Leu Tyr Thr His Gly
        195                 200                 205

Met Phe Glu Ala Gln Ile His Val Leu Arg Glu Leu Phe Gly Ile Glu
    210                 215                 220

Pro Gly Glu Ile Glu Met Pro Ala Phe Pro Leu Phe Ala Leu Phe Asn
225                 230                 235                 240

Val Ala Leu Gly Val Thr Ser Ala Ile Pro Pro Ile Asp Pro Thr Arg
                245                 250                 255

Pro Ala Gln Cys Asp Pro Ala Ala Val Val Glu Phe Ile Arg Asp Leu
            260                 265                 270

Gly Val Thr Ser Thr Phe Gly Ser Pro Ala Ile Trp Glu Lys Val Thr
        275                 280                 285

Ala Tyr Cys Leu Glu His Gly Met Gln Leu Pro Ser Leu Arg Arg Val
    290                 295                 300

Leu Met Ala Gly Ala Pro Val Pro Ala Tyr Leu His Glu Arg Leu His
305                 310                 315                 320
```

Gln Ile Leu Ile Pro Pro Ala Asp Ser Phe Thr Pro Tyr Gly Ala Thr
325 330 335

Glu Ala Leu Pro Val Thr Ser Ile Ser Gly Arg Glu Val Leu Ala Ala
340 345 350

Arg Ser Gln Tyr Pro Ser Pro Met Ala Gly Thr Cys Val Gly Tyr Pro
355 360 365

Val Pro Lys Val Lys Val Ala Ile Ile Pro Ile Ser Asp Glu Pro Ile
370 375 380

Gln Ala Trp Ser Asp Ile Arg Pro Leu Pro Pro Gly Val Val Gly Glu
385 390 395 400

Ile Cys Val Ser Gly Pro Ala Val Thr Arg Glu Tyr Val Gly Arg Pro
405 410 415

Gln Ala Thr Val Leu Ala Lys Ile Ala Asp Gly Asp Gln Val Trp His
420 425 430

Arg Met Gly Asp Leu Gly Tyr Phe Asp Glu Tyr Gly Arg Leu Trp Phe
435 440 445

Tyr Gly Arg Lys Ser Gln Arg Val Ile Thr Ala His Arg Thr Leu Phe
450 455 460

Thr Glu Pro Val Glu Leu Leu Phe Asn Gln His Pro Ala Val Ala Arg
465 470 475 480

Ser Ala Leu Val Gly Val Gly Pro Ser Gly Ala Gln Leu Pro Val Val
485 490 495

Val Val Glu Arg Arg Pro Gln Ile Thr Ile Ala Pro Thr Gln Leu Ile
500 505 510

Ala Glu Leu Arg Gln Leu Ala Ala Thr Thr Glu Met Thr Ala Ser Ile
515 520 525

His Asp Phe Leu Ile His Pro Ala Phe Pro Val Asp Ile Arg His Asn
530 535 540

Ala Lys Ile Phe Arg Glu Gln Leu Ala Val Trp Ala Ala Lys Gln Leu
545 550 555 560

Arg Val Pro Gly

<210> SEQ ID NO 21
<211> LENGTH: 990
<212> TYPE: DNA
<213> ORGANISM: Chloroflexus aggregans

<400> SEQUENCE: 21
atgatcgctc tggtaactgg tggtaatggt tttgttggcc gttatctggt cgaacagctg 60
gttgcgcgtg gtgaccacgt acgcgtagtg ggccgtggcg agtatccgga actgcaggca 120
ctgggtgtgg agactttctg tgccgacctg gcaacgccag aatctgctcc ggttctggcg 180
cgtgcaatgc gcggcgtgac tgccgtattc cacgtggctg ctaaagcggg tctgtggggt 240
cgttacgatg aattttaccg tgccaacgtt agcgctaccc agcgtgtgat gaaagcagct 300
ctgcgtgcgg gcgtaccgaa attcatttac acttccactc catccgttgt tatcggtatg 360
gacgacctgc acggtgttga cgagcagacc ccgtacccaa cccgttatct ggcgccgtat 420
ccgcagacta aagcgctggc cgagcgctac gtcctggcac agaccgagat cgcgactgtg 480
gcgctgcgcc cgcacctgat ttggggtccg cgtgacccgc acattctgcc gcgtctgctg 540
cgtcgtgcac gtcgtcgtat gctgttccaa atcggtgatg gtactaacct ggtggatgtg 600
tgttatgtgg aaaacgtcgc cgaagcgcac atcctggctg cagctgcgct ggacgatcgt 660
tctccgctgc gcggtcgcgc ttacttcatc ggccaggaac gcccggtgaa cctgtggcaa 720
ttcatcggcg aaattctgac gcacgctggt tgtccgccgg ttcgcggcaa actgccggct 780

```
accgtagcct atcagctggc gaccgttctg gagttcctgt acgccggcct gcgcctgccg    840

ggtgaaccgc cgctgacccg tctgatggtg cacgagctgt ctcactccca ttggttctcc    900

catgcggcag ctgagcgtga ttttggttac accccgcgta tcagcatcga ggagggcctg    960

cgtcgcactt tcgctcgtca ggccatgtaa                                     990


<210> SEQ ID NO 22
<211> LENGTH: 329
<212> TYPE: PRT
<213> ORGANISM: Chloroflexus aggregans

<400> SEQUENCE: 22

Met Ile Ala Leu Val Thr Gly Gly Asn Gly Phe Val Gly Arg Tyr Leu
1               5                   10                  15

Val Glu Gln Leu Val Ala Arg Gly Asp His Val Arg Val Val Gly Arg
            20                  25                  30

Gly Glu Tyr Pro Glu Leu Gln Ala Leu Gly Val Glu Thr Phe Cys Ala
        35                  40                  45

Asp Leu Ala Thr Pro Glu Ser Ala Pro Val Leu Ala Arg Ala Met Arg
    50                  55                  60

Gly Val Thr Ala Val Phe His Val Ala Ala Lys Ala Gly Leu Trp Gly
65                  70                  75                  80

Arg Tyr Asp Glu Phe Tyr Arg Ala Asn Val Ser Ala Thr Gln Arg Val
                85                  90                  95

Met Lys Ala Ala Leu Arg Ala Gly Val Pro Lys Phe Ile Tyr Thr Ser
            100                 105                 110

Thr Pro Ser Val Val Ile Gly Met Asp Asp Leu His Gly Val Asp Glu
        115                 120                 125

Gln Thr Pro Tyr Pro Thr Arg Tyr Leu Ala Pro Tyr Pro Gln Thr Lys
    130                 135                 140

Ala Leu Ala Glu Arg Tyr Val Leu Ala Gln Thr Glu Ile Ala Thr Val
145                 150                 155                 160

Ala Leu Arg Pro His Leu Ile Trp Gly Pro Arg Asp Pro His Ile Leu
                165                 170                 175

Pro Arg Leu Leu Arg Arg Ala Arg Arg Arg Met Leu Phe Gln Ile Gly
            180                 185                 190

Asp Gly Thr Asn Leu Val Asp Val Cys Tyr Val Glu Asn Val Ala Glu
        195                 200                 205

Ala His Ile Leu Ala Ala Ala Ala Leu Asp Asp Arg Ser Pro Leu Arg
    210                 215                 220

Gly Arg Ala Tyr Phe Ile Gly Gln Glu Arg Pro Val Asn Leu Trp Gln
225                 230                 235                 240

Phe Ile Gly Glu Ile Leu Thr His Ala Gly Cys Pro Pro Val Arg Gly
                245                 250                 255

Lys Leu Pro Ala Thr Val Ala Tyr Gln Leu Ala Thr Val Leu Glu Phe
            260                 265                 270

Leu Tyr Ala Gly Leu Arg Leu Pro Gly Glu Pro Pro Leu Thr Arg Leu
        275                 280                 285

Met Val His Glu Leu Ser His Ser His Trp Phe Ser His Ala Ala Ala
    290                 295                 300

Glu Arg Asp Phe Gly Tyr Thr Pro Arg Ile Ser Ile Glu Glu Gly Leu
305                 310                 315                 320

Arg Arg Thr Phe Ala Arg Gln Ala Met
                325
```

<210> SEQ ID NO 23
<211> LENGTH: 13
<212> TYPE: PRT
<213> ORGANISM: Artificial sequence
<220> FEATURE:
<223> OTHER INFORMATION: Peptide motifs used to identify OleA genes
<220> FEATURE:
<221> NAME/KEY: misc_feature
<222> LOCATION: (1)..(1)
<223> OTHER INFORMATION: Xaa can be Leu or Phe
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Ile, Val, Leu or Met
<220> FEATURE:
<221> NAME/KEY: misc_feature
<222> LOCATION: (5)..(5)
<223> OTHER INFORMATION: Xaa can be Ala, Thr, Ser or Val
<220> FEATURE:
<221> NAME/KEY: misc_feature
<222> LOCATION: (7)..(7)
<223> OTHER INFORMATION: Xaa can be Ile or Val
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be Glu, Ala, His or Ser
<220> FEATURE:
<221> NAME/KEY: misc_feature
<222> LOCATION: (12)..(12)
<223> OTHER INFORMATION: Xaa can be any naturally occurring amino acid

<400> SEQUENCE: 23

Xaa Xaa Xaa Xaa Xaa Gly Xaa Xaa Xaa Arg Arg Xaa Trp
1               5                   10

<210> SEQ ID NO 24
<211> LENGTH: 13
<212> TYPE: PRT
<213> ORGANISM: Artificial sequence
<220> FEATURE:
<223> OTHER INFORMATION: Peptide motifs used to identify OleA genes
<220> FEATURE:
<221> NAME/KEY: misc_feature
<222> LOCATION: (1)..(1)
<223> OTHER INFORMATION: Xaa can be Thr, Ala or Cys
<220> FEATURE:
<221> NAME/KEY: misc_feature
<222> LOCATION: (2)..(2)
<223> OTHER INFORMATION: Xaa can be Ser, Gly or Thr
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Arg or Gln
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be Ser or Ala
<220> FEATURE:
<221> NAME/KEY: misc_feature
<222> LOCATION: (12)..(12)
<223> OTHER INFORMATION: Xaa can be Thr or Val

<400> SEQUENCE: 24

```
Xaa Xaa Val Xaa Xaa Xaa Xaa Xaa Glu Pro Xaa Xaa Ala
1               5                   10
```

<210> SEQ ID NO 25
<211> LENGTH: 8
<212> TYPE: PRT
<213> ORGANISM: Artificial sequence
<220> FEATURE:
<223> OTHER INFORMATION: Peptide motifs used to identify OleA genes
<220> FEATURE:
<221> NAME/KEY: misc_feature
<222> LOCATION: (2)..(2)
<223> OTHER INFORMATION: Xaa can be Val, Ile or Leu
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be Ala or Gly

<400> SEQUENCE: 25

```
Asp Xaa Xaa Asn Ala Cys Leu Xaa
1               5
```

<210> SEQ ID NO 26
<211> LENGTH: 6
<212> TYPE: PRT
<213> ORGANISM: Artificial sequence
<220> FEATURE:
<223> OTHER INFORMATION: Peptide motifs used to identify OleA genes
<220> FEATURE:
<221> NAME/KEY: misc_feature
<222> LOCATION: (1)..(1)
<223> OTHER INFORMATION: Xaa can be Leu or Met
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any Ser, Cys or Ala

<400> SEQUENCE: 26

```
Xaa Thr Xaa Gly Xaa Gly
1               5
```

<210> SEQ ID NO 27
<211> LENGTH: 12
<212> TYPE: PRT
<213> ORGANISM: Artificial sequence
<220> FEATURE:
<223> OTHER INFORMATION: Peptide motifs used to identify OleA genes
<220> FEATURE:
<221> NAME/KEY: misc_feature
<222> LOCATION: (2)..(2)
<223> OTHER INFORMATION: Xaa can be any naturally occurring amino acid
<220> FEATURE:

<221> NAME/KEY: misc_feature
<222> LOCATION: (4)..(4)
<223> OTHER INFORMATION: Xaa can be Asp, Ser or Asn
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 27

Met Xaa Thr Xaa Xaa Xaa Xaa Xaa Xaa Xaa Xaa Gly
1               5                   10

<210> SEQ ID NO 28
<211> LENGTH: 25
<212> TYPE: PRT
<213> ORGANISM: Artificial sequence
<220> FEATURE:
<223> OTHER INFORMATION: Peptide motifs used to identify OleA genes
<220> FEATURE:
<221> NAME/KEY: misc_feature
<222> LOCATION: (1)..(1)
<223> OTHER INFORMATION: Xaa can be Leu or Phe
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Asp or Glu
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be Leu or Met
<220> FEATURE:
<221> NAME/KEY: misc_feature
<222> LOCATION: (12)..(12)
<223> OTHER INFORMATION: Xaa can be Ile, Val or Met
<220> FEATURE:
<221> NAME/KEY: misc_feature
<222> LOCATION: (16)..(16)
<223> OTHER INFORMATION: Xaa can be Leu or Ile
<220> FEATURE:
<221> NAME/KEY: misc_feature
<222> LOCATION: (18)..(18)
<223> OTHER INFORMATION: Xaa can be Cys, Ala, Thr or Ser
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any Met, Ala or Val
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 28

```
Xaa Xaa Xaa Gly Xaa Xaa Xaa Xaa Xaa Xaa Gly Xaa Gly Ser Gly Xaa
1               5                   10                  15

Asn Xaa Xaa Xaa Xaa Xaa Xaa Xaa Trp
            20                  25
```

<210> SEQ ID NO 29
<211> LENGTH: 28
<212> TYPE: DNA
<213> ORGANISM: Artificial sequence
<220> FEATURE:
<223> OTHER INFORMATION: Synthetic oligonucleotide primer

<400> SEQUENCE: 29
gatacatatg ctcttcaaga atgtctcg 28

<210> SEQ ID NO 30
<211> LENGTH: 32
<212> TYPE: DNA
<213> ORGANISM: Artificial sequence
<220> FEATURE:
<223> OTHER INFORMATION: Synthetic oligonucleotide primer

<400> SEQUENCE: 30
tcagctcgag ccagaccact tcagccatcg ag 32

<210> SEQ ID NO 31
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 31
gatacatatg aaccgaccct gcaatattgc 30

<210> SEQ ID NO 32
<211> LENGTH: 40
<212> TYPE: DNA
<213> ORGANISM: Artificial sequence
<220> FEATURE:
<223> OTHER INFORMATION: Synthetic oligonucleotide primer

<400> SEQUENCE: 32
tcagctcgag tcatgcgcgc ttctccagtt cggcgctggc 40

<210> SEQ ID NO 33
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 33
gatacatatg aagatcctgg tcaccggtgg tgg 33

<210> SEQ ID NO 34
<211> LENGTH: 34
<212> TYPE: DNA
<213> ORGANISM: Artificial sequence
<220> FEATURE:
<223> OTHER INFORMATION: Synthetic oligonucleotide primer

<400> SEQUENCE: 34
tcagctcgag ctatgcggca gatgaagcct tcag 34

<210> SEQ ID NO 35
<211> LENGTH: 29
<212> TYPE: DNA
<213> ORGANISM: Artificial sequence
<220> FEATURE:
<223> OTHER INFORMATION: Synthetic oligonucleotide primer

<400> SEQUENCE: 35
gatacatatg tcccagcttc ccggttacc 29

<210> SEQ ID NO 36
<211> LENGTH: 32
<212> TYPE: DNA
<213> ORGANISM: Artificial sequence
<220> FEATURE:
<223> OTHER INFORMATION: Synthetic oligonucleotide primer

<400> SEQUENCE: 36
tcagctcgag tcagatcggg ttcttgtcca gg 32

<210> SEQ ID NO 37
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 37
ggatacatgt tattcaaaaa tgtatctatc 30

<210> SEQ ID NO 38
<211> LENGTH: 29
<212> TYPE: DNA
<213> ORGANISM: Artificial sequence
<220> FEATURE:
<223> OTHER INFORMATION: Synthetic oligonucleotide primer

<400> SEQUENCE: 38
ctcgagaagc ttaccacaca acctcagcc 29

<210> SEQ ID NO 39
<211> LENGTH: 32
<212> TYPE: DNA
<213> ORGANISM: Artificial sequence
<220> FEATURE:
<223> OTHER INFORMATION: Synthetic oligonucleotide primer

<400> SEQUENCE: 39
ggatacatgt tatttcagaa tgtttctatc gc 32

<210> SEQ ID NO 40
<211> LENGTH: 35
<212> TYPE: DNA
<213> ORGANISM: Artificial sequence
<220> FEATURE:
<223> OTHER INFORMATION: Synthetic oligonucleotide primer

<400> SEQUENCE: 40
ctcgagaagc ttaccaaacc acttcggcca tgctg 35

<210> SEQ ID NO 41
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 41
ggatacatgt tattcaagca cgtcatgatc g 31

<210> SEQ ID NO 42
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 42
ctcgagaagc ttaccacgta acggacatca tag 33

<210> SEQ ID NO 43
<211> LENGTH: 22
<212> TYPE: PRT
<213> ORGANISM: Artificial sequence
<220> FEATURE:
<223> OTHER INFORMATION: Peptide motifs used to identify OleD enzymes
<220> FEATURE:
<221> NAME/KEY: misc_feature
<222> LOCATION: (1)..(1)
<223> OTHER INFORMATION: Xaa can be Ile, Leu, Val or Ala
<220> FEATURE:
<221> NAME/KEY: misc_feature
<222> LOCATION: (2)..(2)
<223> OTHER INFORMATION: Xaa can be Leu, Phe or Val
<220> FEATURE:
<221> NAME/KEY: misc_feature
<222> LOCATION: (6)..(6)
<223> OTHER INFORMATION: Xaa can be Gly, Ala or Cys
<220> FEATURE:
<221> NAME/KEY: misc_feature
<222> LOCATION: (7)..(7)
<223> OTHER INFORMATION: Xaa can be Gly, Ser or Asn
<220> FEATURE:
<221> NAME/KEY: misc_feature
<222> LOCATION: (9)..(9)
<223> OTHER INFORMATION: Xaa can be Phe, Leu or Met
<220> FEATURE:
<221> NAME/KEY: misc_feature
<222> LOCATION: (10)..(10)
<223> OTHER INFORMATION: Xaa can be Leu or Val
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be Leu, Val, Ile or Thr
<220> FEATURE:
<221> NAME/KEY: misc_feature
<222> LOCATION: (15)..(15)
<223> OTHER INFORMATION: Xaa can be Cys, Val or Ala
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 43

```
Xaa Xaa Val Thr Gly Xaa Xaa Gly Xaa Xaa Gly Xaa Xaa Xaa Xaa Xaa
1               5                   10                  15

Xaa Leu Xaa Xaa Xaa Gly
            20
```

<210> SEQ ID NO 44
<211> LENGTH: 10
<212> TYPE: PRT
<213> ORGANISM: Artificial sequence
<220> FEATURE:
<223> OTHER INFORMATION: Peptide motifs used to identify OleD enzymes
<220> FEATURE:
<221> NAME/KEY: misc_feature
<222> LOCATION: (2)..(2)
<223> OTHER INFORMATION: Xaa can be Asn, Val, Thr or Leu
<220> FEATURE:
<221> NAME/KEY: misc_feature
<222> LOCATION: (3)..(3)
<223> OTHER INFORMATION: Xaa can be Ala or Gly
<220> FEATURE:
<221> NAME/KEY: misc_feature
<222> LOCATION: (4)..(4)
<223> OTHER INFORMATION: Xaa can be Ala or Ser
<220> FEATURE:
<221> NAME/KEY: misc_feature
<222> LOCATION: (5)..(5)
<223> OTHER INFORMATION: Xaa can be Lys, Leu, Val, Ile, Gln or Arg
<220> FEATURE:
<221> NAME/KEY: misc_feature
<222> LOCATION: (6)..(6)
<223> OTHER INFORMATION: Xaa can be Val, Ala, Pro or Ile
<220> FEATURE:
<221> NAME/KEY: misc_feature
<222> LOCATION: (7)..(7)
<223> OTHER INFORMATION: Xaa can be Gly, Ser or Asp

```
<220> FEATURE:
<221> NAME/KEY: misc_feature
<222> LOCATION: (8)..(8)
<223> OTHER INFORMATION: Xaa can be Ala, Val, Leu, Ile or Met
<220> FEATURE:
<221> NAME/KEY: misc_feature
<222> LOCATION: (9)..(9)
<223> OTHER INFORMATION: Xaa can be any naturally occurring amino acid

<400> SEQUENCE: 44

His Xaa Xaa Xaa Xaa Xaa Xaa Xaa Xaa Gly
1               5                   10


<210> SEQ ID NO 45
<211> LENGTH: 19
<212> TYPE: PRT
<213> ORGANISM: Artificial sequence
<220> FEATURE:
<223> OTHER INFORMATION: Peptide motifs used to identify OleC enzymes
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Asp or Glu
<220> FEATURE:
<221> NAME/KEY: misc_feature
<222> LOCATION: (5)..(5)
<223> OTHER INFORMATION: Xaa can be Leu or Met
<220> FEATURE:
<221> NAME/KEY: misc_feature
<222> LOCATION: (6)..(6)
<223> OTHER INFORMATION: Xaa can be Pro, Ala, Cys or Ser
<220> FEATURE:
<221> NAME/KEY: misc_feature
<222> LOCATION: (7)..(7)
<223> OTHER INFORMATION: Xaa can be Thr, Ala or Gly
<220> FEATURE:
<221> NAME/KEY: misc_feature
<222> LOCATION: (10)..(10)
<223> OTHER INFORMATION: Xaa can be Leu or Pro
<220> FEATURE:
<221> NAME/KEY: misc_feature
<222> LOCATION: (12)..(12)
<223> OTHER INFORMATION: Xaa can be Ala, Ser or Gly
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be Leu or Met

<400> SEQUENCE: 45

Gly Xaa Xaa Xaa Xaa Xaa Xaa Phe Pro Xaa Phe Xaa Leu Phe Xaa Xaa
1               5                   10                  15

Ala Xaa Gly


<210> SEQ ID NO 46
<211> LENGTH: 25
<212> TYPE: PRT
<213> ORGANISM: Artificial sequence
<220> FEATURE:
<223> OTHER INFORMATION: Peptide motifs used to identify OleC enzymes
```

<220> FEATURE:
<221> NAME/KEY: misc_feature
<222> LOCATION: (6)..(6)
<223> OTHER INFORMATION: Xaa can be Val or leu
<220> FEATURE:
<221> NAME/KEY: misc_feature
<222> LOCATION: (7)..(7)
<223> OTHER INFORMATION: Xaa can be Gly or Ala
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid or no amino acid
<220> FEATURE:
<221> NAME/KEY: misc_feature
<222> LOCATION: (12)..(12)
<223> OTHER INFORMATION: Xaa can be any naturally occurring amino acid or no amino acid
<220> FEATURE:
<221> NAME/KEY: misc_feature
<222> LOCATION: (13)..(13)
<223> OTHER INFORMATION: Xaa can be any naturally occurring amino acid or no amino acid
<220> FEATURE:
<221> NAME/KEY: misc_feature
<222> LOCATION: (14)..(14)
<223> OTHER INFORMATION: Xaa can be any naturally occurring amino acid or no amino acid
<220> FEATURE:
<221> NAME/KEY: misc_feature
<222> LOCATION: (15)..(15)
<223> OTHER INFORMATION: Xaa can be any naturally occurring amino acid or no amino acid
<220> FEATURE:
<221> NAME/KEY: misc_feature
<222> LOCATION: (17)..(17)
<223> OTHER INFORMATION: Xaa can be Phe or Met
<220> FEATURE:
<221> NAME/KEY: misc_feature
<222> LOCATION: (18)..(18)
<223> OTHER INFORMATION: Xaa can be Cys or Tyr
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be His or Gln
<220> FEATURE:
<221> NAME/KEY: misc_feature
<222> LOCATION: (24)..(24)
<223> OTHER INFORMATION: Xaa can be Arg or Ile

<400> SEQUENCE: 46

```
His Arg Met Gly Asp Xaa Xaa Xaa Xaa Asp Xaa Xaa Xaa Xaa Xaa Trp
1               5                   10                  15

Xaa Xaa Gly Arg Lys Xaa Xaa Xaa Val
            20                  25
```

<210> SEQ ID NO 47
<211> LENGTH: 25
<212> TYPE: PRT
<213> ORGANISM: Artificial sequence
<220> FEATURE:
<223> OTHER INFORMATION: Peptide motifs used to identify OleC enzymes
<220> FEATURE:
<221> NAME/KEY: misc_feature
<222> LOCATION: (2)..(2)

<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be Val or Met
<220> FEATURE:
<221> NAME/KEY: misc_feature
<222> LOCATION: (10)..(10)
<223> OTHER INFORMATION: Xaa can be Ile or Val
<220> FEATURE:
<221> NAME/KEY: misc_feature
<222> LOCATION: (14)..(14)
<223> OTHER INFORMATION: Xaa can be Ala or Ser
<220> FEATURE:
<221> NAME/KEY: misc_feature
<222> LOCATION: (17)..(17)
<223> OTHER INFORMATION: Xaa can be Gly or Phe
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 47

```
Leu Xaa His Xaa Xaa Phe Pro Xaa Asp Xaa Arg His Asn Xaa Lys Ile
1               5                   10                  15

Xaa Arg Glu Xaa Leu Ala Xaa Trp Ala
            20                  25
```

<210> SEQ ID NO 48
<211> LENGTH: 7390
<212> TYPE: DNA
<213> ORGANISM: Artificial sequence
<220> FEATURE:
<223> OTHER INFORMATION: Synthetic nucleic acid sequence encoding
OleAOleB in combination

<400> SEQUENCE: 48

```
ggggaattgt gagcggataa caattcccct ctagaaataa ttttgtttaa ctttaagaag     60

gagatatacc atgggcagca gccatcacca tcatcaccac agccaggatc cgaattcgag    120

ctcggcgcgc ctgcaggtcg acaagcttgc ggccgcataa tgcttaagtc gaacagaaag    180

taatcgtatt gtacacggcc gcataatcga aattaatacg actcactata ggggaattgt    240

gagcggataa caattcccca tcttagtata ttagttaagt ataagaagga gatatacata    300

tgctcttcaa gaatgtctcg atcgccggcc tggcacacgt tgatgcgccg catacgctga    360

cgaccaagga aatcaacgag cggctgcagc cgacgttgga tcgcctcggt atccgcaccg    420

acgtgctcgg cgatatcgcc ggcatccatg cccgccgcct gtgggacaac ggcgtgcttg    480

cgtccgatgc cgccaccatg gccggccgca aggcgctgga agacgcgggc atcgatgcga    540

cgcaggtcgg cctgctggtc aacacctcgg tcagccgcga ctacctggag ccgtccacgg    600

cctccatcgt gtcgggcaac ctcggcgtca gcgacgagtg catgaccttc gacgtcgcca    660

atgcctgcct ggccttcatc aacggcatgg acatcgcggc gcgcatgatc gagcgcggcg    720

acatcgacta cgcgctggtg gtggatggcg agaccgccaa cctggtgtac gagaagaccc    780

tggagcgcat gaccgccccg gacgtcaccg ccgacgactt ccgcaacgaa ctggcggcgc    840
```

```
tgaccaccgg ttcgggtgct gcggcgatgg tgatggcgcg ctcggagctg gtgccggacg    900
cgccgcgcta caagggcggt gtcacccgtt cggccaccga gtggaaccag ctgtgcctgg    960
gcaacctgga ccggatggtc accgacaccc gcctgctgct gatcgaaggc atcaagctgg   1020
cgcagaagac cttcagcgcc gccaagatcg cactcggctg ggctgtggaa gaactggacc   1080
agttcgtgat ccaccaggtc agccagccgc acaccgccgc gttcatcaag aacttcggca   1140
tcgacccgaa gaaggtcatg accatcttcg gcgagcacgg caacatcggc ccggcctcgg   1200
tgccgatcgt gctgagcaag ctcaagcagc tgggcaagct gaagaagggc gatcgcatcg   1260
cgcttctggg cattggctcg ggcctgaact gctcgatggc tgaagtggtc tggtaacaaa   1320
gtcaccgctg acctgctgcg cgattgcctc gccaatcgct cgcgacggac agcgatgatc   1380
ttccaagtgt ccaagggccg gttctaccgg ccctttctac aggtgcgatc cgatgtccca   1440
gcttcccggt taccccgccc acccgcagcg cttcgaggtc cgccccggcc tgtcgatgaa   1500
ctatctcgac gaaggcccgc gcgatggcga agtggtggtg atggtgcacg gcaacccgtc   1560
gtggagctat tactggcgca cgctggtcgc cggcctgtcg gacacgtacc gctgcatcgt   1620
gccggaccac atcggcatgg gcctgtcgga caagcccgat gacagccgct acgagtacac   1680
gctgcagtcg cgcgttgacg acctcgatgc gctgctcaag catctgggca taaccggccc   1740
ggtgaccctg gcggtgcacg actggggcgg catgatcggt ttcggctggg cgctgtcgca   1800
ccacgaccag gtcaagcgcc tggtggtgct caataccgct gcattcccga tgccggcggc   1860
gaagaagatg ccgtggcaga tcgcgctggg ccgccactgg aagatcggcg agtggatcat   1920
ccgcaccttc aacgcgttct cctccggtgc ctcgtggctg ggcgtggagc ggaagatgcc   1980
ggccgacgtg cgccgcgcct acgtgtcgcc gtacaacagc tgggccaacc gcatcagcac   2040
catccgcttc atgcaggaca tcccgctgtc gccggccgac aaggcgtggt cgctgctgga   2100
gcatgccggc aaggcgctgc cgtcgttcgc cgaccggccg gccttcctcg gctggggcct   2160
gcgcgacttc gtgttcgacc accacttcct gaagggcttc caggccgcgc tgccgcaggc   2220
ccaggtacat gcgttcgagg acgccggcca ctacgtgctg gaagacaagc acgaagtgct   2280
ggtgccggaa atccgcgcgt tcctggacaa gaacccgatc tgactcgagt ctggtaaaga   2340
aaccgctgct gcgaaatttg aacgccagca catggactcg tctactagcg cagcttaatt   2400
aacctaggct gctgccaccg ctgagcaata actagcataa ccccttgggg cctctaaacg   2460
ggtcttgagg ggttttttgc tgaaaggagg aactatatcc ggattggcga atggacgcg    2520
ccctgtagcg gcgcattaag cgcggcgggt gtggtggtta cgcgcagcgt gaccgctaca   2580
cttgccagcg ccctagcgcc cgctcctttc gctttcttcc cttcctttct cgccacgttc   2640
gccggctttc cccgtcaagc tctaaatcgg gggctccctt tagggttccg atttagtgct   2700
ttacggcacc tcgaccccaa aaaacttgat tagggtgatg gttcacgtag tgggccatcg   2760
ccctgataga cggtttttcg ccctttgacg ttggagtcca cgttctttaa tagtggactc   2820
ttgttccaaa ctggaacaac actcaaccct atctcggtct attcttttga tttataaggg   2880
attttgccga tttcggccta ttggttaaaa aatgagctga tttaacaaaa atttaacgcg   2940
aattttaaca aaatattaac gtttacaatt tctggcggca cgatggcatg agattatcaa   3000
aaaggatctt cacctagatc cttttaaatt aaaaatgaag ttttaaatca atctaaagta   3060
tatatgagta aacttggtct gacagttacc aatgcttaat cagtgaggca cctatctcag   3120
cgatctgtct atttcgttca tccatagttg cctgactccc cgtcgtgtag ataactacga   3180
tacgggaggg cttaccatct ggccccagtg ctgcaatgat accgcgagac ccacgctcac   3240
```

cggctccaga tttatcagca ataaaccagc cagccggaag ggccgagcgc agaagtggtc 3300
ctgcaacttt atccgcctcc atccagtcta ttaattgttg ccgggaagct agagtaagta 3360
gttcgccagt taatagtttg cgcaacgttg ttgccattgc tacaggcatc gtggtgtcac 3420
gctcgtcgtt tggtatggct tcattcagct ccggttccca acgatcaagg cgagttacat 3480
gatcccccat gttgtgcaaa aaagcggtta gctccttcgg tcctccgatc gttgtcagaa 3540
gtaagttggc cgcagtgtta tcactcatgg ttatggcagc actgcataat tctcttactg 3600
tcatgccatc cgtaagatgc ttttctgtga ctggtgagta ctcaaccaag tcattctgag 3660
aatagtgtat gcggcgaccg agttgctctt gcccggcgtc aatacgggat aataccgcgc 3720
cacatagcag aactttaaaa gtgctcatca ttggaaaacg ttcttcgggg cgaaaactct 3780
caaggatctt accgctgttg agatccagtt cgatgtaacc cactcgtgca cccaactgat 3840
cttcagcatc ttttactttc accagcgttt ctgggtgagc aaaaacagga aggcaaaatg 3900
ccgcaaaaaa gggaataagg gcgacacgga aatgttgaat actcatactc ttcctttttc 3960
aatcatgatt gaagcattta tcagggttat tgtctcatga gcggatacat atttgaatgt 4020
atttagaaaa ataaacaaat aggtcatgac caaaatccct taacgtgagt tttcgttcca 4080
ctgagcgtca gaccccgtag aaaagatcaa aggatcttct tgagatcctt tttttctgcg 4140
cgtaatctgc tgcttgcaaa caaaaaaacc accgctacca gcggtggttt gtttgccgga 4200
tcaagagcta ccaactcttt ttccgaaggt aactggcttc agcagagcgc agataccaaa 4260
tactgtcctt ctagtgtagc cgtagttagg ccaccacttc aagaactctg tagcaccgcc 4320
tacatacctc gctctgctaa tcctgttacc agtggctgct gccagtggcg ataagtcgtg 4380
tcttaccggg ttggactcaa gacgatagtt accggataag gcgcagcggt cgggctgaac 4440
ggggggttcg tgcacacagc ccagcttgga gcgaacgacc tacaccgaac tgagatacct 4500
acagcgtgag ctatgagaaa gcgccacgct tcccgaaggg agaaaggcgg acaggtatcc 4560
ggtaagcggc agggtcggaa caggagagcg cacgagggag cttccagggg gaaacgcctg 4620
gtatctttat agtcctgtcg ggtttcgcca cctctgactt gagcgtcgat ttttgtgatg 4680
ctcgtcaggg gggcggagcc tatggaaaaa cgccagcaac gcggcctttt tacggttcct 4740
ggccttttgc tggccttttg ctcacatgtt ctttcctgcg ttatcccctg attctgtgga 4800
taaccgtatt accgcctttg agtgagctga taccgctcgc cgcagccgaa cgaccgagcg 4860
cagcgagtca gtgagcgagg aagcggaaga gcgcctgatg cggtattttc tccttacgca 4920
tctgtgcggt atttcacacc gcatatatgg tgcactctca gtacaatctg ctctgatgcc 4980
gcatagttaa gccagtatac actccgctat cgctacgtga ctgggtcatg gctgcgcccc 5040
gacacccgcc aacacccgct gacgcgccct gacgggcttg tctgctcccg gcatccgctt 5100
acagacaagc tgtgaccgtc tccgggagct gcatgtgtca gaggttttca ccgtcatcac 5160
cgaaacgcgc gaggcagctg cggtaaagct catcagcgtg gtcgtgaagc gattcacaga 5220
tgtctgcctg ttcatccgcg tccagctcgt tgagtttctc cagaagcgtt aatgtctggc 5280
ttctgataaa gcgggccatg ttaagggcgg ttttttcctg tttggtcact gatgcctccg 5340
tgtaaggggg atttctgttc atgggggtaa tgataccgat gaaacgagag aggatgctca 5400
cgatacgggt tactgatgat gaacatgccc ggttactgga acgttgtgag ggtaaacaac 5460
tggcggtatg gatgcggcgg gaccagagaa aaatcactca gggtcaatgc cagcgcttcg 5520
ttaatacaga tgtaggtgtt ccacagggta gccagcagca tcctgcgatg cagatccgga 5580
acataatggt gcagggcgct gacttccgcg tttccagact ttacgaaaca cggaaaccga 5640
agaccattca tgttgttgct caggtcgcag acgttttgca gcagcagtcg cttcacgttc 5700
gctcgcgtat cggtgattca ttctgctaac cagtaaggca accccgccag cctagccggg 5760
tcctcaacga caggagcacg atcatgctag tcatgccccg cgcccaccgg aaggagctga 5820
ctgggttgaa ggctctcaag ggcatcggtc gagatcccgg tgcctaatga gtgagctaac 5880
ttacattaat tgcgttgcgc tcactgcccg ctttccagtc gggaaacctg tcgtgccagc 5940
tgcattaatg aatcggccaa cgcgcgggga gaggcggttt gcgtattggg cgccagggtg 6000
gtttttcttt tcaccagtga gacgggcaac agctgattgc ccttcaccgc ctggccctga 6060
gagagttgca gcaagcggtc cacgctggtt tgccccagca ggcgaaaatc ctgtttgatg 6120
gtggttaacg gcgggatata acatgagctg tcttcggtat cgtcgtatcc cactaccgag 6180
atgtccgcac caacgcgcag cccggactcg gtaatggcgc gcattgcgcc cagcgccatc 6240
tgatcgttgg caaccagcat cgcagtggga acgatgccct cattcagcat ttgcatggtt 6300
tgttgaaaac cggacatggc actccagtcg ccttcccgtt ccgctatcgg ctgaatttga 6360
ttgcgagtga gatatttatg ccagccagcc agacgcagac gcgccgagac agaacttaat 6420
gggcccgcta acagcgcgat ttgctggtga cccaatgcga ccagatgctc cacgcccagt 6480
cgcgtaccgt cttcatggga gaaaataata ctgttgatgg gtgtctggtc agagacatca 6540
agaaataacg ccggaacatt agtgcaggca gcttccacag caatggcatc ctggtcatcc 6600
agcggatagt taatgatcag cccactgacg cgttgcgcga gaagattgtg caccgccgct 6660
ttacaggctt cgacgccgct tcgttctacc atcgacacca ccacgctggc acccagttga 6720
tcggcgcgag atttaatcgc cgcgacaatt tgcgacggcg cgtgcagggc cagactggag 6780
gtggcaacgc caatcagcaa cgactgtttg cccgccagtt gttgtgccac gcggttggga 6840
atgtaattca gctccgccat cgccgcttcc actttttccc gcgttttcgc agaaacgtgg 6900
ctggcctggt tcaccacgcg ggaaacggtc tgataagaga caccggcata ctctgcgaca 6960
tcgtataacg ttactggttt cacattcacc accctgaatt gactctcttc cgggcgctat 7020
catgccatac cgcgaaaggt tttgcgccat tcgatggtgt ccgggatctc gacgctctcc 7080
cttatgcgac tcctgcatta ggaagcagcc cagtagtagg ttgaggccgt tgagcaccgc 7140
cgccgcaagg aatggtgcat gcaaggagat ggcgcccaac agtcccccgg ccacggggcc 7200
tgccaccata cccacgccga aacaagcgct catgagcccg aagtggcgag cccgatcttc 7260
cccatcggtg atgtcggcga tataggcgcc agcaaccgca cctgtggcgc cggtgatgcc 7320
ggccacgatg cgtccggcgt agaggatcga gatcgatctc gatcccgcga aattaatacg 7380
actcactata 7390

<210> SEQ ID NO 49
<211> LENGTH: 6313
<212> TYPE: DNA
<213> ORGANISM: Artificial sequence
<220> FEATURE:
<223> OTHER INFORMATION: Synthetic nucleic acid sequence encoding OleCOleD in combination

<400> SEQUENCE: 49
ggggaattgt gagcggataa caattcccct gtagaaataa ttttgtttaa ctttaataag 60
gagatatacc atgggcagca gccatcacca tcatcaccac agccaggatc cgaattcgag 120
ctcggcgcgc ctgcaggtcg acaagcttgc ggccgcataa tgcttaagtc gaacagaaag 180
taatcgtatt gtacacggcc gcataatcga aattaatacg actcactata ggggaattgt 240

-continued

```
gagcggataa caattcccca tcttagtata ttagttaagt ataagaagga gatatacata     300
tgaaccgacc ctgcaatatt gccgcccgct tgcctgaact ggcgcgtgaa cggcccgacc     360
agatcgccat ccgctgcccg ggccgccgtg gcgccggcaa cggcatggcc gcctacgacg     420
tgaccctgga ttaccgccag ctggacgccc gcagcgacgc catggcggct ggcctggcag     480
gctacgggat cggtcgcggg gtgcgcacgg tggtgatggt gcggccgtcg ccggagttct     540
tcctgttgat gtttgccctg ttcaaactgg gtgcggtgcc ggtgctggtc gacccgggca     600
tcgacaaacg cgcgctgaag cagtgcctgg atgaggcgca gccggaggct ttcattggca     660
ttccgctggc acacgtggcg cggttggcgc tgcgctgggc gcgctcggcg acccgcctgg     720
tcaccgtcgg ccgccgcctc ggctggggcg ggaccacgct ggccgcgctg gagcgcgccg     780
gtgccaacgg gggggcgatg ctggccgcca ccgatggcga ggacatggcc gcgatcctgt     840
tcaccagcgg ctccaccggc gtgcccaagg gcgtggtcta ccgccaccgt catttcgtcg     900
gccagatcca gctgctgggc agtgcctttg gcatggaagc gggcggggtg gacctgccga     960
ccttcccgcc gtttgccttg ttcgacccgg cgctgggcct gacctcggtg atcccggaca    1020
tggacccgac ccggccggca caggccgacc cggcacgcct gcatgacgcc atccagcgct    1080
tcggcgtgac ccagctgttt ggctcgcctg cgctgatgcg ggtgctggcc cgtcacggcc    1140
ggccgttgcc gacggtgacc cgggtgacct cggccggtgc gccggtgccg ccggatgtgg    1200
tcgccaccat ccgcagcctg ttgccggccg atgcgcagtt ctggaccccg tacggcgcca    1260
ccgagtgcct gccggtggcg gtggtggaag gccgcgagct ggagcgcacc cgtgccgcca    1320
ccgaggccgg cgccggtacc tgcgtgggca gcgtggttga accgaatgag gtgcgcatca    1380
tcggcatcga tgacggaccg ttggccgact ggtcgcaggc gcgcgtgctg gccaccggcg    1440
aggtgggcga gatcaccgtg gccggaccga ccgctaccga cagttacttc aaccgcccgc    1500
aggccaccgc ggcggcgaag atccgcgaga ccctggccga tggcagcacg cgcgtggtgc    1560
accgcatggg tgacgtgggc tacttcgatg cgcagggccg cctgtggttc tgcggccgca    1620
agacccatcg cgtggaaacc gcacgggggc cgctgtacac cgaacaggtg gagccggtgt    1680
tcaataccgt gcccggggtg gcgcgcacgg cgctggtcgg tgttggtccg gcgggagcac    1740
aggtgccggt gctgtgcgtg gagctgcagc gtggccagtc agacagcccg gcgctgcagg    1800
aggcgctgcg tgcgcacgcc gcagcccgcg caccggaggc cggcctgcag cacttcctgg    1860
tgcatccggc gttccccgtc gatatccgtc acaacgccaa gatcggccgc gagaagctcg    1920
ccgtctgggc cagcgccgaa ctggagaagc gcgcatgaag atcctggtca ccggtggtgg    1980
tggtttcctt ggccaggcgc tgtgccgtgg gctggtcgaa cgtggccacc aggtgctggc    2040
gttcaaccgc agccactacc cggaactgca ggccatgggc gtgggccaga tccgcggcga    2100
tctggccgat gcgcaggcgg tgctgcatgc agtggccggc gtcgatgcgg tattccacaa    2160
cggtgcgaag gccggcgcct ggggcagcta tgacagctac caccaggcca acgtggtcgg    2220
caccgacaac gtgatcgccg cctgccgcgc gcacggcatc agccggctgg tctacacctc    2280
cacgcccagc gtgacccacc gcgcgaccca cccggtggaa ggcctggggg ctgatgaggt    2340
gccgtacggc gaggacttcc aggcgccgta tgcggcgacc aaggcgattg ccgaacagcg    2400
cgtgctggcc gccaacgatg ccacgctggc gacggtggca ctgcgcccgc gcctgatctg    2460
gggcccgggc gaccagcagc tggtgccccg cctggccgaa cgcgcacggc aggggcgcct    2520
gcgcctggtc ggcgatggca acaacaaggt cgataccacc tacatcgaca acgccgcgct    2580
cgcgcatttc ctcgccttgg atgcactggc accgggtgcg gcctgtgcgg gcagggcgta    2640
```

```
cttcatttcc aacggcgagc cgctgccgat gcgcgagctg gtcaacaagc tgctggccgc   2700
tgtgggtgcg ccgacggtgg acaaggcgat cagcttcaag accgcttatc gcattggtgc   2760
ggtctgcgaa cggctgtggc cgctgctgcg cctgcgcggc gagccgccgt tgacccgctt   2820
cctggccgag cagctgtgca cgccgcactg gtacagcatg gagccggcac gccgggactt   2880
cggttacgtg ccgcaggtca gcattgaaga agggctgcgc aggctgaagg cttcatctgc   2940
cgcatagctc gagtctggta aagaaaccgc tgctgcgaaa tttgaacgcc agcacatgga   3000
ctcgtctact agcgcagctt aattaaccta ggctgctgcc accgctgagc aataactagc   3060
ataacccctt ggggcctcta aacgggtctt gaggggtttt ttgctgaaac ctcaggcatt   3120
tgagaagcac acggtcacac tgcttccggt agtcaataaa ccggtaaacc agcaatagac   3180
ataagcggct atttaacgac cctgccctga accgacgaca agctgacgac cgggtctccg   3240
caagtggcac ttttcgggga aatgtgcgcg gaacccctat ttgtttattt ttctaaatac   3300
attcaaatat gtatccgctc atgaattaat tcttagaaaa actcatcgag catcaaatga   3360
aactgcaatt tattcatatc aggattatca ataccatatt tttgaaaaag ccgtttctgt   3420
aatgaaggag aaaactcacc gaggcagttc cataggatgg caagatcctg gtatcggtct   3480
gcgattccga ctcgtccaac atcaatacaa cctattaatt tcccctcgtc aaaaataagg   3540
ttatcaagtg agaaatcacc atgagtgacg actgaatccg gtgagaatgg caaaagttta   3600
tgcatttctt tccagacttg ttcaacaggc cagccattac gctcgtcatc aaaatcactc   3660
gcatcaacca aaccgttatt cattcgtgat tgcgcctgag cgagacgaaa tacgcggtcg   3720
ctgttaaaag gacaattaca aacaggaatc gaatgcaacc ggcgcaggaa cactgccagc   3780
gcatcaacaa tattttcacc tgaatcagga tattcttcta atacctggaa tgctgttttc   3840
ccggggatcg cagtggtgag taaccatgca tcatcaggag tacggataaa atgcttgatg   3900
gtcggaagag gcataaattc cgtcagccag tttagtctga ccatctcatc tgtaacatca   3960
ttggcaacgc tacctttgcc atgtttcaga aacaactctg gcgcatcggg cttcccatac   4020
aatcgataga ttgtcgcacc tgattgcccg acattatcgc gagcccattt atacccatat   4080
aaatcagcat ccatgttgga atttaatcgc ggcctagagc aagacgtttc ccgttgaata   4140
tggctcatac tcttcctttt tcaatattat tgaagcattt atcagggtta ttgtctcatg   4200
agcggataca tatttgaatg tatttagaaa aataaacaaa taggcatgct agcgcagaaa   4260
cgtcctagaa gatgccagga ggatacttag cagagagaca ataaggccgg agcgaagccg   4320
tttttccata ggctccgccc ccctgacgaa catcacgaaa tctgacgctc aaatcagtgg   4380
tggcgaaacc cgacaggact ataaagatac caggcgtttc cccctgatgg ctccctcttg   4440
cgctctcctg ttcccgtcct gcggcgtccg tgttgtggtg gaggctttac ccaaatcacc   4500
acgtcccgtt ccgtgtagac agttcgctcc aagctgggct gtgtgcaaga acccccccgtt   4560
cagcccgact gctgcgcctt atccggtaac tatcatcttg agtccaaccc ggaaagacac   4620
gacaaaacgc cactggcagc agccattggt aactgagaat tagtggattt agatatcgag   4680
agtcttgaag tggtggccta acagaggcta cactgaaagg acagtatttg gtatctgcgc   4740
tccactaaag ccagttacca ggttaagcag ttccccaact gacttaacct tcgatcaaac   4800
cgcctcccca ggcggttttt tcgtttacag agcaggagat tacgacgatc gtaaaaggat   4860
ctcaagaaga tcctttacgg attcccgaca ccatcactct agatttcagt gcaatttatc   4920
tcttcaaatg tagcacctga agtcagcccc atacgatata agttgtaatt ctcatgttag   4980
tcatgccccg cgcccaccgg aaggagctga ctgggttgaa ggctctcaag ggcatcggtc   5040
```

-continued

```
gagatcccgg tgcctaatga gtgagctaac ttacattaat tgcgttgcgc tcactgcccg    5100

ctttccagtc gggaaacctg tcgtgccagc tgcattaatg aatcggccaa cgcgcgggga    5160

gaggcggttt gcgtattggg cgccagggtg gtttttcttt tcaccagtga gacgggcaac    5220

agctgattgc ccttcaccgc ctggccctga gagagttgca gcaagcggtc cacgctggtt    5280

tgccccagca ggcgaaaatc ctgtttgatg gtggttaacg gcgggatata acatgagctg    5340

tcttcggtat cgtcgtatcc cactaccgag atgtccgcac caacgcgcag cccggactcg    5400

gtaatggcgc gcattgcgcc cagcgccatc tgatcgttgg caaccagcat cgcagtggga    5460

acgatgccct cattcagcat ttgcatggtt tgttgaaaac cggacatggc actccagtcg    5520

ccttcccgtt ccgctatcgg ctgaatttga ttgcgagtga gatatttatg ccagccagcc    5580

agacgcagac gcgccgagac agaacttaat gggcccgcta acagcgcgat ttgctggtga    5640

cccaatgcga ccagatgctc cacgcccagt cgcgtaccgt cttcatggga gaaaataata    5700

ctgttgatgg gtgtctggtc agagacatca agaaataacg ccggaacatt agtgcaggca    5760

gcttccacag caatggcatc ctggtcatcc agcggatagt taatgatcag cccactgacg    5820

cgttgcgcga gaagattgtg caccgccgct ttacaggctt cgacgccgct tcgttctacc    5880

atcgacacca ccacgctggc acccagttga tcggcgcgag atttaatcgc cgcgacaatt    5940

tgcgacggcg cgtgcagggc cagactggag gtggcaacgc caatcagcaa cgactgtttg    6000

cccgccagtt gttgtgccac gcggttggga atgtaattca gctccgccat cgccgcttcc    6060

actttttccc gcgttttcgc agaaacgtgg ctggcctggt tcaccacgcg ggaaacggtc    6120

tgataagaga caccggcata ctctgcgaca tcgtataacg ttactggttt cacattcacc    6180

accctgaatt gactctcttc cgggcgctat catgccatac cgcgaaaggt tttgcgccat    6240

tcgatggtgt ccgggatctc gacgctctcc cttatgcgac tcctgcatta ggaaattaat    6300

acgactcact ata                                                       6313
```

PROCESS FOR PRODUCING LOW MOLECULAR WEIGHT HYDROCARBONS FROM RENEWABLE RESOURCES

CROSS REFERENCE TO RELATED APPLICATION

This application claims the benefit of U.S. Provisional Application No. 60/894,907 filed Mar. 14, 2007, U.S. Provisional Application No. 60/908,547 filed Mar. 28, 2007, International Application No. PCT/US2007/011923 filed May 18, 2007, U.S. Provisional Application No. 60/931,370 filed May 22, 2007, U.S. Provisional Application No. 60/931,939 filed May 25, 2007, U.S. Provisional Application No. 60/951,944 filed Jul. 25, 2007 and U.S. Provisional Application No. 60/974,810 filed Sep. 24, 2007 all of which are incorporated herein by reference in their entireties.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 90,826 bytes ASCII (Text) file named "ReplacementSequenceListing" created Nov. 3, 2011.

FIELD

Described herein are compositions and methods of producing such compositions that are useful as fuels or fuel production feedstock.

BACKGROUND

Low molecular weight fuel is relatively expensive in part from the processing conditions necessary to "crack" petroleum derived hydrocarbons into smaller molecular weight molecules. The cracking process also produces many undesirable molecules that have low combustion value and do not contribute positively to fuel quality. In addition, the chemical composition of petroleum-based crude oil is unpredictable because the composition varies depending on the geological location of the petroleum's extraction. Such unpredictability leads to increased cracking process control complexity.

SUMMARY

Disclosed herein are various cracking methods for producing low molecular weight hydrocarbons from biocrude or hydrocarbon feedstock. Biocrude or hydrocarbon feedstock can be used as the starting material for cracking. In some examples, biocrude is the starting material that is cracked. In other examples, hydrocarbon feedstock is the starting material that is cracked. The biocrude or hydrocarbon feedstock may be produced from a recombinant microorganism.

According to one embodiment, disclosed herein are methods that include obtaining biocrude or hydrocarbon feedstock produced by a recombinant microorganism and cracking the biocrude or hydrocarbon feedstock resulting in a cracked product.

According to one embodiment, disclosed herein are methods for cracking a biocrude or hydrocarbon feedstock resulting in a cracked product, wherein the biocrude or hydrocarbon feedstock is substantially free of any compounds that include oxygen and is produced by a recombinant microorganism. For example, the method could include obtaining biocrude produced by a recombinant microorganism wherein the biocrude is substantially free of any compounds that include oxygen and cracking the biocrude resulting in a cracked product.

According to further embodiments, disclosed herein are methods for cracking biocrude or hydrocarbon feedstock produced by a recombinant microorganism resulting in a cracked product, wherein the biocrude or hydrocarbon feedstock includes greater than about 90 wt % alkene compounds, based on the total weight of the biocrude.

According to another embodiment, disclosed herein are methods for cracking biocrude or hydrocarbon feedstock that include catalytically cracking the biocrude or hydrocarbon feedstock at a temperature of 350° C. or lower.

Also disclosed herein are methods for catalytically cracking a biocrude or hydrocarbon feedstock produced by a microorganism, wherein the biocrude or hydrocarbon feedstock includes greater than about 50 wt % $C_{19}$-$C_{31}$ compounds, based on the total weight of the biocrude resulting in a cracked product.

According to a further embodiment, disclosed herein are methods for cracking a biocrude or hydrocarbon feedstock produced by a recombinant microorganism, wherein the hydrocarbon feedstock includes $C_{19}$ to $C_{31}$ hydrocarbons having at least one alkene moiety or $C_{22}$ to $C_{36}$ hydrocarbons having at least one alkene moiety, resulting in a cracked product.

According to an additional embodiment, disclosed herein are methods for making a biofuel that include culturing a recombinant microorganism engineered to produce biocrude under conditions sufficient to produce biocrude and catalytically cracking the biocrude to produce a biofuel.

Also disclosed herein are mixtures that include any of the cracked products described herein and at least one other fuel component.

Also disclosed herein are methods that include mixing a biocrude disclosed herein with petroleum crude and cracking the resulting mixture.

Also disclosed herein is a biofuel mixture produced from a biocrude, wherein the biofuel includes a gasoline fraction that distills (at 1 atm) at about 20 to about 210° C.; a jet fuel fraction that distills (at 1 atm) at about 170 to about 290° C.; and diesel fraction that distills (at 1 atm) at about 180 to about 320° C.

Also disclosed herein is a biofuel mixture produced from a biocrude, wherein the biofuel includes a $C_5$-$C_{10}$ fraction having a boiling point range (at 1 atm) of about 30 to about 180° C.; a $C_8$-$C_{14}$ fraction having a boiling point range (at 1 atm) of about 120 to about 260° C.; and a $C_{14}$-$C_{18}$ fraction having a boiling point range (at 1 atm) of about 230 to about 320° C.

The foregoing and other objects, features, and advantages will become more apparent from the following detailed description, which proceeds with reference to the accompanying Figures.

BRIEF DESCRIPTION OF THE DRAWINGS

FIG. 2 also identifies exemplary fatty acid biosynthetic pathway product forming enzymes.

FIGS. 4A-J are a series of ten MS spectra for the hydrocarbons shown in FIG. 3. FIG. 4A shows the MS spectra data for $C_{27}$ triene. FIG. 4B shows the MS spectra data for $C_{27}$ diene. FIG. 4C shows the MS spectra data for $C_{27}$ monoene. FIG. 4D shows the MS spectra data for $C_{28}$ diene. FIG. 4E shows the MS spectra data for $C_{29}$ triene. FIG. 4F shows the MS spectra data for $C_{29}$ diene. FIG. 4G shows the MS spectra data for $C_{29}$ monoene. FIG. 4H shows the MS spectra data for $C_{30}$ diene. FIG. 4I shows the MS spectra data for $C_{31}$ triene. FIG. 4J shows the MS spectra data for $C_{31}$ diene.

FIG. 7 is a table listing several different enzymes and their corresponding genes. These genes can be manipulated to be over expressed or attenuated to increase or alter the structure of the biocrude produced. The table indicates for each gene the manipulation that can be used alone or in combination with other manipulations to alter biocrude production.

SEQUENCE LISTING

Figure 1:
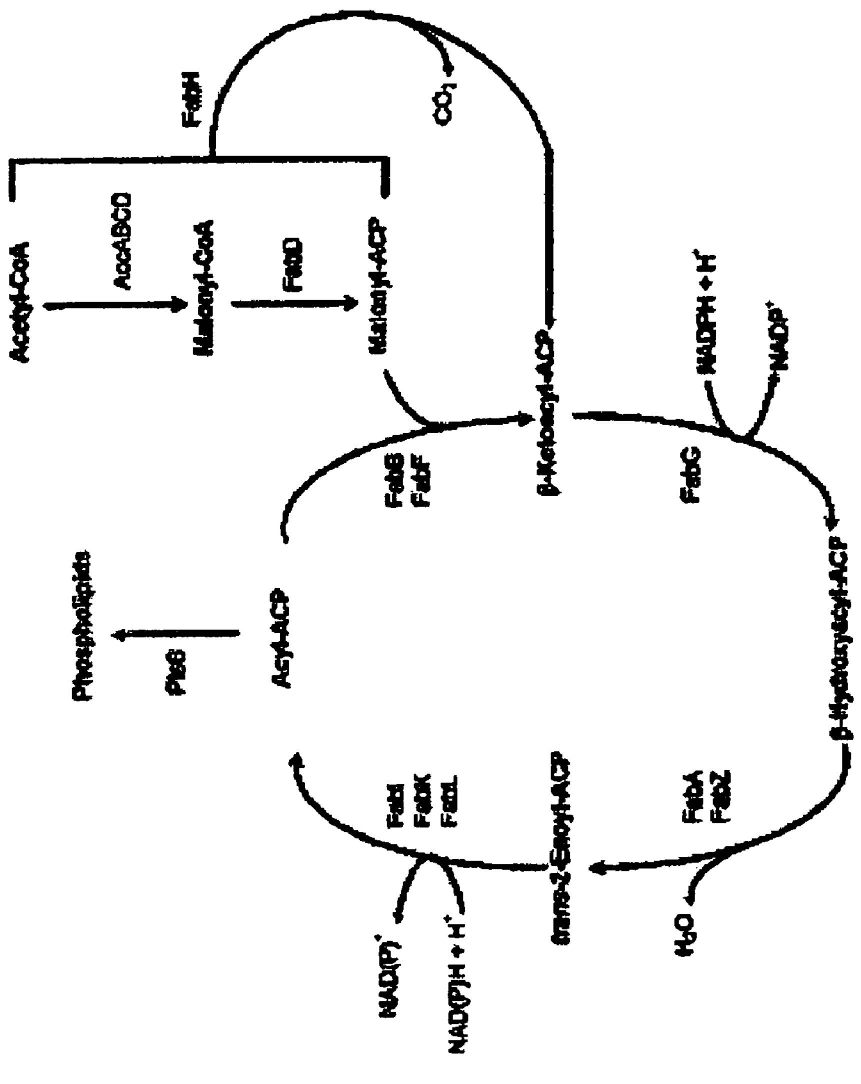
FIG. 1 shows a portion of the fatty acid biosynthetic pathway.

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows a nucleic acid sequence that encodes the amino acid sequence of OleA as cloned from *Stenotrophomonas maltophilia* ATCC 17679.

SEQ ID NO: 2 shows the amino acid sequence encoded by the nucleic acid sequence shown in SEQ ID NO: 1.

SEQ ID NO: 3 shows a nucleic acid sequence encoding OleA from *Stenotrophomonas maltophilia* that has been optimized for expression in *E. coli.*

SEQ ID NO: 4 shows the amino acid sequence encoded by SEQ ID NO: 3, which differs from the OleA amino acid sequence shown in SEQ ID NO: 2 at positions 79 and 246. The following amino acid sequence represents the OleA protein found in *Stenotrophomonas maltophilia* R551 (GenBank Accession #EAX23835).

SEQ ID NO: 5 shows a nucleic acid sequence that encodes the amino acid sequence of OleC as cloned from *Stenotrophomonas maltophilia* ATCC 17679.

SEQ ID NO: 6 shows the amino acid sequence encoded by SEQ ID NO: 5 which differs from the OleC amino acid sequence shown in GenBank under *Stenotrophomonas maltophilia* R551 (GenBank Accession #EAX23838), at positions 130, 135, 166, 362, 366, 369, 378, 409, 417, 449, and 546.

SEQ ID NO: 7 shows a nucleic acid sequence that encodes the amino acid sequence of OleD as cloned from *Stenotrophomonas maltophilia* ATCC 17679.

SEQ ID NO: 8 shows the amino acid sequence encoded by SEQ ID NO: 7, which differs from the OleD amino acid sequence shown in GenBank under *Stenotrophomonas maltophilia* R551 (GenBank Accession #EAX23839), at positions 101, 128, 215, 216 and 227.

SEQ ID NO: 9 shows the nucleic acid sequence that encodes the amino acid sequence of OleB as cloned from *Stenotrophomonas maltophilia* ATCC 17679.

SEQ ID NO: 10 shows the amino acid sequence encoded by SEQ ID NO: 9. which differs from the OleB amino acid sequence shown in GenBank under *Stenotrophomonas maltophilia* 8551 (GenBank Accession #EAX23836), at positions 197, 224 and 279.

SEQ ID NO: 11 shows a nucleic acid sequence that encodes the amino acid sequence of OleA from *Xanthomonas axonopodis* (Gen Bank accession #NP_640589.1).

SEQ ID NO: 12 shows the amino acid sequence encoded by SEQ ID NO: 11. The amino acid sequence is derived from GenBank accession #AAM35125.

SEQ ID NO: 13 shows a nucleic acid sequence that encodes the amino acid sequence of OleC from *Xanthomonas axonopodis* (GenBank accession #NP_640589.1).

SEQ ID NO: 14 shows the amino acid sequence encoded by SEQ ID NO: 13.

SEQ ID NO: 15 shows a nucleic acid sequence that encodes the amino acid sequence of OleD from *Xanthomonas axonopodis* (GenBank accession #NP_640589.1).

SEQ ID NO: 16 shows the amino acid sequence encoded by SEQ ID NO: 15.

SEQ ID NO: 17 shows a nucleic acid sequence that encodes the amino acid sequence of OleA from *Chloroflexus aggregans* DSM (GenBank accession #ZP_01515932.1).

SEQ ID NO: 18 shows the amino acid sequence encoded by SEQ ID NO: 17.

SEQ ID NO: 19 shows a nucleic acid sequence that encodes the amino acid sequence of OleC from *Chloroflexus aggregans* DSM (GenBank accession #ZP_01515932.1).

SEQ ID NO: 20 shows the amino acid sequence encoded by SEQ ID NO: 19.

SEQ ID NO: 21 shows a nucleic acid sequence that encodes the amino acid sequence of OleD from *Chloroflexus aggregans* DSM (GenBank accession #ZP_01515932.1).

SEQ ID NO: 22 shows the amino acid sequence encoded by SEQ ID NO: 21.

SEQ ID NO: 23-28 show amino acid motifs that can be used to identify additional OleA protein sequences.

SEQ ID NOS: 29-42 show PCR primer sequences.

SEQ ID NOS: 43-44 show two motifs that can be used to identify OleD sequences.

SEQ ID NOS: 45-47 show two motifs that can be used to identify OleC sequences.

SEQ ID NO: 48 shows the nucleic acid sequence encoding OleA and OleB in combination.

SEQ ID NO: 49 shows the nucleic acid sequence encoding OleC and OleD in combination.

DETAILED DESCRIPTION

I. Abbreviations

Unless otherwise noted, technical terms are used according to conventional usage. Definitions of common terms in molecular biology can be found in Benjamin Lewin, *Genes VII*, Oxford University Press, 1999 (ISBN 0-19-879276-X); Kendrew et al. (eds.), *The Encyclopedia of Molecular Biology*

Blackwell Science Ltd., 1994 (ISBN 0-632-02182-9); and Robert A. Meyers (ed.), *Molecular Biology and Biotechnology: a Comprehensive Desk Reference*, VCH Publishers, Inc., 1995 (ISBN 1-56081-569-8).

ADH: alcohol dehydrogenase
AP: alkaline phosphatase
Bp: base pairs
CAT: chloramphenicol acetyltransferase
DNA: deoxyribonucleic acid
GC/MS: gas chromatograph/mass spectrometer
GFP: green fluorescent protein
PCR: polymerase chain reaction
RT-PCR: reverse transcriptase polymerase chain reaction II. Terms In order to facilitate review of the various embodiments of the disclosure, the following explanations of specific terms are provided:

Accession Numbers: The accession numbers throughout this disclosure are derived from the NCBI database (National Center for Biotechnology Information) maintained by the National Institute of Health, U.S.A. The accession numbers are as provided in the database on March 2008.

Aliphatic ketone: The term "aliphatic" includes alkyl, alkenyl, and alkynyl groups. The term "aliphatic ketone" refers to a compound including a carbonyl moiety substituted with two aliphatic groups. Aliphatic ketones include, by way of example, alkyl alkyl ketones (compounds with a carbonyl group bonded to two alkyl groups), alkyl alkenyl ketones, and alkenyl alkenyl ketones. Aliphatic ketone synthase activity, as used herein, refers to enzymatic activity resulting in the production of an aliphatic ketone.

Alkene: The term "alkene" refers to branched, unbranched or cyclic hydrocarbons having at least one carbon-carbon double bond. An "alkene" is inclusive of compounds having more than one carbon-carbon double bond such as alkadienes, alkatrienes, etc . . . (i.e., polyenes). An "alkene" also is inclusive of cycloalkenes. In some examples, an alkene can be substituted with another functional group moiety such as, but not limited to, aryl or hydroxyl.

Attenuate: To lessen the impact, activity or strength of something. In one example, the sensitivity of a particular enzyme to feedback inhibition or inhibition caused by a composition that is not a product or a reactant (non-pathway specific feedback) is lessened such that the enzyme activity is not impacted by the presence of a compound. For example, the fabH gene and its corresponding amino acid sequence are temperature sensitive and can be altered to decrease the sensitivity to temperature fluctuations. The attenuation of the fabH gene can be used when branched hydrocarbons are desired. In another example, an enzyme that has been altered to be less active can be referred to as attenuated.

A functional deletion of an enzyme can be used to attenuate an enzyme. A functional deletion is a mutation, partial or complete deletion, insertion, or other variation made to a gene sequence or a sequence controlling the transcription of a gene sequence that reduces or inhibits production of the gene product or renders the gene product non-functional. For example, functional deletion of fabR in *E. coli* reduces the repression of the fatty acid biosynthetic pathway and allows *E. coli* to produce more unsaturated fatty acids (UFAs), which can allow for the production of more hydrocarbons. In some instances a functional deletion is described as a knock-out mutation.

One of ordinary skill in the art will appreciate that there are many methods of attenuating an enzyme activity. For example, attenuation can be accomplished by introducing amino acid sequence changes via altering the nucleic acid sequence, placing the gene under the control of a less active promoter, expressing interfering RNA, ribozymes or antisense sequences that target the gene of interest, or through any other technique known in the art.

Bacteria: The term "bacteria" refers to organisms in the domains Bacteria and Archaea. The universal phylogenetic tree is divided into three kingdoms or domains: Bacteria, Archaea and Eukarya. Bacteria and Archaea are the prokaryotes. Organisms from the different domains can be distinguished by a number of morphological and biochemical criteria known in the art. For example, differences in ribosomal RNA sequences, RNA polymerase structure, the presence or absence of introns, antibiotic sensitivity, the presence or absence of cell wall peptidoglycans and other cell wall components, the branched versus unbranched structures of membrane lipids, and the presence/absence of histones and histone-like proteins are used to assign an organism to the Bacteria or Archaea.

Examples of Bacteria include, but are not limited to, members of the phyla *Acidobacteria, Actinobacteria, Aquificae, Bacteroidetes, Chlamydiae, Chlorobi, Chloroflexi, Chrysiogenetes, Cyanobacteria, Deferribacteres, Deinococcus, Thermus, Dictyoglomi, Fibrobacteres, Firmicutes, Fusobacteria, Gemmatimonadetes, Lentisphaerae, Nitrospira, Planctomycetes, Proteobacteria, Spirochaetes, Tenericutes, Thermodesulfobacteria, Thermomicrobia, Thermotogae*, and *Verrucomicrobia*. Specific, non-limiting examples of Eubacteria include *Escherichia coli, Thermus thermophilus, Stenotrophomonas maltophilia, Kineococcus radiotolerans* and *Bacillus stearothermophilus*. Examples of Archaea include *Methanococcus jannaschii, Methanosarcina mazei, Methanobacterium thermoautotrophicum, Methanococcus maripaludis, Methanopyrus kandleri, Halobacterium halobium, Haloferax volcanii, Archaeoglobus fulgidus, Pyrococcus fit riosus, Pyrococcus horikoshii, Pyrobaculum aerophilum, Pyrococcus abyssi, Sulfolobus solfataricus, Sulfolobus tokodaii, Aeuropyrum pernix, Thermoplasma acidophilum*, and *Thermoplasma volcanium*. Other specific examples of Bacteria can be found at www.bacterio.cict.fr/classifphyla.html#Acidobacteria#Acidobacteria (last accessed on May 22, 2007).

Biocrude: The term "Biocrude" generally refers to a composition partially or entirely produced by a microorganism, examples of which are disclosed herein. The biocrude may include hydrocarbons, hydrocarbon products, fatty acid esters, and/or aliphatic ketones. In certain embodiments, the microorganism is a recombinant microorganism. In other embodiments, the microorganism produces the biocrude from a substrate containing a fatty acyl chain, a hydrocarbon intermediate, or a fatty acid biosynthetic pathway product. In certain embodiments, the biocrude consists essentially of hydrocarbons and is substantially free of any compounds that include oxygen. For example, the biocrude may include at least about 90 wt %, more particularly at least about 95 wt %, preferably at least about 99 wt % hydrocarbons, based on the total weight of the biocrude. In certain examples, the biocrude may include less than about 1 wt %, preferably less than about 0.5 wt %, and most preferably less than about 0.25 wt % of compounds that include oxygen, based on the total weight of the biocrude.

Biofuel: The term "biofuel" refers to any fuel derived from biomass, including, for example, carbohydrates, organisms, such as plants, fermentation waste, or metabolic byproducts, such as manure from cows. It is a renewable energy source, unlike other natural resources, such as petroleum, coal and nuclear fuels. Agricultural products specifically grown for use as biofuels and waste from industry, agriculture, forestry, and households, including straw, lumber, manure, sewage, garbage and food leftovers can be used for the production of biofuel. For example, biofuels are inclusive of transportation fuels, heating fuels, and electricity-generating fuels.

Biosynthetic pathway: The term "biosynthetic pathway" also referred to as "metabolic pathway", refers to a set of anabolic or catabolic biochemical reactions for converting (transmuting) one chemical species into another. For instance, an antibiotic biosynthetic pathway refers to the set of biochemical reactions which convert primary metabolites to antibiotic intermediates and then to antibiotics. A hydrocarbon biosynthetic pathway refers to the set of biochemical reactions which convert primary metabolites to hydrocarbon intermediates and then to hydrocarbons. Exemplary biosynthetic pathways include, for example the pathway associated with the production of fatty acids.

Carbon length: Defined carbon length (e.g., $C_{18}$) as used herein refers to the number of carbon atoms in a carbon straight chain (not including the carbons in the branch moieties). For example, the number of carbons in a substrate containing a fatty acyl chain, alkenes, fatty acids, olefins, and other hydrocarbons or hydrocarbon products described herein.

Carbon source: The term "carbon source" generally refers to a substrate, compound or mixtures of compounds and/or substrates suitable to be used as a source of carbon for bacterial or simple eukaryotic cell growth. Carbon sources may be in various forms, including, but not limited to polymers, carbohydrates, such as cellulosic material including oligosaccharides and lignocellulose, acids, alcohols, aldehydes, ketones, amino acids, peptides, etc., or mixtures thereof. These include, for example, various monosaccharides, such as glucose or sucrose, oligosaccharides, polysaccharides, saturated or unsaturated fatty acids, succinate, lactate, acetate, ethanol, etc., or mixtures thereof. In illustrative examples, the glucose can be produced from corn, the sucrose can be produced from cane sugar or soybean sugar, and the cellulosic material can be produced from parts of a plant (e.g., grasses, such as switchgrass), such as leaves, stems, stalks, bark, etc., or mixtures thereof.

Conditions that permit production: Any fermentation or culturing conditions that allow a microorganism to produce a desired product, such as a substrate containing a fatty acyl chain or hydrocarbon intermediate. Such conditions usually include, but are not limited to, temperature ranges, levels of aeration, and media selection that, when combined, allow the microorganism to grow and produce the desired product. Exemplary mediums include, but are not limited to, broths or gels. Generally, the medium includes a carbon source (such as glucose, fructose, cellulose, or the like) that can be metabolized by the microorganism directly, or enzymes can be used in the medium to facilitate metabolization of the carbon source. To determine if culture conditions permit product production, the microorganism can be cultured for about 2, 4, 6, 8, 12, 24, 36, 48 or 72 hours and a sample can be obtained and analyzed. For example, the cells in the sample, or the medium in which the cells were grown, can be tested for the presence of the desired product. When testing for the presence of a product, assays can be used, such as those provided in the Examples below.

Conservative variant: As used herein, the term "conservative variant" refers to a peptide or amino acid sequence that deviates from another amino acid sequence only in the substitution of one or several amino acids for amino acids having similar biochemical properties (called conservative substitutions). Conservative amino acid substitutions are likely to have minimal impact on the activity of the resultant protein. Further information about conservative substitutions can be found, for instance, in Ben Bassat et al. (*J. Bacteriol.,* 169: 751-757, 1987), O'Regan et al. (*Gene,* 77:237-251, 1989), Sahin-Toth et al. (*Protein Sci.,* 3:240-247, 1994), Hochuli et al. (*Bio/Technology,* 6:1321-1325, 1988) and in widely used textbooks of genetics and molecular biology.

Table 1, below, shows amino acids (right column) that can be substituted for an original amino acid (left column) in a protein. These substitutions are examples of conservative substitutions which can be used to create conservative variants.

TABLE 1

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

The amino acid substitutions which, in general, are expected to produce the greatest changes in protein properties will be non-conservative. For instance, changes in which: (a) a hydrophilic amino acid, for instance seryl (serine) or threonyl (threonine), is substituted for (or by) a hydrophobic amino acid, for instance leucyl (leucine), isoleucyl, phenylalanyl, valyl or alanyl; (b) a cysteine or proline is substituted for (or by) any other amino acid; (c) an amino acid having an electropositive side chain, for instance lysyl, arginyl, or histadyl, is substituted for (or by) an amino acid having an electronegative side chain, for instance glutamyl or aspartyl; or (d) an amino acid having a bulky side chain, for instance phenylalanine, is substituted for (or by) one not having a side chain, for instance glycine.

Deletion: The removal of one or more nucleotides from a nucleic acid molecule or one or more amino acids from a protein, wherein the regions on either side of the respective nucleic acid or protein are joined together. Deoxyribonucleic acid (DNA): A long chain polynucleotide that includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acids. The term codon is also used to describe the corresponding three nucleotides in the mRNA molecule that is translated into an amino acid.

Encode: As used herein, the term "encode" refers to any process whereby the information in a polymeric macromolecule or sequence is used to direct the production of a second molecule or sequence that is different from the polymeric macromolecule or sequence. As used herein, the term is construed broadly and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in a first molecule is used to direct the production of a second molecule that has a different chemical nature from the first molecule. For example, a DNA molecule can encode an RNA molecule (for instance, by the process of transcription incorporating a DNA-dependent RNA polymerase enzyme). Also, an RNA molecule can encode a peptide, as in the process of translation. When used to describe the process of translation, the term "encode" also extends to the triplet codon that encodes an amino acid. In some aspects, an RNA molecule can encode a DNA molecule, for instance, by the process of reverse transcription incorporating an RNA-dependent DNA polymerase. In another aspect, a DNA molecule can encode a peptide, where it is understood that "encode" as used in that case incorporates both the processes of transcription and translation.

Endogenous: As used herein with reference to a nucleic acid molecule and a particular cell or microorganism refers to a nucleic acid sequence or peptide that is in the cell or microorganism and was not introduced into the cell or microorganism using recombinant engineering techniques. For example, a gene that was present in the cell when the cell was originally isolated from nature. A gene is still considered endogenous if the control sequences, such as a promoter or enhancer sequences that activate transcription or translation have been altered through recombinant techniques.

Exogenous: As used herein with reference to a nucleic acid molecule and a particular cell or microorganism refers to any nucleic acid molecule that does not originate from that particular cell or microorganism as found in nature. For example, an exogenous nucleic acid molecule can be inserted within the genomic DNA of a microorganism or it can be an extra chromosomal nucleic acid molecule that is introduced into the microorganism. Thus, a non-naturally-occurring nucleic acid molecule is considered to be exogenous to a cell once introduced into the cell. A nucleic acid molecule that is naturally-occurring also can be exogenous to a particular cell. For example, an entire nucleic acid molecule isolated from an *E. coli* DH5alpha cell is an exogenous nucleic acid molecule with respect to a second *E. coli* DH5alpha cell once that nucleic acid molecule is introduced into the cell of the second *E. coli* DH5alpha cell, even though both cells are DH5alpha cells.

Fatty acid compound: The term "fatty acid" refers to a carboxylic acid that is composed of a chain of hydrocarbon groups containing greater than 4 carbon atoms and characterized by a terminal carboxyl group (—COOH). An unsaturated fatty acid includes at least one double bond between the carbon atoms in the hydrocarbon chain. A branched fatty acid includes at least one branch point. Fatty acids can also be substituted with additional functional groups, such as, but not limited to, hydroxyl groups (—OH) and cyclopropyl groups.

Fermentation Media: Any medium that supports microorganism life (for instance, a microorganism that is actively metabolizing carbon). A fermentation medium usually contains a carbon source and can be a liquid such as a broth or a gel. The carbon source can be anything that can be utilized, with or without additional enzymes, by the microorganism to support life.

Fungi: A kingdom of organisms within the Eukarya domain. They are heterotrophic and digest their food externally, absorbing nutrient molecules into their cells. Yeasts, molds, and mushrooms are examples of fungi. The major phyla of fungi include *Chytridiomycota, Zygomycota, Glomeromycota, Ascomycota*, and *Basidiomycota*.

The *Chytridiomycota* are commonly known as chytrids. These fungi produce zoospores that are capable of moving on their own through liquid menstrua by simple flagella. The *Zygomycota* are known as zygomycetes and reproduce sexually with meiospores called zygospores and asexually with sporangiospores. *Rhizopus stolonifer, Pilobolus, Mucor, Rhizomucor*, and *Rhizopus* are *Zygomycota*.

Specific, non-limiting examples of fungi that are useful in the disclosed methods include *Saccharomyces cerevisiae, Aspergillus, Trichoderma, Neurospora, Fusarium*, and *Chrysosporium*.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a cell, tissue or subject to an agent that increases or decreases gene expression. Expression of a gene also can be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression can be measured at the RNA level or the protein level and by any method known in the art, including, without limitation, Northern blot, RT-PCR, Western blot, or in vitro, in situ, or in vivo protein activity assay(s).

Homolog: Any gene that is related to a reference gene by descent from a common ancestral DNA sequence. The term "ortholog" refers to homologs in different species that evolved from a common ancestral gene by speciation. Typically, orthologs retain the same or similar function despite differences in their primary structure, which can be due to mutations. The term "paralog" refers to homologs in the same species that evolved by genetic duplication of a common ancestral gene. In many cases, paralogs exhibit related, but not always identical, functions. As used herein, the term "homolog" encompasses both "orthologs" and "paralogs". To the extent that a particular species has evolved multiple related genes from an ancestral DNA sequence shared with another species, the term ortholog can encompass the term paralog.

Hydrocarbon: A "hydrocarbon" generally refers to a chemical compound that consists of the elements carbon (C) and hydrogen (H). They all contain a carbon backbone and atoms of hydrogen attached to that backbone. There are essentially three types of hydrocarbons: (1) aromatic hydrocarbons, which have at least one aromatic ring; (2) saturated hydrocarbons, also known as alkanes, which do not have double or triple bonds or aromatic moieties; (3) unsaturated hydrocarbons, which have one or more double or triple bonds between carbon atoms.

Hydrocarbon feedstock: "Hydrocarbon feedstock" refers to a composition that consists essentially of hydrocarbons. The feedstock may be subjected to cracking or can be blended with other types of crude oil, such as petroleum, prior to the cracking reaction or after the cracking reaction. The hydrocarbon feedstock may be produced by microorganisms disclosed herein.

Hydrocarbon intermediate: Is an intermediate formed by any peptide or chemical conversion that can subsequently be converted either through biological conversion or chemical conversion to a hydrocarbon. Typically the intermediates include atoms other than hydrogen and carbon, such as oxygen, and thus are not considered to be hydrocarbons. Intermediates produced in certain embodiments include intermediates, which may be formed, for example by the enzyme-mediated condensation of fatty acids and/or fatty acid biosynthetic pathway products. In some non-limiting examples, a hydrocarbon intermediate is any product formed by the activity of OleA, OleC, or OleD. In one embodiment, certain hydrocarbon intermediates may be represented by the formula.

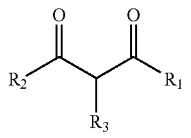

With reference to the formula above, $R_1$ typically, along with the carbonyl moiety to which it is bonded forms an activated ester group. Particular examples of $R_1$ groups include those that form thioesters, such as Coenzyme A, acyl carrier proteins, and phosphate esters, such as AMP or inorganic pyrophosphate (PPi).

With continued reference to the bis-carbonyl structure (examples of such structures may be referred to herein as "β-ketoesters") above, $R_2$ typically is derived from the hydrocarbon chain of a fatty acid or fatty acid derivative. As such, $R_2$ typically is an optionally substituted aliphatic hydrocarbon chain, optionally containing one or more, such as one, two or three, sites of unsaturation. Typically, such sites of unsaturation are alkenes, which independently may be for each alkene in either the cis or trans ((Z) or (E)) configuration. Such sites of unsaturation may be in any position, including, for example, in a terminal position. Such terminal alkenes, typically, are monosubstituted alkenes.

Similarly, $R_3$ typically is derived from the hydrocarbon chain of a fatty acid or fatty acid derivative. As such, $R_2$ and $R_3$ may be the same or different. Typically, $R_3$ is an optionally substituted aliphatic hydrocarbon chain, optionally containing one or more, such as one, two or three, sites of unsaturation. Typically, such sites of unsaturation are alkenes, which independently may be for each alkene in either the cis or trans ((Z) or (E)) configuration. Such sites of unsaturation may be in any position, including, for example, in a terminal position. As further noted above, $R_2$ and/or $R_3$ may optionally be substituted. One example of such substitutions includes branching aliphatic groups, wherein one hydrogen on the hydrocarbon chain is replaced with an aliphatic group, typically a lower aliphatic group, such as a lower alkyl group.

As used herein, the term "lower alkyl" group refers to a saturated branched or unbranched hydrocarbon having from about 1 to about 10 carbon atoms. Exemplary substituted hydrocarbon chains have a lower alkyl group, such as a methyl or ethyl group substituted for a hydrogen atom.

Other intermediates may be produced from those described above, for example, some intermediates may be represented by the formula

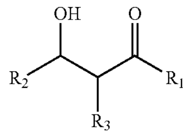

wherein $R_1$, $R_2$ and $R_3$ are as described above. Such compounds can be referred to as "β-hydroxy esters."

Still other intermediates include precursors to the β-hydroxy ester compounds described above. In one embodiment, such a precursor is an aliphatic aldehyde compound, examples of which can be represented by the formula

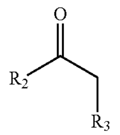

wherein $R_2$ and $R_3$ are as described above. Aliphatic aldehyde compounds may react with a fatty acid or fatty acid biosynthetic pathway product, such as an activated ester compound, to produce β-hydroxy esters, such as those of the formula

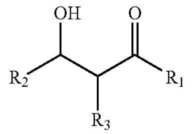

In certain embodiments, examples of the above-described structures are converted to compounds of the structure

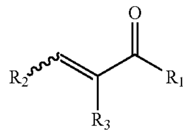
or
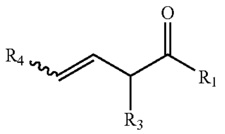

wherein $R_1$, $R_2$ and $R_3$ are as described above and $R_4$ is an optionally substituted aliphatic hydrocarbon chain, optionally containing one or more, such as one, two or three, sites of unsaturation. Typically such sites of unsaturation are alkenes, which independently may be for each alkene in either the cis or trans ((Z) or (E)) configuration. Such compounds can be referred to as "α,β-unsaturated esters" or "β,γ-unsaturated esters," respectively. As indicated in the above formulas, the α,β- and β,γ-alkene groups also independently may be in either the cis or trans ((Z) or (E)) configuration. Without being limited to any particular theory it currently is believed that such α,β-unsaturated esters and/or β,γ-unsaturated esters may be formed in the presence of OleD, OleC, or both.

Examples of the above-described intermediate compounds are, in some embodiments, converted to hydrocarbon product compounds, such as including, without limitation products of the formula

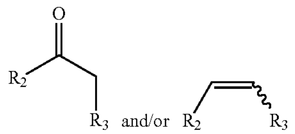

wherein $R_2$ and $R_3$ are as described above. Such compounds are referred to as ketones and olefins, respectively.

Hydrocarbon product: "Hydrocarbon product" generally refers to a chemical compound that is primarily a hydrocarbon (i.e., contains primarily the elements of carbon and hydrogen), but may also contain one or more atoms other than carbon and hydrogen, including heteroatoms, such as oxygen, nitrogen, or sulfur. These include, but are not limited to, fatty alcohols, thiols, esters, waxes, thioesters, ethers, epoxides, aliphatic ketones, acids, and aldehydes, containing two or more carbon atoms, typically from about 2 to about 60 carbon atoms, from about 10 to about 50 carbon atoms, or from about 15 to about 40 atoms, including all stereoisomers.

Hydrocarbon synthase activity: The activity of one or more peptides that causes the conversion of a fatty acyl chain containing product to a hydrocarbon.

Isolated: An "isolated" biological component (e.g., a nucleic acid molecule, peptide, or cell) is a biological component which has been substantially purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression recombinant microorganism for a recombinant peptide or nucleic acid molecule). The term "isolated nucleic acid" encompasses nucleic acid molecules purified by standard nucleic acid molecule purification methods. The term also embraces nucleic acid molecules prepared by recombinant expression in a recombinant microorganism, as well as chemically synthesized nucleic acid molecules.

Microorganism: A member of the prokaryotic or eukaryotic microbial species from the domains Archaea, Bacteria, and Eucarya, the latter including yeast and filamentous fungi, protozoa, algae, or higher Protista. The terms "microbial cells" and "microbes" are used interchangeably with the term microorganism.

Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid sequence", "nucleic acid" and "polynucleotide." A nucleic acid molecule is usually at least about 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules can be modified chemically or biochemically or can contain non-natural or derivatized nucleotide bases, as will be readily appreciated. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, peptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

Olefin: An "olefin" generally refers to alkenes and cycloalkenes and the corresponding polyenes.

Open reading frame (ORF): A contiguous series of nucleotide triplets coding for amino acids. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. Configurations of separate genes that are transcribed in tandem as a single messenger RNA are denoted as operons. Thus, placing genes in close proximity, for example in a plasmid vector, under the transcriptional regulation of a single promoter, constitutes a synthetic operon.

Over express: When a peptide is present in a greater concentration in a recombinant microorganism compared to its concentration in a non-recombinant recombinant microorganism of the same species. Over expression can be accomplished using any method known in the art. For example, over expression can be caused by altering the control sequences in the genomic DNA of a recombinant microorganism, modifying one or more genes involved in the regulation of gene expression (e.g., deleting a repressor gene or producing an active activator), introducing one or more coding sequences into the genomic DNA, amplifying the gene at a chromosomal location (e.g., tandem repeats), introducing an extra chromosomal nucleic acid sequence, increasing the stability of the RNA transcribed via introduction of stabilizing sequences, and combinations thereof. Over expression also includes elevated rates of translation of a gene compared to the endogenous translation rate for that gene. Methods of testing for over expression are well known in the art, for example transcribed RNA levels can be assessed using rtPCR and protein levels can be assessed using SDS page gel analysis.

Plasmid: A DNA molecule separate from chromosomal DNA and capable of autonomous replication. It is typically circular and double-stranded, and usually occurs in bacteria, and sometimes in eukaryotic organisms (for instance, the 2-micrometer-ring in *Saccharomyces cerevisiae*). The size of plasmids can vary from 1 to over 400 kilobase pairs. Plasmids often contain genes or gene cassettes that confer a selective advantage to the bacterium (or other cell) harboring them, such as the ability to make the bacterium (or other cell) antibiotic resistant.

Plasmids used in genetic engineering can be used as vectors. They can be used to transfer genes from one organism to another, and typically contain a genetic marker conferring a phenotype that can be selected for or against. Most also contain a polylinker or multiple cloning site, which is a short region containing several commonly used restriction sites allowing for the easy insertion of DNA fragments at this location. Specific, non-limiting examples of plasmids include pCLHF, pCLNCX (Imgenex), pCLHF-GFP-TAG, pSUPER (OligoEngine), pEYCUA-YRS, pBluescript II KS (Stratagene), pCDNA3 (Invitrogen), pCDNA3.1(+) (Invitrogen), pET-21b(+) Novagen/Merck Biosciences, San. Diego, Calif.), pCOLADuet-1 (EMD Chemicals Inc., an Affiliate of Merck KGaA, Darmstadt, Germany), pCMV SPORT6.1 (Gibco BRL, Gaithersburg, Md.), and pCDFDuet-1 (EMD Chemicals Inc., an Affiliate of Merck KGaA, Darmstadt, Germany).

Primers: Short nucleic acids, for example DNA oligonucleotides 10 nucleotides or more in length, which are annealed to a complementary target DNA strand by nucleic acid hybridization to form a hybrid between the primer and the target DNA strand and then extended along the target DNA strand by a DNA polymerase enzyme. Primer pairs can be used for amplification of a nucleic acid sequence, for example, by using the polymerase chain reaction (PCR) or other nucleic-acid amplification methods known in the art.

Probes and primers, as used herein, typically include, for example, at least about 12 contiguous nucleotides of a known sequence. In order to enhance specificity, longer probes and primers also can be employed, such as probes and primers that include at least about 15, 20, 30, 40, 50, or more consecutive nucleotides of the disclosed nucleic acid sequences.

Methods for preparing and using probes and primers are described in, for example, Sambrook et al., *Molecular Cloning: A Laboratory Manual,* 3rd ed., vol. 1-3, Cold Spring Harbor, N.Y., 2000; Ausubel et al., *Current Protocols in Molecular Biology*, Greene Publ. Assoc. & Wiley-Intersciences, 1987; Innis et al., *PCR Protocols, A Guide to Methods and Applications,* 1990. PCR primer pairs can be derived from a known sequence, for example, by using computer programs intended for that purpose such as Primer (Version 0.5, 1991, Whitehead Institute for Biomedical Research, Cambridge, Mass.).

Promoter: A region of DNA that generally is located upstream (within the 5' flanking region of a gene) that is needed for transcription. Promoters permit the proper activation or repression of the gene which they control. A promoter contains specific sequences that are recognized by transcription factors. These factors bind to the promoter DNA sequences and result in the recruitment of RNA polymerase, the enzyme that synthesizes the RNA from the coding region of the gene.

Promoters are untranslated sequences located generally within 100 to 1000 base pairs (bp) upstream from the start codon of a structural gene that regulate the transcription and translation of nucleic acid sequences under their control. Promoters are generally either inducible or constitutive.

Inducible promoters are promoters that initiate increased levels of transcription from DNA under their control in response to some change in the environment, for instance the presence or absence of a nutrient or a change in temperature. Constitutive promoters, in contrast, maintain a relatively constant level of transcription. In addition, useful promoters can also confer appropriate cellular and temporal specificity. Such promoters include those that are developmentally-regulated and/or cell-specific.

A nucleic acid sequence is operably linked to another nucleic acid sequence when it is placed into a functional relationship with the other nucleic acid sequence. For example, DNA for a presequence or secretory leader is operatively linked to DNA for a polypeptide if it is expressed as a preprotein that participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading frame.

Purified: The term purified does not require absolute purity; rather, it is intended as a relative term. Thus, for example, a purified product is one in which the product is more concentrated than the product is in its environment within a cell. For example, a purified hydrocarbon is one that is substantially separated from cellular components (nucleic acids, lipids, carbohydrates, and peptides) that can accompany it. In another example, a purified hydrocarbon is one in which the hydrocarbon is substantially-free from contaminants, such as those that might be present following fermentation.

In one example, a hydrocarbon is purified when at least about 50% by weight of a sample is composed of the hydrocarbon. In other examples, a hydrocarbon is purified when at least about 60%, 70%, 80%, 85%, 90%, 92%, 95%, 98%, or 99% or more by weight of a sample is composed of the hydrocarbon.

Recombinant nucleic acid: A "recombinant nucleic acid" is a nucleic acid sequence that is not naturally occurring in the host cell, has a nucleic acid sequence that is made by an artificial combination of two otherwise separate segments of nucleotide sequences, or a non-native nucleotide sequence that is placed next to a native DNA sequence. This artificial combination is often accomplished by chemical synthesis or, more commonly, by the artificial manipulation of isolated segments of nucleic acids, for instance by genetic engineering techniques such as those described in, for example, Sambrook et al., *Molecular Cloning: A Laboratory Manual,* 3rd ed., vol. 1-3, Cold Spring Harbor, N.Y., 2000. The term recombinant also includes nucleic acids that have been altered solely by addition, substitution, or deletion of a portion of the nucleic acid. Frequently, a recombinant nucleic acid can include a nucleic acid sequence operably linked to a promoter sequence. Such a recombinant nucleic acid can be part of a vector used to transform a cell. Recombinant microorganisms comprise one of more recombinant nucleic acid sequences.

Reporter: An agent that can be used to identify and/or select target components of a system of interest. For example, a reporter can include a protein, for instance, an enzyme, that confers antibiotic resistance or sensitivity (for instance, 3-lactamase, chloramphenicol acetyltransferase (CAT), and the like), a fluorescent screening marker (for instance, green fluorescent protein (GFP), YFP, EGFP, RFP, etc.), a luminescent marker (for instance, a firefly luciferase protein), an affinity based screening marker, or positive or negative selectable marker genes such as lacZ, 3-gal/lacZ (13-galactosidase), ADH (alcohol dehydrogenase), his3, ura3, leu2, lys2, or the like.

A reporter gene is a nucleic acid sequence that encodes an easily assayed product (for instance, firefly luciferase, CAT, or β-galactosidase). A reporter gene can be operably linked to a regulatory control sequence and transduced into cells. If the regulatory control sequence is transcriptionally active in a particular cell type, the reporter gene product normally will be expressed in such cells and its activity can be measured using techniques known in the art. The activity of a reporter gene product can be used, for example, to assess the transcriptional activity of an operably linked regulatory control sequence. In addition, the activity of a reporter gene can be assayed for in a small scale experiment. In some cases, the product of a reported gene can be used itself as a reporter of the reporter gene's own activity.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene* 73:237-244, 1988; Higgins & Sharp, *CABIOS* 5:151-153, 1989; Corpet et al., *Nucleic Acids Research* 16:10881-10890, 1988; Huang, et al., *CABIOS* 8:155-165, 1992; and Pearson et al., *Methods in Molecular Biology* 24:307-331, 1994. Altschul et al., *J. Mol. Biol.* 215: 403-410, 1990, presents a detailed consideration of sequence alignment methods and homology calculations.

The NCBI Basic Local Alignment Search Tool (BLAST™; Altschul et al., *J. Mol. Biol.* 215:403-410, 1990) is available from several sources, including the National Center for Biotechnology Information (NCBI, Bethesda, Md.), for use in connection with the sequence analysis programs blastp, blastn, blastx, tblastn and tblastx. BLAST™ can be accessed on the Internet at the NCBI website. As used herein, sequence identity is commonly determined with the BLAST™ software set to default parameters. For instance, blastn (version 2.0) software can be used to determine sequence identity between two nucleic acid sequences using default parameters (expect=10, matrix=BLOSUM62, filter=DUST (Tatusov and Lipmann, in preparation as of Dec. 1, 1999; and Hancock and Armstrong, *Comput. Appl. Biosci.* 10:67-70, 1994), gap existence cost=11, per residue gap cost=1, and lambda ratio=0.85). For comparison of two polypeptides, blastp (version 2.0) software can be used with default parameters (expect 10, filter=SEG (Wootton and Federhen, *Computers in Chemistry* 17:149-163, 1993), matrix=BLOSUM62, gap existence cost=11, per residue gap cost=1, lambda=0.85).

For comparisons of amino acid sequences of greater than about 30 amino acids, the "Blast 2 sequences" function of the BLAST™ program is employed using the default BLOSUM62 matrix set to default parameters, (gap existence cost of 11 and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties).

Alternatively, a person of ordinary skill in the art could use another alignment algorithm well known in the art, for example ClustalW with default parameters.

Substantially uniform point of unsaturation: The term "substantially uniform point of unsaturation" means that for a given hydrocarbon or hydrocarbon product (e.g., a $C_{27}$ compound) in the biocrude or hydrocarbon feedstock the carbon-carbon double bond is present at the same carbon atom position in the hydrocarbon chain for substantially all (e.g., at least about 90%) molecules of that particular compound.

Substrate containing a fatty acyl chain: The term "substrate containing a fatty acyl chain" includes substrates containing one or more fatty acyl chains. A fatty acyl chain refers to a fatty acid linked by an ester, thioester, or phosphoester linkage to another small molecule or protein. For example, a fatty acyl chain can be linked to either an acyl carrier protein or coenzyme A through a thioester linkage. In another example, a carboxylic acid can be linked to a phosphate through a phosphoester linkage.

A substrate containing a fatty acyl chain can be used as a substrate by enzymes which produce biocrude or by enzymes that produce intermediates that may eventually be converted to biocrude. In one embodiment, a substrate containing a fatty acyl chain is an intermediate or product of the fatty acid biosynthetic pathway. The fatty acid biosynthetic pathway includes fatty acid synthase enzymes (FAS) that produce fatty acid biosynthetic pathway products. In some examples, the expression of these enzymes can be controlled to produce fatty acid biosynthetic pathway products having desired carbon chain characteristics.

Examples of a substrate containing a fatty acyl chain from the fatty acid biosynthetic pathway include, but are not limited to, acyl-ACP and fatty acid. In another embodiment, a substrate containing a fatty acyl chain can be derived from a "free" fatty acid. Examples of a substrate containing a fatty acyl chains derived from a fatty acid include, but are not limited to, an acyl-CoA, a fatty aldehyde, a hydrocarbon intermediate, such as an aliphatic ketone, a fatty alcohol, such as a short or long chain fatty alcohol, a fatty acid ester, including a wax, a phospholipid, a lipid A, and the like.

Target Nucleic Acid: A nucleic acid that hybridizes with a probe: The conditions under which hybridization occurs can vary with the size and sequence of the probe and the target sequence.

By way of illustration, a hybridization experiment can be performed by hybridization of a DNA probe (for example, a probe derived from the EPS 352 plasmid labeled with a chemiluminescent agent) to a target DNA molecule which has been electrophoresed in an agarose gel and transferred to a nitrocellulose membrane by Southern blotting (a technique well known in the art and described in Sambrook et al., *Molecular Cloning: A Laboratory Manual,* 3rd ed., vol. 1-3, Cold Spring Harbor, N.Y., 2000).

Hybridization with a radio-labeled probe is generally carried out in a solution of high ionic strength such as 6×SSC at a temperature that is 20° C.-25° C. below the melting temperature, $T_m$, described below. For such Southern hybridization experiments where the target DNA molecule on the Southern blot contains 10 ng of DNA or more, hybridization is typically carried out for 6-8 hours using 1-2 ng/mL radio-labeled probe. Following hybridization, the nitrocellulose filter is washed to remove background hybridization. The wash conditions should be as stringent as possible to remove background hybridization, but still to retain a specific hybridization signal. The term $T_m$ represents the temperature above which, under the prevailing ionic conditions, the radiolabeled probe molecule will not hybridize to its target DNA molecule. The $T_m$ of such a hybrid molecule can be estimated from the following equation:

$$T_m=81.5°\ C.-16.6\ (\log_{10}[Na^+])+0.41\ (\%\ G+C)-0.63\ (\%\ formamide)-(600/l)$$

Where l=the length of the hybrid in base pairs. This equation is valid for concentrations of $Na^+$ in the range of 0.01M to 0.4M, and it is less accurate for calculations of $T_m$ in solutions of higher $[Na^+]$. The equation is primarily valid for DNAs whose G+C content is in the range of 30% to 75%, and applies to hybrids greater than 100 nucleotides in length (the behavior of oligonucleotide probes is described in detail in Ch. 11 of Sambrook et al., 2000).

Generally hybridization wash conditions are classified into categories, for example very high stringency, high stringency, and low stringency. The conditions corresponding to these categories are provided below.

| | | | | | | |
|---|---|---|---|---|---|---|
| Very High Stringency (detects sequences that share at least 90% sequence identity) | | | | | | |
| Hybridization | in | 5x | SSC | at | 65° C. | 16 hours |
| Wash twice | in | 2x | SSC | at | Room temp. | 15 minutes each |
| Wash twice | in | 0.2x | SSC | at | 65° C. | 20 minutes each |
| High Stringency (detects sequences that share at least 80% sequence identity) | | | | | | |
| Hybridization | in | 3x | SSC | at | 65° C. | 16 hours |
| Wash twice | in | 2x | SSC | at | Room temp. | 15 minutes each |
| Wash twice | in | 0.5x | SSC | at | 55° C. | 20 minutes each |
| Low Stringency (detects sequences that share at least 50% sequence identity) | | | | | | |
| Hybridization | in | 3x | SSC | at | 65° C. | 16 hours |
| Wash twice | in | 2x | SSC | at | Room temp. | 20 minutes |

The above example is given entirely by way of theoretical illustration. One will appreciate that other hybridization techniques can be utilized and that variations in experimental conditions will necessitate alternative calculations for stringency.

Transcriptional regulatory sequence: The term "transcriptional regulatory sequence" is a generic term used to refer to DNA sequences, such as initiation signals, enhancers, and promoters that induce or control transcription of a gene or genes with which they are operably linked.

Transduction: The process by which genetic material, for instance, DNA or another nucleic acid molecule, is inserted into a cell. Common transduction techniques include the use of viral vectors (including bacteriophages), electroporation, and chemical reagents that increase cell permeability. Transfection and transformation are other terms for transduction, although these sometimes imply expression of the genetic material as well. The term transformed refers to a cell into which a nucleic acid molecule has been introduced by molecular biology techniques. The term encompasses all techniques by which a nucleic acid molecule might be introduced into such a cell, including transformation with plasmid vectors (for example, by electroporation, conjugation, transduction, or natural transformation), transfection with viral vectors, and introduction of naked DNA by electroporation, natural transformation, lipofection, and particle gun acceleration.

Transportation fuel: The term "transportation fuel" is inclusive of, but not limited to, jet fuel, gasoline, diesel, alcohols (e.g., ethanol), and biodiesel.

Vector: A nucleic acid molecule capable of transporting a non-vector nucleic acid sequence that has been introduced into the vector. One type of vector is a "plasmid," which refers to a circular double-stranded DNA into which non-plasmid DNA segments can be ligated. Other vectors include cosmids, bacterial artificial chromosomes (BAC) and yeast artificial chromosomes (YAC). Another type of vector is a viral vector, wherein additional DNA segments can be ligated into all or part of the viral genome. Certain vectors are capable of autonomous replication in a recombinant microorganism into which they are introduced (for example, vectors having a bacterial origin of replication replicate in bacterial hosts). Other vectors can be integrated into the genome of a recombinant microorganism upon introduction into the recombinant microorganism and are replicated along with the host genome. Some vectors contain expression control sequences (such as promoters) and are capable of directing the transcription of an expressible nucleic acid sequence that has been introduced into the vector. Such vectors are referred to as "expression vectors." A vector can also include one or more selectable marker genes and/or genetic elements known in the art.

"Comprising" means "including." For example, "comprising A or B" means "including A," "including B" or "including A and B." It is further understood that all base sizes or amino acid sizes and all molecular weight or molecular mass values given for nucleic acids or peptides are approximate and are provided for description.

"Optional" or "optionally" means that the subsequently described event or circumstance can, but need not, occur and that the description includes instances where said event or circumstance occurs and instances when it does not occur.

Suitable methods and materials for the practice and testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (See, for example, Sambrook et al., Molecular Cloning: A Laboratory Manual, 3rd ed., Cold Spring Harbor Laboratory Press, 2000; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999).

Where a range of values is provided, it is understood that each intervening value between the upper and lower limit of that range and any other stated or intervening value in that stated range is encompassed within the invention. Where the stated range includes one or both of the limits, ranges excluding either or both of those included limits are also included in the invention.

It must be noted that as used herein and in the appended claims, the singular forms "a," "an," and "the" include plural referents unless the context clearly dictates otherwise. Thus, for example, reference to "a biosynthetic intermediate" includes a plurality of such intermediates, reference to "a nucleic acid" includes a plurality of such nucleic acids, and reference to "the genetically modified recombinant microorganism" includes reference to one or more genetically modified recombinant microorganisms and equivalents thereof known to those skilled in the art, and so forth.

The term "or" refers to a single element of stated alternative elements or a combination of two or more elements, unless the context clearly indicates otherwise. For example, the phrase "hydrocarbon synthase activity or thioesterase activity" refers to hydrocarbon synthase activity, thioesterase activity, or a combination of both hydrocarbon synthase activity and thioesterase activity.

Additionally, throughout the specification a reference may be made using an abbreviated gene name or enzyme name. For example, fadD refers to a gene encoding an acyl-CoA synthetase (EC 6.2.1.3, 2.3.1.86). One of ordinary skill in the art will understand that such references include all genes or peptides having the same activity as fadD.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Before the present invention is further described, it is to be understood that this invention is not limited to particular embodiments described. It is also to be understood that the terminology used herein is for the purpose of describing particular embodiments only and is not intended to be limiting.

Other terms and definitions are defined throughout the text as necessary for providing a detailed description.

Disclosed herein are processes for producing fuels from renewable biocrude or hydrocarbon feedstocks. In one embodiment of the fuel-producing process, the biocrude or hydrocarbon feedstock includes at least one hydrocarbon, for example an unsaturated aliphatic hydrocarbon, produced by a recombinant microorganism. In one aspect, the fuel product produced from the process described herein can be tailored for use in producing jet fuel and/or automotive fuels, including gasoline and diesel. The fuel has many advantages over current biofuels, such as ethanol, butanol and triglyceride derived fatty acid ester-based "biodiesel." For example, the fuels produced as described herein may have a higher energy density than conventional biofuels. This translates into a higher miles per gallon rating for this fuel as compared with biodiesel, butanol or ethanol.

In one embodiment of the disclosed fuel-producing process, branched hydrocarbons are produced. Such branching can be achieved, for example, by incorporating branched chain fatty acids, hydrocarbon intermediates with a branched chain, or substrates having a branched fatty acyl chain into the fatty acid biosynthetic pathway. After further biosynthetic and/or chemical processing steps, the branched fatty acids, hydrocarbon intermediates with a branched chain, or substrates having a branched fatty acyl chain are converted into branched chain alkanes, alkenes and/or alkynes. The branched chain alkanes, alkenes and/or alkynes can then be further processed (e.g., cracked) to produce biofuels (e.g., transportation fuels). Such branched compounds may have advantageous properties.

Disclosed herein are host organisms that can be used to produce hydrocarbons from renewable resources such as cellulosic materials or other carbohydrates such as glucose. These host organisms can be used to produce hydrocarbons directly or they can be used to produce substrates containing fatty acyl chains, such as fatty acids, containing branch points, points of unsaturation, and combinations thereof. In some examples, the microorganisms described herein produce branched unsaturated fatty acids of defined carbon length.

In certain examples, the biocrude or hydrocarbon feedstock may include greater than about 50 wt %, greater than about 60 wt %, greater than about 70 wt %, or even greater than about 80 wt % $C_{18}$-$C_{36}$, $C_{19}$-$C_{35}$, $C_{18}$-$C_{22}$, $C_{19}$-$C_{31}$, or $C_{23}$-$C_{27}$, based on the total weight of the biocrude. The hydrocarbons in the biocrude or hydrocarbon feedstock may be aromatic compounds (e.g., benzene or naphthalene), saturated compounds, and or unsaturated compounds. The unsaturated compounds may include any number of unsaturated bonds per molecule, such as, for example, mono-unsaturated, di-unsaturated or tri-unsaturated compounds. In certain embodiments, the biocrude or hydrocarbon feedstock includes greater than at least about 80, more preferably at least about 85, 90, or 99 wt % alkenes, based on the total weight of the biocrude. The alkenes may be primarily (e.g., greater than 50 wt %, preferably greater than about 60, 70, 80, or 90 wt %) branched chain alkenes, primarily (e.g., greater than 50 wt %, preferably greater than 60, 70, 80, or 90 wt %) straight chain alkenes, or a mixture of branched chain alkenes and straight chain alkenes.

When such hydrocarbons include a site of unsaturation, typically, it is a substantially uniform site of unsaturation. Hence, upon cracking, transportation fuel components of rather uniform characteristics may be produced.

III. Production of Biocrude or Hydrocarbon Feedstocks

Disclosed are several methods of making biocrude or hydrocarbon feedstock from recombinant microorganisms. These microorganisms can be microorganisms that naturally produce biocrude, but that have been genetically engineered to produce greater amounts or structurally altered biocrude. In some examples, the microorganism that naturally produces biocrude is genetically engineered to contain one or more of the modifications described in FIG. 7.

The recombinant microorganisms described herein produce biocrude from substrates containing fatty acyl chains. The recombinant microorganisms can produce the substrates containing fatty acyl chains using a variety of different techniques. For example, the fatty acid biosynthetic pathway can be manipulated so that the host cell produces substrates containing fatty acyl chains. In another embodiment, the microorganism can be provided with a feedstock supplemented with substrates containing fatty acyl chains.

Figure 2:
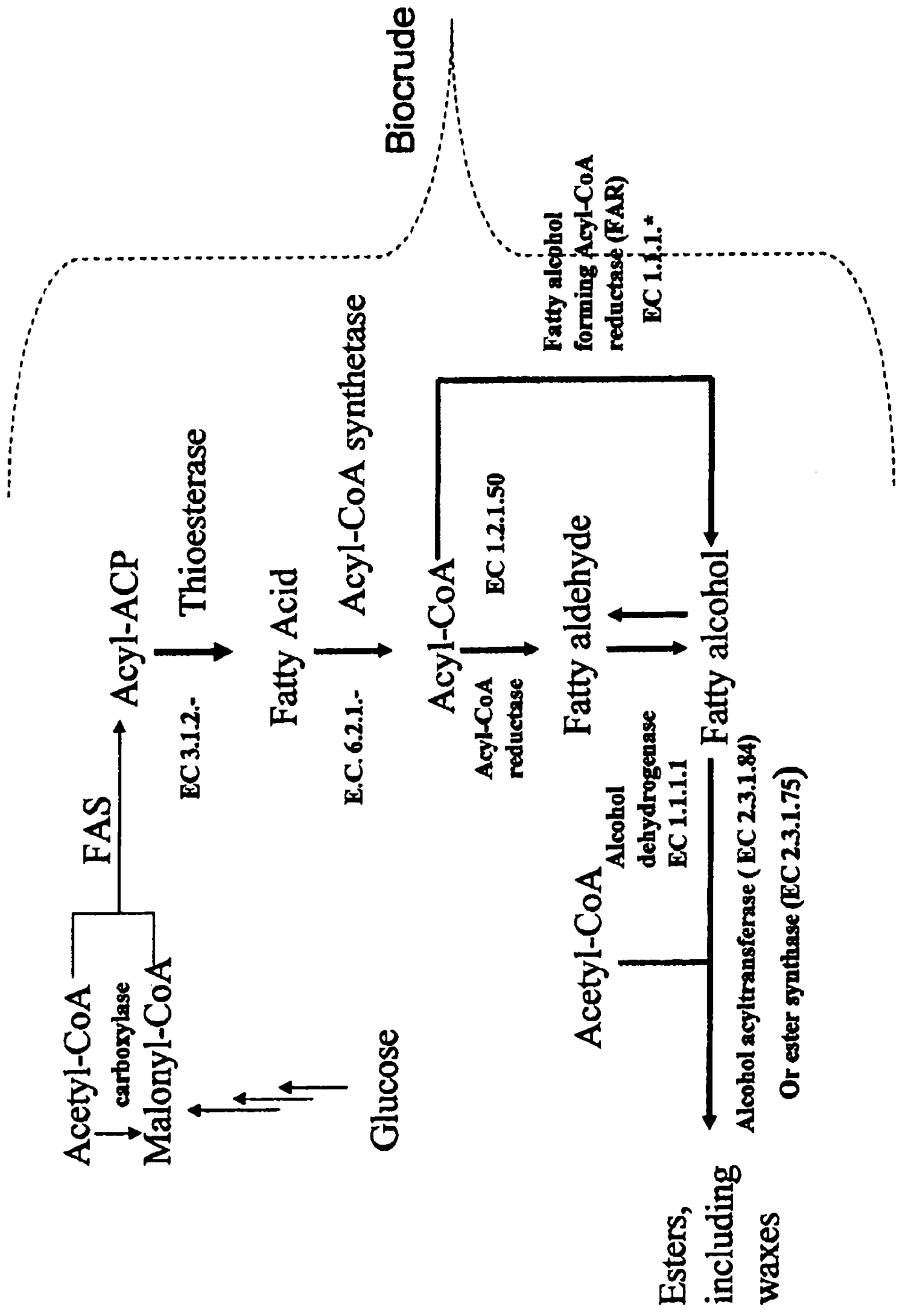
FIG. 2 shows a portion of the fatty acid biosynthetic pathway that produces fatty acid biosynthetic pathway products.

In some examples, the biocrude is made from fatty acid biosynthetic pathway products that include products made from the fatty acid biosynthetic pathway of the host organism. The fatty acid biosynthetic pathway includes fatty acid synthase enzymes (FAS) that produce fatty acid biosynthetic pathway products. FIG. 1 shows the exemplary enzymes in FAS and the fatty acid biosynthetic pathway products produced by those enzymes. FIG. 2 shows non-limiting examples of additional fatty acid biosynthetic pathway products and the enzymes that produce those products. In some examples, the expression of these enzymes can be controlled to produce fatty acid biosynthetic pathway products having desired carbon chain characteristics. Exemplary fatty acid biosynthetic pathway products include for example, acyl-ACPs, fatty acids, acyl-CoAs, fatty aldehydes, hydrocarbon intermediates such as aliphatic ketones, fatty alcohols, such as short and long chain alcohols, hydrocarbons, biocrude and fatty acid esters, including waxes. Fatty acid biosynthetic pathway product forming enzymes are enzymes that use as a substrate, or produce as a product, fatty acid biosynthetic pathway products. The fatty acid biosynthetic pathway products can be converted through one or more intermediates to biocrude.

In some examples, the recombinant microorganisms can be recombinant microorganisms that have been engineered to produce biocrude using exogenous enzyme activity. Also described herein is the surprising identification of several genes that are involved in the biosynthesis of hydrocarbons. Microorganisms (for instance fungal or bacterial cells) transformed with one or more of these genes can be used to produce hydrocarbons. The hydrocarbons can be derived from various substrates, such as fatty acyl chains and hydrocarbon intermediates. These recombinant microorganisms can also be engineered to alter their fatty acid biosynthetic pathway using the methods described below. These microorganisms permit the production of a wide range of specific olefin and aliphatic ketone products designed for particular applications. For instance, by selecting different host organisms and/or reaction substrates (for example, but not limited to fatty acids, fatty acyl CoAs, or aliphatic ketones), specific hydrocarbon products can be produced, including those having particular branches or levels of unsaturation.

In one embodiment, a cell (such as a bacterial cell or a fungal cell) is transformed with one or more of these genes or their homologs, and the cell is then cultured under conditions that permit the generation of biocrude. Cells from microorganisms that already include these genes can be transformed with additional recombinant nucleic acid sequences so that the genes are over expressed, thus producing biocrude that can include hydrocarbons and hydrocarbon intermediates.

In some examples, biocrude can be produced by over expressing or attenuating genes involved in the fatty acid biosynthetic pathway, such as those shown in FIG. 7. Recombinant microorganisms that are altered to increase fatty acid biosynthetic pathway production or to modify the structure of the fatty acids and fatty acid intermediates can be cultured under conditions sufficient to produce biocrude. The biocrude produced can be designed to include at least about 1, 2, 3, 4, 5, or more points of unsaturation. Similarly, the biocrude produced can be designed to include at least about 1, 2, 3, 4, 5, or more branch points. When such genetic modifications are combined with the expression of peptides having hydrocarbon synthase activity (endogenous activity or activity derived from the expression of recombinant sequences), the hydrocarbons and hydrocarbon intermediates can be designed to include at least about 1, 2, 3, 4, 5, or more points of unsaturation or at least about 1, 2, 3, 4, 5, or more branch points.

A. Recombinant Microorganisms Producing Substrates Containing Fatty Acyl Chains

Microorganisms that produce biocrude naturally (without genetic engineering) can be engineered to overproduce biocrude or produce biocrude with specific carbon chain characteristics by altering the fatty acid biosynthetic pathway as described herein. Exemplary microorganisms that are known to produce biocrude and can be engineered to alter biocrude production using the teachings provided herein include, but are not limited to, *Acinetobacter* spp., *Chloroflexus* spp., *Kineococcus radiotolerans, Stenotrophomonas maltophilia, Vibrio furnissii*, and cyanobacteria. These genetically engineered recombinant microorganisms are useful for producing biocrude.

In other examples, recombinant microorganisms that produce biocrude are engineered to over expresses one or more peptides selected from OleA, OleC, OleD and combinations thereof. These genes can be over expressed in microorganisms that naturally produce biocrude, such as those described above, or they can be over expressed in microorganisms that do not naturally produce biocrude.

Examples of recombinant microorganisms that over express a peptide include microorganisms that express nucleic acid sequences encoding OleA, OleC, OleD, or combinations thereof. Other examples include microorganisms that have had exogenous promoter sequences introduced upstream of the endogenous coding sequence of OleA, OleC, OleD, or combinations thereof. In some examples, over expression of one or more fatty acid biosynthetic pathway altering genes can be over-expressed in combination with OleA, OleC, or OleD.

The recombinant microorganisms described herein can also over express acyl-CoA synthetase (EC 6.2.1.3, 2.3.1.86), thioesterase (EC 3.1.2.-, 3.1.1.15, 3.1.2.14), acetyl-CoA carboxylase (EC 6.4.1.2, 6.3.4.14), an acyl-carrier protein, pyruvate dehydrogenase (EC 1.2.4.1), aldehyde decarbonylase (EC 4.1.99.5), beta-hydroxydecanoyl thioester dehydrase (EC 4.2.1.60), 3-oxoacyl-[acyl-carrier-protein]synthase I (EC 2.3.1.41), [acyl-carrier-protein]S-malonyltransferase (EC 2.3.1.39), 3-oxoacyl-[acyl-carrier protein]reductase (EC 1.1.1.100), 3-oxoacyl-[acyl-carrier-protein]synthase III (EC 2.3.1.180), enoyl-[acyl-carrier-protein]reductase (EC 1.3.1.9), (3R)-hydroxymyristol acyl carrier protein dehydratase (EC 4.2.1.-), lipase (EC 3.1.1.3), malonyl-CoA decarboxylase (EC 4.1.1.9, 4.1.1.41), aspartate 1-decarboxylase (EC 4.1.1.11), pantothenate kinase (EC 2.7.1.33), pyruvate dehydrogenase (EC 1.2.4.1), pyridine nucleotide transhydrogenase (EC 1.6.1.1) and combinations thereof.

In addition to over expressing one or more peptides to produce substrates containing fatty acyl chains, the recombinant microorganism can additionally have one or more peptides functionally deleted or attenuated. For example, one or more of the following acetate kinase (EC 2.7.2.1), alcohol dehydrogenase (EC 1.1.1.1, 1.2.1.10), 3-oxoacyl-[acyl-carrier-protein]synthase 11 (EC 2.3.1.179), FabR transcriptional repressor (accession NP_418398), acyl-CoA dehydrogenase (EC 1.3.99.3, 1.3.99.-), biosynthetic sn-glycerol 3-phosphate dehydrogenase (EC 1.1.1.94), lactate dehydrogenase (EC 1.1.1.28), formate acetyltransferase (EC 2.3.1.54), acyltransferase (EC 2.3.1.15), pyruvate oxidase (EC 1.2.2.2), phosphotransacetylase (EC 2.3.1.8) can be attenuated.

In some examples, the recombinant microorganism can produce branched products, including substrates containing fatty acyl chains, hydrocarbons and hydrocarbon intermediates. Recombinant microorganisms can be engineered to increase branching by over expressing a peptide selected from one or more components of the branch chain keto acid dehydrogenase complex (EC 1.2.4.4), branched-chain amino acid aminotransferase (EC 2.6.1.42), dihydrolipoamide dehydrogenase (E3) (EC 1.8.1.4), crotonyl-CoA reductase (EC 1.6.5.5, 1.1.1.1), isobutyryl-CoA mutase, subunit A (EC 5.4.99.2), isobutyryl-CoA mutase, subunit B (5.4.99.2), beta-ketoacyl-ACP synthase III (EC 2.3.1.180), beta-ketoacyl-ACP synthase II (EC 2.3.1.179), acyl-carrier protein (NP_823468), enoyl-CoA reductase (EC 1.3.1.34), enoyl-CoA isomerase (EC 4.2.1.-), and combinations thereof.

The saturation level of the substrate containing a fatty acyl chain, hydrocarbon and hydrocarbon intermediate can be altered by engineering the recombinant microorganism to over express a peptide selected from 3-oxoacyl-[acyl-carrier-protein]synthase I (EC 2.3.1.41), trans-2-enoyl-ACP reductase II (EC 1.3.1.9), enoyl-(acyl carrier protein) reductase (EC 1.3.1.9), trans-2, cis-3-decenoyl-ACP isomerase (4.2.1.17), acyl-CoA dehydrogenase (EC 1.3.99.3, 1.3.99.-) and combinations thereof.

In some examples a peptide having acyl CoA synthetase activity is over expressed. In other examples the acyl CoA synthetase can be fadD (NP_416319), fadK (NP_416216), fadD (YP_045024), fadD (NP_438551), BH3103 (NP_243969), yhfL (NP_388908), Pfl_4354 (YP_350082), EAV15023 (ZP_01520072), fadD1(NP_251989), fadD2 (NP_251990), fadD (YP_533919), RPC_4074 (YP_533919), fadD1 (NP_520978), fadDD35 (NP_217021), fadDD22 (NP_217464), PRK0059 (ZP_01644857) and combinations thereof.

Thioesterase expression can be controlled to alter the amount and/or the carbon chain length of the products including fatty acyl chains. For example, thioesterases such as tesA without leader sequence (AAC73596), tesB (AAC73555), fatB (Q41635, AAA34215), fatB2 (Q39513, AAC49269), fatB3 (AAC49269, AAC72881), fatB (Q39473, AAC49151), fatB [M141T] (CAA85388), fatA (NP 189147, NP 193041), fatA (AAC72883), fatA1 (AAL79361) or combinations thereof can be expressed or attenuated.

Recombinant microorganisms (for instance, bacterial, fungal or eukaryotic cells) are provided that are genetically engineered (for instance, transformed, transduced or transfected) with one or more nucleic acid molecules encoding one or more of OleA (e.g., SEQ ID NOS: 2, 4, 12, 18), OleC (e.g., SEQ ID NOS: 6, 14, 20), OleD (e.g., SEQ ID NOS: 8, 16, 22), OleB (e.g., SEQ ID NO: 10), or a variant or homolog of one or more of these sequences. These sequences can be expressed from vector constructs, directly from the chromosome after gene integration or from extrachromosomal arrays. For example, an OleA (e.g., SEQ ID NO: 2), OleC (e.g., SEQ ID NO: 6), or OleD (e.g., SEQ ID NO: 8) protein is encoded by a nucleic acid sequence that is operably linked to gene expression control elements that are functional in the desired recombinant microorganism, for instance a T7 promoter in *E. coli.*

Methods of expressing proteins in heterologous expression systems are well known in the art. Typically, a bacterial or yeast recombinant microorganism is transformed by natural transformation, electroporation, conjugation or transduction. The resulting expression construct can be either extrachromosomal, as with a plasmid, or integrated into the chromosome after recombination. In eukaryotic cells, typically, a recombinant microorganism is transfected with (or infected with a virus containing) an expression vector using any method suitable for the particular recombinant microorganism. Such transfection methods are also well known in the art and non limiting exemplary methods are described herein. The transformed recombinant microorganism is capable of expressing the protein encoded by the nucleic acid sequence in the expression cassette. In another embodiment, transient or stable transfection of the recombinant microorganism with one or more expression vectors could also be performed.

Many different types of recombinant microorganisms can be used to produce the proteins provided herein, such as bacteria, yeasts, fungi, insects, vertebrate cells (such as mammalian cells), and plant cells, including (as appropriate) primary cells and immortal cell lines. Numerous representatives of each cell type are commonly used and are available from a wide variety of commercial sources, including, for example, ATCC, Pharmacia, and Invitrogen.

Various yeast strains and yeast derived vectors are used commonly for the production of heterologous proteins. For instance, specific, non-limiting examples of suitable yeast cells include *Saccharomyces cerevisiae* cells, *Aspergillus* cells, *Trichoderma* cells, *Neurospora* cells, *Fusarium* cells, or *Chrysosporium* cells. In one specific, non-limiting example, *Pichia pastoris* expression systems, obtained from Invitrogen (Carlsbad, Calif.), can be used to produce an OleA (e.g., SEQ ID NOS: 2, 4, 12, 18), OleC (e.g., SEQ ID NOS: 6, 14, 20), or OleD (e.g., SEQ ID NOS: 8, 16, 22) peptide. Such systems include suitable *Pichia pastoris* strains, vectors, reagents, transformants, sequencing primers, and media. For example, available strains include, but are not limited to, KM71H (a prototrophic strain), SMD1168H (a prototrophic strain), and SMD1168 (a pep4 mutant strain) (Invitrogen).

*Saccharomyces cerevisiae* is another species of yeast commonly used as a host. The plasmid YRp7 (Stinchcomb et al., *Nature,* 282:39, 1979; Kingsman et al., *Gene,* 7:141, 1979; Tschemper et al., *Gene,* 10:157, 1980) is commonly used as an expression vector in a mutant *Saccharomyces* which cannot produce tryptophan. This plasmid contains the trp1 gene which when transformed into the mutant strain of yeast allows the mutant strain of yeast to produce tryptophan and grow in the absence of tryptophan. Examples of host strains where the trp1 gene can be used as a selection marker include, but are not limited to, such as ATCC No. 44,076 and PEP4-1 (Jones, *Genetics,* 85:12, 1977). The presence of the trp1 lesion in the yeast recombinant microorganism genome provides an effective characteristic for detecting transformation by growth in the absence of tryptophan.

Yeast recombinant microorganisms can be transformed using the polyethylene glycol method, as described by Hinnen (*Proc. Natl. Acad. Sci. USA,* 75:1929, 1978). Additional yeast transformation protocols are set forth in Gietz et al. (*Nucl. Acids Res.,* 20(17):1425, 1992) and Reeves et al. (*FEMS,* 99(2-3):193-197, 1992).

In the construction of suitable expression vectors, the termination sequences associated with these genes are also ligated into the 3' region of the sequence desired to be expressed Any plasmid vector containing a yeast-compatible promoter capable of transcribing a nucleic acid sequence encoding a prokaryotic tRNA, an origin of replication, and a termination sequence, is suitable.

Other suitable recombinant microorganisms are bacterial cells. Specific, non-limiting examples of suitable bacterial phyla which could be recombinant microorganisms include *Acidobacteria, Actinobacteria, Aquificae, Bacteroidetes, Chlamydiae, Chlorobi, Chloroflexi Chrysiogenetes, Cyanobacteria, Deferribacteres, Deinococcus, Thermus, Dictyoglomi, Fibrobacteres, Firmicutes, Fusobacteria, Gemmatimonadetes, Lentisphaerae, Nitrospira, Planctomycetes, Proteobacteria, Spirochaetes, Tenericutes, Thermodesulfobacteria, Thermomicrobia, Thermotogae*, and *Verrucomicrobia*. Specific, non-limiting examples, of bacterial species which could be used as recombinant microorganisms include *Escherichia coli, Thermus thermophilus, Stenotrophomonas maltophilia, Kineococcus radiotolerans, Bacillus stearothermophilus, Methanococcus jannaschii, Methanosarcina mazei, Methanobacterium thermoautotrophicum, Methanococcus maripaludis, Methanopyrus kandleri, Halobacterium* such as *Haloferax volcanii* and *Halobacterium* species NRC-i, *Archaeoglobus fulgidus, Pyrococcus fit riosus, Pyrococcus horikoshii, Pyrobaculum aerophilum, Pyrococcus abyssi, Sulfolobus solfataricus, Sulfolobus tokodaii, Aeuropyrum pernix, Thermoplasma acidophilum*, and *Thermoplasma volcanium*. In one specific, non-limiting embodiment, the recombinant microorganism is an *E. coli* cell, a *S. maltophilia* cell, a *Pseudomonas* sp. cell, a *Bacillus* sp. cell, an *Actinomycetes* cell or cells belonging to the genus *Rhodococcus*. Introduction of the construct into the recombinant microorganism can be accomplished by a variety of methods including, but not limited to, calcium phosphate transfection, DEAE-dextran mediated transfection, polybrene mediated transfection, protoplast fusion, liposome mediated transfection, conjugation, natural transformation, electroporation, and other methods known in the art.

Still other suitable recombinant microorganisms are plant cells, including, but not limited to, species of eukaryotic algae, mosses, club mosses, ferns, angiosperms, gymnosperms, and lichens. Any known method can be employed for plant cell transformation, culture, and regeneration can be employed. Methods for introduction of foreign DNA into plant cells include, but are not limited to, transfer involving the use of *Agrobacterium tumefaciens* and appropriate Ti vectors, including binary vectors; chemically induced transfer (for instance, with polyethylene glycol); biolistics; and microinjection. See, for instance, An et al., *Plant Molecular Biology Manual* A3:1-19, 1988. Various promoters suitable for expression of heterologous genes in plant cells are known in the art, including constitutive promoters, for example the cauliflower mosaic virus (CaMV) 35S promoter, which is expressed in many plant tissues, organ- or tissue-specific promoters, and promoters that are inducible by chemicals such as methyl jasminate, salicylic acid, or safeners.

Recombinant microorganisms are grown under appropriate conditions to a suitable cell density. If the sequence of interest is operably linked to an inducible promoter, the appropriate environmental alteration is made to induce expression. If the product (e.g., hydrocarbon) accumulates in the recombinant microorganism, the cells are harvested, for example, by centrifugation or filtration. Whole cell extractions can be performed to purify the products from the whole cells. If the recombinant microorganisms secrete the product into the medium, the cells and medium are separated, and the medium is retained for purification of the desired product.

B. Genes

1. Structure

As mentioned above, four genes were identified in *Stenotrophomonas maltophilia* that encode proteins involved in the biosynthesis of hydrocarbons, such as olefins and hydrocarbon intermediates, such as aliphatic ketones. These proteins and the nucleic acid sequences that encode them are listed in the accompanying Sequence Listing. One of ordinary skill in the art will appreciate that by using the information provided herein relating to the structure and function of the *S. maltophilia* sequences other sequences having similar activity can be obtained. To demonstrate this, OleA, OleC and OleD sequences showing relatively high sequence identity when compared to the *S. maltophilia* sequence (e.g., sequences from *Xanthomonas axonopodis* see Table 2) and sequences having relatively low sequence identity with *S. maltophilia* (e.g., sequences from *Chloroflexus aggregans* see Table 2) were cloned and the expected activities were measured. Given these teachings, one of ordinary skill in the art will appreciate that additional OleA, OleC, and OleD sequences can readily be cloned and used to make hydrocarbons and hydrocarbon intermediates. Therefore, throughout this description reference to OleA, OleC, or OleD should be understood to mean all proteins displaying the respective activity, including, for example, those in Table 2, as well as others that can be identified or engineered through various molecular techniques such as antibody binding, nucleic acid hybridization, PCR and the like.

In some examples, variants of the proteins provided in SEQ ID NO: 2, 4, 6, 8, 10, 12, 14, 16, 18, 20, or 22 can have no more than about 3, 5, 10, 15, 20, or 25 conservative amino acid changes.

In one example, a conservative variant of an amino acid sequence provided in SEQ ID NO: 2, 4, 6, 8, 10, 12, 14, 16, 18, 20, or 22 is one that functionally performs substantially like the respective amino acid sequence without the amino acid variations (any one of the assays provided herein can be used to assess activity). In some examples, a conservative variant of an OleA (SEQ ID NO: 2, 4, 12, or 18) can be assayed for hydrocarbon synthase activity, such as acyl condensing activity, aliphatic ketone synthase activity and/or olefin synthase activity. In other examples, conservative variants of OleC and OleD can be assayed using the various assays described herein. The conservative variant can have, for instance, one variation, two variations, three variations, four variations, or five or more variations in sequence, as long as activity is maintained.

In some embodiments, a conservative variant of the proteins provided in Table 2 and in the sequence listing include one or more conservative amino acid substitutions compared to the sequence from which it was derived, and yet retains its respective activity. For example, a conservative variant OleA, OleC, or OleD can retain at least about 10% of the biological activity of the parent OleA, OleC, or OleD protein from which it was derived, or alternatively, at least about 20%, at least about 30%, or at least about 40%. In some preferred embodiments, a conservative variant OleA, OleC, or OleD retains at least about 50% of the biological activity of the parent OleA, OleC, or OleD molecule from which it was derived. The conservative amino acid substitutions of a conservative variant OleA, OleC, or OleD can occur in any domain of the OleA, OleC, or OleD protein.

Proteins with even greater similarity to the reference sequence that maintain the activity of OleA, OleC, or OleD are also provided herein. Such proteins will show increasing percentage identities when assessed by this method, such as at least about 35%, at least about 45%, at least about 50%, at least about 60%, at least about 80%, at least about 85%, at least about 90%, at least about 95%, at least about 98%, or at least about 99% sequence identity to SEQ ID NOS: 2, 4, 6, 8, 10, 12, 14, 16, 18, 20, or 22.

In one example, a homolog of an OleA (SEQ ID NO: 2), OleC (SEQ ID NO: 6), or OleD (SEQ ID NO: 8) protein is one that functionally performs substantially like OleA (SEQ ID NO: 2), OleC (SEQ ID NO: 6), or OleD (SEQ ID NO: 8), for instance, in terms of having hydrocarbon synthase activity. In this example, the OleA (SEQ ID NO: 2), OleC (SEQ ID NO: 6), or OleD (SEQ ID NO: 8) homolog and the OleA (SEQ ID NO: 2), OleC (SEQ ID NO: 6), or OleD (SEQ ID NO: 8) protein do not have the same amino acid sequences, however, they have similar hydrocarbon synthase activities.

Although particular embodiments of hydrocarbon and hydrocarbon intermediate forming sequences are disclosed, it will be understood that sequences that have similar structural characteristics can be isolated from other microorganisms. These newly isolated sequences can be assayed for hydrocarbon synthase activity (see Table 2 for a list of specific, non-limiting examples of related sequences). In addition, it will be understood that other functionally equivalent forms of the amino acid sequences disclosed herein can be readily identified and/or generated using conventional molecular biological techniques, including, for instance, site-directed mutagenesis or M13 primer mutagenesis. Details of these techniques are provided in Sambrook et al., *Molecular Cloning: A Laboratory Manual,* 3rd ed., vol. 1-3, Cold Spring Harbor, N.Y., 2000, Ch. 15. Thus, in addition to structurally related sequences and homologous sequences, the disclosure also encompasses amino acid sequences that have at least about 30%, 35%, 40%, 45%, 50%, 55%, 60%, 70%, 75%, 80%, 85%, 90%, or 95% sequence identity with SEQ ID NOS: 2, 4, 6, 8, 10, 12, 14, 16, 18, 20, and 22, or in further embodiments at least about 96%, 97%, 98%, or 99% sequence identity.

Sequences retaining structural and functional similarity to OleA, OleC, and OleD can be identified by any number of known methods. One such method involves the screening of genomic sequences for sequence alignment with the known sequence(s). Methods for aligning sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene* 73:237-244, 1988; Higgins & Sharp, *CABIOS* 5:151-153, 1989; Corpet et al., *Nucleic Acids Research* 16:10881-10890, 1988; Huang, et al., *CABIOS* 8:155-165, 1992; and Pearson et al., *Methods in Molecular Biology* 24:307-331, 1994. Altschul et al., *J. Mol. Biol.* 215:403-410, 1990, presents a detailed description of sequence alignment methods and homology calculations.

In some examples the recombinant microorganism expresses a nucleic acid sequence such as those shown in SEQ ID NOS: 1, 3, 5, 7, 9, 11, 13, 15, 17, 19, 21 or homologs thereof. In other examples the recombinant microorganism can be engineered to express a nucleic acid sequence that hybridizes to or has at least about 35% sequence identity with SEQ ID NO: 1, 3, 5, 7, 9, 11, 13, 15, 17, 19, or 21.

When a genomic sequence is not available for a particular species of interest, related sequences can be amplified from total RNA using RT-PCR. Briefly, total RNA is extracted from the cells of interest by any one of a variety of well known methods. Sambrook et al., *Molecular Cloning: A Laboratory Manual,* 3rd ed., vol. 1-3, Cold Spring Harbor, N.Y., 2000, and Ausubel et al. (in Current Protocols in Molecular Biology, Greene Publ. Assoc. and Wiley-lnterSciences, 1992) provide descriptions of methods for RNA isolation. Generally, any microorganism can be used as a source of such RNA. The extracted RNA is then used as a template for performing reverse transcription-polymerase chain reaction (RT-PCR) amplification of cDNA. Methods and conditions for RT-PCR are described in Kawasaki et al., (in PCR Protocols, A Guide to Methods and Applications, Innis et al. (eds.), 21-27, Academic Press, Inc., San Diego, Calif., 1990).

The selection of amplification primers will be made according to the particular cDNA that is to be amplified. Specific examples of primers of use are shown in Table 3, below. However, these primers are illustrative only; one of ordinary skill in the art will appreciate that many different primers can be derived from the OleA, OleC, and OleD nucleic acid sequences. Variations in amplification conditions can be required to accommodate primers and amplicons of differing lengths and composition; such considerations are well known in the art and are discussed for instance in Innis et al. (PCR Protocols, A Guide to Methods and Applications, Academic Press, Inc., San Diego, Calif., 1990).

Sequencing of PCR products obtained by these amplification procedures can be used to facilitate confirmation of the amplified sequence and provide information about natural variation of this sequence in different species. Oligonucleotides derived from the provided OleA, OleC, and OleD sequences can be used in such sequencing methods. Closely related orthologous OleA, OleC, and OleD, molecules can share at least about 30%, 35%, 40%, 45%, 50%, 55%, 60%, 65%, 70%, 75%, 80%, 85%, 90%, 95%, or at least about 98% sequence identity with the disclosed OleA, OleC, and OleD sequences (see, the sequence listing as well as Table 2).

TABLE 2

Additional examples of OleA, OleB, OleC and OleD compared to *Stenotrophomonas maltophilia*

BlastP against NR from NCBI, as of May 21, 2007

| Gene | Organism | GenBank Acc # | Pct. Identity | Pct. Positive |
|---|---|---|---|---|
| OleA | *Xanthomonas campestris* | NP_635607 | 88% | 94% |
| OleA | **Xanthomonas axonopodis* | NP_640589 | 87% | 94% |
| OleA | *Xanthomonas oryzae* | YP_202848 | 87% | 93% |
| OleA | *Xylella fastidiosa* | NP_299252 | 78% | 89% |
| OleA | **Chloroflexus aggregans* | ZP_01515932 | 45% | 61% |
| OleA | *Chloroflexus aurantiacus* | ZP_00768309 | 44% | 60% |
| OleA | *Brevibacterium linens* | ZP_00380722 | 43% | 66% |
| OleA | *Clavibacter michiganensis* | CAN02225 | 44% | 65% |
| OleA | *Arthrobacter aurescens* | YP_947743 | 44% | 61% |
| OleA | *Kineococcus radiotolerans* | ZP_00618003 | 39% | 63% |
| OleA | *Congregibacter litoralis* | EAQ97163 | 40% | 60% |
| OleA | *Desulfotalea psychrophila* | YP_064477 | 36% | 52% |
| OleA | *Geobacter lovleyi* | ZP_01592199 | 35% | 53% |
| OleA | *Candidatus Desulfococcus oleovorans* | ZP_01674937 | 34% | 54% |
| OleA | *Geobacter bemidjiensis* | ZP_01774807 | 35% | 52% |
| OleA | *Geobacter uraniumreducens* | ZP_01140553 | 36% | 52% |
| OleA | *Geobacter* sp. FRC-32 | ZP_01387895 | 35% | 51% |
| OleA | *Shewanella baltica* OS155 | YP_001049933 | 35% | 51% |
| OleA | *Shewanella loihica* PV-4 | YP_001093839 | 35% | 51% |
| OleA | *Shewanella* sp. W3-18-1 | YP_964031 | 35% | 52% |
| OleA | *Photobacterium profundum* | ZP_01221857 | 35% | 50% |
| OleA | *Shewanella frigidimarina* | YP_750056 | 35% | 51% |
| OleA | *Shewanella oneidensis* | NP_717352 | 34% | 52% |
| OleA | *Rhodopirellula baltica* | NP_870717 | 33% | 52% |
| OleA | *Shewanella denitrificans* | YP_562378 | 35% | 50% |
| OleA | *Shewanella pealeana* | ZP_01603836 | 34% | 51% |
| OleA | *Colwellia psychrerythraea* | YP_268878 | 35% | 50% |
| OleA | *Shewanella woodyi* | ZP_01541536 | 34% | 51% |
| OleA | *Pelobacter propionicus* | YP_902754.1\| | 36% | 52% |
| OleA | *Blastopirellula marina* | ZP_01092573 | 33% | 51% |
| OleA | *Shewanella amazonensis* | YP_927059 | 34% | 50% |
| OleA | *Shewanella* sp. MR-4 | YP_734676 | 34% | 52% |
| OleA | *Shewanella* sp. MR-7 | YP_738657 | 34% | 52% |
| OleA | *Desulfuromonas acetoxidans* | ZP_01311976 | 33% | 49% |
| OleA | *Shewanella* sp. ANA-3 | YP_870348 | 34% | 52% |
| OleA | *Psychromonas* sp. CNPT3 | ZP_01216825 | 33% | 51% |
| OleA | *Psychromonas ingrahamii* | YP_943361 | 35% | 52% |
| OleA | *Streptomyces ambofaciens* | CAJ87980 | 29% | 45% |
| OleA | *Saccharophagus degradans* | YP_526991 | 27% | 47% |
| OleA | *Candidatus Kuenenia stuttgartiensis* | CAJ72134 | 26% | 44% |
| OleA | *Streptomyces ambofaciens* | CAK50926 | 27% | 44% |
| OleA | *Arthrobacter sp. FB24* | YP_832433 | 27% | 45% |
| OleA | *Maricaulis maris* | YP_756753 | 28% | 44% |

TABLE 2-continued

Additional examples of OleA, OleB, OleC and OleD compared to *Stenotrophomonas maltophilia*

BlastP against NR from NCBI, as of May 21, 2007

| Gene | Organism | GenBank Acc # | Pct. Identity | Pct. Positive |
|---|---|---|---|---|
| OleA | *Burkholderia cenocepacia* | YP_620524 | 26% | 45% |
| OleA | *Burkholderia* sp. 383 | YP_368474 | 25% | 45% |
| OleA | *Burkholderia multivorans* | ZP_01570280 | 26% | 45% |
| OleA | *Burkholderia thailandensis* | YP_442252 | 25% | 46% |
| OleA | *Burkholderia vietnamiensis* | YP_001118886 | 26% | 45% |
| OleA | *Rickettsia canadensis* | ZP_01347964 | 25% | 46% |
| OleA | *Burkholderia phytofirmans* | ZP_01512568 | 25% | 45% |
| OleA | *Parvularcula bermudensis* | ZP_01016131 | 29% | 45% |
| OleB | *Xanthomonas campestris* | YP_361972 | 80% | 89% |
| OleB | *Xanthomonas axonopodis* | NP_640591 | 79% | 88% |
| OleB | *Xanthomonas oryzae* | YP_202852 | 78% | 88% |
| OleB | *Xylella fastidiosa* | ZP_00680138 | 72% | 82% |
| OleB | *Shewanella pealeana* | ZP_01603837 | 54% | 74% |
| OleB | *Shewanella woodyi* | ZP_01541535 | 54% | 74% |
| OleB | *Colwellia psychrerythraea* | YP_268879 | 55% | 72% |
| OleB | *Photobacterium profundum* | ZP_01221858 | 53% | 72% |
| OleB | *Shewanella denitrificans* | YP_562379 | 53% | 73% |
| OleB | *Shewanella oneidensis* | NP_717353 | 53% | 72% |
| OleB | *Shewanella* sp. MR-4 | YP_734675 | 53% | 72% |
| OleB | *Shewanella* sp. MR-7 | YP_738656 | 53% | 72% |
| OleB | *Shewanella amazonensis* | YP_927060 | 53% | 70% |
| OleB | *Psychromonas ingrahamii* | YP_943362 | 53% | 71% |
| OleB | *Shewanella loihica* PV-4 | YP_001093840 | 52% | 72% |
| OleB | *Shewanella frigidimarina* | YP_750057 | 53% | 73% |
| OleB | *Shewanella* sp. ANA-3 | YP_870347 | 53% | 72% |
| OleB | *Shewanella baltica* | ZP_01780735 | 52% | 72% |
| OleB | *Shewanella* sp. W3-18-1 | YP_964030 | 52% | 72% |
| OleB | *Psychromonas* sp. CNPT3 | ZP_01216824 | 51% | 70% |
| OleB | *Shewanella putrefaciens* | ZP_01706252 | 51% | 71% |
| OleB | *Geobacter uraniumreducens* | ZP_01140552 | 53% | 70% |
| OleB | *Geobacter lovleyi* | ZP_01592200 | 51% | 68% |
| OleB | *Desulfuromonas acetoxidans* | ZP_01311977 | 52% | 70% |
| OleB | *Pelobacter propionicus* | YP_902755 | 51% | 68% |
| OleB | *Geobacter* sp. FRC-32 | ZP_01387896 | 50% | 68% |
| OleB | *Geobacter bemidjiensis* | ZP_01774808 | 52% | 69% |
| OleB | *Chloroflexus aggregans* | ZP_01515936 | 46% | 63% |
| OleB | *Candidatus Desulfococcus oleovorans* | ZP_01674938 | 42% | 62% |
| OleB | *Chloroflexus aurantiacus* | ZP_00768313 | 45% | 63% |
| OleB | *Blastopirellula marina* | ZP_01089728 | 41% | 61% |
| OleB | *Desulfotalea psychrophila* | YP_066368 | 39% | 60% |
| OleB | *Streptomyces ambofaciens* | CAJ87981 | 39% | 53% |
| OleB | *Rhodopirellula baltica* | NP_869327 | 36% | 53% |
| OleB | *Hahella chejuensis* | YP_436645 | 37% | 53% |
| OleB | *Jannaschia* sp. CCS1 | YP_510567 | 35% | 55% |
| OleB | *Arthrobacter aurescens* | YP_947744 | 39% | 52% |
| OleB | *Congregibacter litoralis* | EAQ97162 | 33% | 47% |
| OleB | marine gamma proteobacterium HTCC2080 | ZP_01626385 | 31% | 47% |
| OleB | *Clavibacter michiganensis* | CAN02224 | 33% | 44% |
| OleB | *Burkholderia cenocepacia* | YP_624045 | 32% | 45% |
| OleB | *Ralstonia pickettii* | ZP_01663163 | 31% | 43% |
| OleB | *Burkholderia* sp. 383 | YP_372607 | 31% | 45% |
| OleB | *Pseudoalteromonas atlantica* | YP_661487 | 30% | 46% |
| OleB | *Mycobacterium avium* | YP_881340 | 35% | 50% |
| OleB | *Mycobacterium vanbaalenii* | YP_953204 | 31% | 47% |
| OleB | *Rhodococcus rhodochrous* | AAC15838 | 31% | 45% |
| OleB | *Mycobacterium* sp. GP1 | CAB65289 | 30% | 45% |
| OleB | *Microscilla marina* | ZP_01689538 | 30% | 46% |
| OleB | *Anaeromyxobacter* sp. Fw109-5 | ZP_01671845 | 33% | 48% |
| OleC | *Xanthomonas oryzae* | YP_453013 | 76% | 82% |
| OleC | *Xanthomonas campestris* | AAM39537 | 77% | 83% |
| OleC | **Xanthomonas axonopodis* | NP_640593 | 77% | 82% |
| OleC | *Xylella fastidiosa* | AAO29160 | 71% | 80% |
| OleC | *Geobacter* sp. FRC-32 | ZP_01387897 | 50% | 64% |
| OleC | *Geobacter uraniumreducens* | ZP_01140551 | 52% | 64% |
| OleC | *Geobacter bemidjiensis* | ZP_01774809 | 51% | 64% |
| OleC | *Geobacter lovleyi* | ZP_01592201 | 50% | 63% |
| OleC | *Pelobacter propionicus* | YP_902768 | 50% | 62% |
| OleC | *Desulfuromonas acetoxidans* | ZP_01311978 | 48% | 62% |
| OleC | *Shewanella loihica* | YP_001093841 | 45% | 60% |
| OleC | *Candidatus Desulfococcus* | ZP_01674939 | 46% | 61% |

TABLE 2-continued

Additional examples of OleA, OleB, OleC and OleD compared to *Stenotrophomonas maltophilia*

BlastP against NR from NCBI, as of May 21, 2007

| Gene | Organism | GenBank Acc # | Pct. Identity | Pct. Positive |
|---|---|---|---|---|
| | *oleovorans* | | | |
| OleC | *Shewanella amazonensis* | YP_927061 | 45% | 60% |
| OleC | *Photobacterium profundum* | ZP_01221859 | 43% | 58% |
| OleC | *Shewanella frigidimarina* | YP_750058 | 45% | 58% |
| OleC | *Shewanella woodyi* | ZP_01541534 | 44% | 60% |
| OleC | *Shewanella denitrificans* | YP_562380 | 43% | 58% |
| OleC | *Blastopirellula marina* | ZP_01092564 | 45% | 60% |
| OleC | *Psychromonas ingrahamii* | YP_943363 | 42% | 57% |
| OleC | *Shewanella putrefaciens* | YP_001182971 | 41% | 56% |
| OleC | *Shewanella* sp. W3-18-1 | YP_964029 | 41% | 56% |
| OleC | *Shewanella oneidensis* | NP_717354 | 41% | 56% |
| OleC | *Shewanella baltica* | YP_001049935 | 42% | 56% |
| OleC | *Shewanella pealeana* | ZP_01603838 | 41% | 57% |
| OleC | *Shewanella* sp. MR-7 | YP_738655 | 42% | 55% |
| OleC | *Chloroflexus aggregans* | ZP_01515934 | 47% | 60% |
| OleC | *Shewanella* sp. ANA-3 | YP_870346 | 41% | 56% |
| OleC | *Chloroflexus aurantiacus* | ZP_00768311 | 48% | 61% |
| OleC | *Colwellia psychrerythraea* | YP_268880 | 40% | 53% |
| OleC | *Shewanella* sp. MR-4 | YP_734674 | 41% | 54% |
| OleC | *Rhodopirellula baltica* | NP_867442 | 42% | 56% |
| OleC | *Psychromonas* sp. CNPT3 | ZP_01216823 | 39% | 56% |
| OleC | *Desulfotalea psychrophila* | YP_066367 | 43% | 57% |
| OleC | *Nocardia farcinica* | YP_119669 | 44% | 56% |
| OleC | *Mycobacterium vanbaalenii* | YP_951924 | 34% | 48% |
| OleC | *Streptomyces ambofaciens* | CAJ87982 | 36% | 49% |
| OleC | *Congregibacter litoralis* | ZP_01103250 | 34% | 49% |
| OleC | *Arthrobacter aurescens* | YP_947744 | 35% | 47% |
| OleC | *Brevibacterium linens* | ZP_00380721 | 34% | 48% |
| OleC | *Clavibacter michiganensis* | CAN02224 | 34% | 47% |
| OleC | *Kineococcus radiotolerans* | ZP_00618000 | 34% | 46% |
| OleC | *Photorhabdus luminescens* | NP_931676 | 30% | 44% |
| OleC | *Bdellovibrio bacteriovorus* | NP_969916 | 27% | 42% |
| OleC | *Roseovarius nubinhibens* | ZP_00958765 | 29% | 42% |
| OleC | *Microscilla marina* | ZP_01689877 | 26% | 40% |
| OleC | *Vibrio alginolyticus* | ZP_01262572 | 24% | 41% |
| OleC | *Vibrio* sp. Ex25 | ZP_01473723 | 25% | 41% |
| OleC | *Saccharopolyspora erythraea* | YP_001107556 | 28% | 40% |
| OleC | *Frankia alni* | YP_713609 | 28% | 42% |
| OleC | *Ralstonia metallidurans* | YP_586588 | 26% | 41% |
| OleD | *Xanthomonas campestris* | NP_635614 | 81% | 89% |
| OleD | **Xanthomonas axonopodis* | NP_640594 | 79% | 88% |
| OleD | *Xanthomonas oryzae* | YP_202855 | 78% | 89% |
| OleD | *Xylella fastidiosa* | ZP_00651654 | 72% | 81% |
| OleD | *Geobacter* sp. FRC-32 | ZP_01387898 | 54% | 71% |
| OleD | *Geobacter uraniumreducens* | ZP_01140550 | 59% | 73% |
| OleD | *Geobacter bemidjiensis* | ZP_01774810 | 56% | 70% |
| OleD | *Geobacter lovleyi* | ZP_01592203 | 56% | 72% |
| OleD | *Desulfuromonas acetoxidans* | ZP_01311979 | 50% | 70% |
| OleD | *Pelobacter propionicus* | YP_902769 | 56% | 69% |
| OleD | *Psychromonas ingrahamii* | YP_943364 | 49% | 65% |
| OleD | *Psychromonas* sp. CNPT3 | ZP_01216822 | 48% | 67% |
| OleD | *Photobacterium profundum* | ZP_01221860 | 49% | 66% |
| OleD | *Shewanella frigidimarina* | YP_750059 | 50% | 65% |
| OleD | *Shewanella denitrificans* | YP_562381 | 48% | 64% |
| OleD | *Shewanella* sp. MR-7 | YP_738654 | 49% | 63% |
| OleD | *Shewanella pealeana* | ZP_01603839 | 48% | 62% |
| OleD | *Shewanella* sp. MR-4 | YP_734673 | 49% | 63% |
| OleD | *Blastopirellula marina* | ZP_01092566 | 50% | 67% |
| OleD | *Shewanella* sp. ANA-3 | YP_870345 | 50% | 63% |
| OleD | *Colwellia psychrerythraea* | YP_268881 | 45% | 59% |
| OleD | *Shewanella putrefaciens* | ZP_01706254 | 47% | 61% |
| OleD | *Shewanella loihica* | YP_001093842 | 48% | 62% |
| OleD | *Shewanella woodyi* | ZP_01541533 | 47% | 63% |
| OleD | *Shewanella oneidensis* | NP_717355 | 49% | 63% |
| OleD | *Shewanella* sp. W3-18-1 | YP_964028 | 47% | 60% |
| OleD | *Candidatus Desulfococcus oleovorans* | ZP_01674940 | 48% | 63% |
| OleD | *Desulfotalea psychrophila* | YP_066366 | 46% | 64% |
| OleD | *Shewanella baltica* | ZP_01780733 | 44% | 56% |
| OleD | *Shewanella amazonensis* | YP_927062 | 48% | 62% |
| OleD | *Rhodopirellula baltica* | NP_864182 | 42% | 60% |
| OleD | *Chloroflexus arauntiacus* | ZP_00768310 | 45% | 58% |

TABLE 2-continued

Additional examples of OleA, OleB, OleC and OleD compared to *Stenotrophomonas maltophilia*

BlastP against NR from NCBI, as of May 21, 2007

| Gene | Organism | GenBank Acc # | Pct. Identity | Pct. Positive |
|---|---|---|---|---|
| OleD | *Chloroflexus aggregans* | ZP_01515933 | 45% | 57% |
| OleD | *Streptomyces ambofaciens* | CAJ87983 | 45% | 55% |
| OleD | *Candidatus Desulfococcus* | ZP_01672329 | 40% | 55% |
| OleD | *Pseudomonas fluorescens* | YP_261903 | 38% | 54% |
| OleD | *Clavibacter michiganensis* | CAN02223 | 41% | 53% |
| OleD | *Congregibacter litoralis* | EAQ97161 | 40% | 53% |
| OleD | *Herpetosiphon aurantiacus* | ZP_OleB7661 | 37% | 53% |
| OleD | *Pseudomonas entomophila* | YP_606835 | 37% | 51% |
| OleD | *Brevibacterium linens* | ZP_00380720 | 38% | 51% |
| OleD | *Bacillus anthracis* | NP_845549 | 32% | 52% |
| OleD | *Bacillus cereus* | YP_084525 | 32% | 52% |
| OleD | *Bacillus thuringiensis* | YP_895662 | 32% | 52% |
| OleD | *Pseudomonas mendocina* | YP_001186616 | 36% | 50% |
| OleD | *Arthrobacter aurescens* | YP_947745 | 38% | 50% |
| OleD | *Kineococcus radiotolerans* | ZP_00618004 | 40% | 52% |
| OleD | *Mus musculus* | NP_035071 | 33% | 51% |
| OleD | *Mycobacterium leprae* | NP_302310 | 33% | 52% |
| OleD | *Xenopus laevis* | AAH88699 | 33% | 52% |

*indicates genes for which activity data is provided herein

Pct Identity=Percent Identity and Pct Positive=Percent Positive. Percent identity and percent positive are determined as compared to SEQ ID NOS: 4, 6, 8, and 10 as calculated by BLAST™ software set to default parameters. For instance, blastn (version 2.0) software can be used to determine sequence identity between two nucleic acid sequences using default parameters (expect=10, matrix=BLOSUM62, filter=DUST (Tatusov and Lipmann, in preparation as of Dec. 1, 1999; and Hancock and Armstrong, *Comput. Appl. Biosci.* 10:67-70, 1994), gap existence cost=11, per residue gap cost=1, and lambda ratio=0.85). For comparison of two polypeptides, blastp (version 2.0) software can be used with default parameters (expect 10, filter=SEG (Wootton and Federhen, *Computers in Chemistry* 17:149-163, 1993), matrix=BLOSUM62, gap existence cost=11, per residue gap cost=1, lambda=0.85).

2. Function

Hydrocarbon synthase activity is the activity of one or more peptides that causes the conversion of a substrate containing a fatty acyl chain, such as acyl CoA, acyl ACP, or fatty acid, to a hydrocarbon. Examples of peptides having hydrocarbon synthase activity include OleA, OleC, and OleD. Hydrocarbon synthase activity can be tested, for example, using a complementation assay (see Example 4, below). Briefly, organisms that are known to make hydrocarbons upon the expression of OleA, OleC, and OleD (i.e., test hosts) are engineered to express, for example, an OleA and an OleD sequence that are known to produce hydrocarbons in the presence of an OleC such as the one shown in SEQ ID NO: 6. A candidate OleC is then substituted for the OleC that is known to produce hydrocarbons in the test host. The candidate OleC is deemed to have hydrocarbon synthase activity if the test host produces hydrocarbons.

Using the OleA, OleC, and OleD sequences provided herein and the complementation assay described in Example 4, additional hydrocarbon and hydrocarbon intermediate-forming genes can be identified. Hydrocarbons and intermediates thereof can be formed by expressing OleA, OleC, and OleD in *E. coli*. Therefore, *E. coli*, or other organisms that naturally or are engineered to make hydrocarbons, such as *S. maltophilia, C. aggregans* or *X. axonopodis*, can be used to determine the hydrocarbon synthase activity of a specific DNA sequence or protein when that specific DNA sequence to be tested is knocked out of the host cell. As an example, when the DNA sequence to be tested is a homolog of an OleA sequence, it is expressed in a host that is already expressing the OleC and OleD sequences, but not the OleA sequences. The homolog of OleA is deemed to be active (i.e., has hydrocarbon synthase activity) if the host produces hydrocarbons or hydrocarbon intermediates when expressing the homolog of OleA.

Recombinant microorganisms can be engineered using the peptides disclosed herein to produce hydrocarbons and aliphatic ketones that have defined structural characteristics (e.g., degrees of branching, saturation, and length). One method of making hydrocarbons involves increasing the expression of, or expressing more active forms of, one or more acyl-condensing enzymes (enzymes that condense more than one acyl-CoA, acyl-ACP, acyl-AMP, acyl-ester, fatty acid or mixtures thereof). One of ordinary skill in the art will appreciate that the products produced from such condensation reactions vary with the acyl chain that is condensed. Products that can be produced include, for example, hydrocarbons and hydrocarbon intermediates, such as aliphatic ketones.

Acyl-condensing peptides include peptides capable of catalyzing the condensation of acyl-ACP, acyl-CoA, acyl-AMP, fatty acids and mixtures thereof using the methods described herein. In some examples, the acyl-condensing peptides are more substrate specific and will only accept, for example, acyl-CoA, acyl-ACP, acyl-AMP, acyl-ester, fatty acid or mixtures thereof. Additionally, one of ordinary skill in the art will appreciate that some acyl-condensing peptides will catalyze other reactions as well, for example some acyl-condensing peptides will accept other substrates in addition to acyl-CoA, acyl-ACP, acyl-AMP, acyl-ester, fatty acid or mixtures thereof. Such non-specific acyl-condensing peptides are, therefore, also included. Examples of acyl-condensing enzymes, in addition to the OleA sequence provided in the sequence listing, are publicly available and provided in Table 2. Exemplary GenBank Accession Numbers are also provided in Table 2.

Generally, there are several methods of identifying peptides having acyl-condensing activity. Product formation using one or more of these methods indicates that the peptide has acyl-condensing activity. In addition to the in vitro assays provided in Example 3, the peptide can be expressed from an exogenous nucleic acid sequence in a cell and then a cell lysate can be prepared. Various substrates such as acyl-CoA, acyl-ACP, acyl-AMP, acyl-ester, fatty acid or mixtures thereof can be added to the lysate and products can be detected using the GC/MS methods described herein. In another example, the peptide can be purified and incubated with cell lysate from a cell that is not expressing the peptide (hereinafter, wild-type lysate). The purified peptide, wild-type lysate and various substrates can be incubated, and the resulting products can be characterized using the GC/MS methods described herein. In yet another example, acyl-condensing activity can be characterized by incubating purified enzyme and substrate in the presence of cell lysate that has been heated to denature proteins. In another example, purified peptide and various substrates can be incubated, and the resulting product can be characterized using the GC/MS methods described herein (see, Example 3). Peptides having acyl-condensing activity are identified as those that produce aliphatic ketones. One of ordinary skill in the art will appreciate that when a cell lysate is used that already contains aliphatic ketones, peptides having acyl-condensing activity will be recognized by an increase in aliphatic ketones compared to the lysate without the addition of substrate (such as an increase of at least about 10%, at least about 20%, at least about 50%, or at least about 90%). In some cases, the condensation can result in the production of molecules derived from one or more of the substrates. For example, the condensation of two acyl-CoA molecules may produce at least one molecule of CoA. As CoA has a free thiol moiety (RSH), which is highly reactive, this molecule can be detected by a variety of methods. One such method is reaction with dithionitrobenzoic acid (Ellman's reagent) which can be followed spectrophotometrically at 411 nm. Alternatively, CoA can be reacted with monobromobimane and detected by HPLC (Fahey, R. C., and Newton, G. L. *Methods Enzymol.* 143, 85-96, 1987).

Bioinformatic methods can be used to find acyl-condensing peptides. Acyl-condensations occur through a well known chemical reaction known as the "Claisen condensation". The Claisen condensation is a carbon-carbon bond forming reaction that occurs between two esters or one ester and another carbonyl compound in the presence of a strong base resulting in a β-keto ester or a β-diketone.

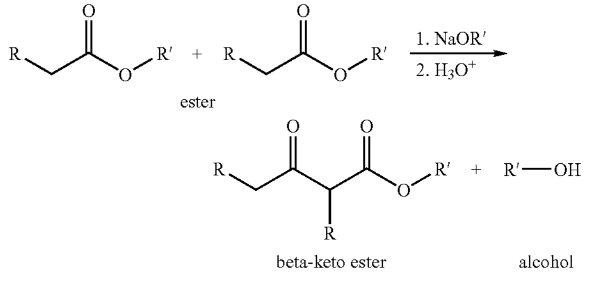

Acyl-condensation peptides typically contain a catalytic triad composed of Cys-His-Asn. The condensing enzymes share a common 3-dimensional fold, although they share little similarity at the amino acid level. Their active sites, however, possess significant similarities. (Heath, R. J. and Rock, C. O. *Nat. Prod. Rep.,* 19:581-596, 2002).

Exemplary acyl-condensing peptides include the OleA sequences provided in the sequence listing, the sequences shown in Table 2, homologs of these sequences, enzymes having one or more of the structural motifs provided in Table 6 and active fragments/variants thereof that display acyl-condensing activity.

Recombinant microorganisms can be engineered using the peptides disclosed herein to produce hydrocarbons and hydrocarbon intermediates having defined structural characteristics (degrees of branching, saturation, and length). One method of making hydrocarbon intermediates involves expressing, increasing the expression of, or expressing more active forms of, one or more enzymes having hydrocarbon synthase activity, adenylating peptides, dehydrogenases, dehydratases, or acyl-condensing enzymes. Exemplary enzymes that can be manipulated to increase hydrocarbon production include OleA, OleB, OleC, and OleD, as well as other enzymes that increase or modify fatty acid production. One of ordinary skill in the art will appreciate that the products produced from such enzymes vary with the acyl chain of the substrate.

Adenylating peptides include peptides capable of catalyzing the addition of adenosine monophosphate to hydrocarbon intermediates, such as a β-ketoacid, including α-substituted-β-ketoacids, particularly those including an aliphatic hydrocarbon at the a position. As described above, the α-aliphatic group in such intermediates typically is an optionally branched hydrocarbon chain optionally including one or more sites of unsaturation, for example, one, two or three alkene moieties in the hydrocarbon chain. Such adenylating peptides also may be capable of catalyzing the addition of adenosine monophosphate to β-hydroxy ketoacids to form a β-ketoester. Methods of identifying such activity are provided herein. In some examples, the adenylating peptides are more substrate specific and will only accept, for example, CoA, or ACP activated β-ketoesters. Additionally, one of ordinary skill in the art will appreciate that some adenylating peptides will catalyze other reactions as well. For example, some adenylating peptides will accept other substrates in addition to α-substituted β-ketoacids. Such relatively non-specific adenylating peptides are, therefore, also included. Examples of adenylating peptides are publicly available and provided in Table 2. Exemplary GenBank Accession Numbers are provided in Table 2. Often the adenylating peptide catalyzes additional further reactions, such as the transesterification of the adenylated compound with other activating groups, such as CoA. This activity is considered ligase activity or synthetase activity. An example would be the following set of reactions:

$$R+ATP \rightarrow R—OPO_3\text{-Adenosine}+\text{pyrophosphate} \quad 1)$$

$$R—OPO_3\text{-Adenosine}+CoASH \rightarrow R—SCoA+AMP \quad 2)$$

There are several methods of identifying peptides having adenylating activity. Product formation using one or more of these methods indicates that the peptide has adenylating activity. In addition to the in vivo assays provided in Example 4, the peptide can be expressed from an exogenous nucleic acid sequence in a cell, and then a cell lysate can be prepared. Various substrates such as ATP can be added to the lysate and products can be detected using the methods described herein (see, Example 6). In another example, the peptide can be purified and incubated with cell lysate from a cell that is not expressing the peptide. The purified peptide, wild-type lysate and various substrates can be incubated and the resulting products can be characterized using the methods described herein (see, Example 1). One of ordinary skill in the art will appreciate that when a cell lysate is used that already contains adenylated products, peptides having adenylating activity will be recognized by an increase in either free PPi, AMP α-substituted-β-ketoesters or AMP α-substituted-β-hydroxyesters compared to the lysate without the addition of substrate.

Exemplary adenylating peptides include OleC (SEQ ID NO: 6), the related enzymes shown in Table 2, and active fragments/variants thereof which display adenylating activity.

Dehydrogenase peptides include peptides capable of catalyzing the reduction of a keto group in an aliphatic-ketone, an aliphatic β-ketoacid, or an aliphatic β-ketoester molecule to the corresponding hydroxy group (the addition of $H_2$ across the carbon-oxygen double bond). Methods of identifying such activity are provided herein. In some examples, the dehydrogenase peptides are more substrate specific and will only accept, for example, CoA or ACP esters of α-aliphatic-β-ketoesters. Additionally, one of ordinary skill in the art will appreciate that some dehydrogenase peptides will catalyze other reactions as well, for example some dehydrogenase peptides will accept other substrates in addition to β-ketoesters. Such non-specific dehydrogenase peptides are, therefore, also included. Examples of dehydrogenase peptides are OleD (SEQ ID NO: 8) and the publicly available dehydrogenases peptides provided in Table 2. Exemplary GenBank Accession Numbers are also provided in Table 2.

There are several methods of identifying peptides having dehydrogenase activity. Product formation using one or more of these methods indicates that the peptide has dehydrogenase activity. In addition to the in vivo assay provided in Example 4, the peptide can be expressed from an exogenous nucleic acid sequence in a cell and then a cell lysate can be prepared. Various substrates such as NADPH and/or NADH can be added to the lysate and products can be detected using the GC/MS methods described herein (see Example 7). In another example, the peptide can be purified and incubated with cell lysate from a cell that is not expressing the peptide. The purified peptide, wild-type lysate and various substrates can be incubated and the resulting products can be characterized using the methods described herein (see Example 1). In yet another example, dehydrogenase activity can be detected by spectrophotometrically monitoring the dehydrogenase dependent oxidation of the NADPH or NADH in the presence of the ketone substrate. The dehydrogenase activity is detected as a decrease in absorbance of the reaction solution at 340 nm. In yet another example, dehydrogenase activity can be characterized by incubating purified enzyme and substrate (e.g., NAD(P)H and α-aliphatic-β-ketoesters and/or α-aliphatic-β-ketoacids) in the presence of cell lysate that has been heated to denature proteins (see, Example 7). Peptides having dehydrogenase activity are identified as those that produce β-hydroxy acid or ester (particularly activated ester) molecules from one or more of the above described reactions. One of ordinary skill in the art will appreciate that when a cell lysate is used that already contains β-hydroxy acid and/or ester products, peptides having dehydrogenase activity will be recognized by an increase in either NADP or β-hydroxy acid and/or ester molecules compared to the lysate without the addition of substrate.

Exemplary dehydrogenase peptides include OleD (SEQ ID NO: 8) and the related enzymes shown in Table 2. Additional OleD enzymes can be identified by searching various databases using the motifs provided in Table 7 and the methodology described in Example 6.

Also disclosed herein are nucleic acid sequences encoding a peptide having hydrolase activity, in particular the peptide would have β-keto or β-hydroxy ester hydrolytic activity. Such a peptide likely would catalyze the hydrolysis of esters of all of the substrates described above producing the corresponding carboxylic acid. Ester hydrolases can be detected by monitoring the production of product, such as the β-ketoacid or β-hydroxyacid by HPLC (or other well-known technique), or, for example, by monitoring the resulting decrease in pH resulting from the formation of the free acid. Alternatively, ester hydrolysis can be monitored by the measuring the accumulation of the moiety released from the fatty ester, such as CoASH, AMP, or phosphate. To those skilled in the art, methods for monitoring these compounds are well known and some of these methods are described above. Phosphate can be monitored, for example, by reaction with molybdate and malachite green. Additional assays can be obtained commercially, for example, from BioVision, Inc., Mountain View, Calif. 94043.

C. Recombinant Nucleic Acid Constructs

Also disclosed herein are recombinant nucleic acid constructs that include one or more nucleic acid sequences encoding OleA, OleC, OleD; homologs of SEQ ID NO: 2, 4, 6, 8, 10, 12, 14, 16, 18, 20, or 22; conservative variants of SEQ ID NO: 2, 4, 6, 8, 10, 12, 14, 16, 18, 20, or 22; and/or sequences having at least about 35% sequence identity with SEQ ID NO: 2, 4, 6, 8, 10, 12, 14, 16, 18, 20, or 22. Exemplary recombinant nucleic acid constructs of use include cloning vectors, expression vectors or synthetic operons.

Both cloning and expression vectors contain nucleotide sequences that allow the vectors to replicate in one or more suitable recombinant microorganisms. In cloning vectors, this sequence is generally one that enables the vector to replicate independently of the recombinant microorganism chromosomes and also includes either origins of replication or autonomously replicating sequences. Various bacterial and viral origins of replication are well known and include, but are not limited to, the pBR322 plasmid origin and the SV40, polyoma, adenovirus, VSV and BPV viral origins.

The nucleic acid sequences disclosed herein can be used to produce proteins by the use of recombinant expression vectors containing the nucleic acid sequence(s). A wide variety of expression vectors can be used. For example, chromosomal, episomal and virus-derived vectors, including vectors derived from bacterial plasmids, bacteriophages, yeast episomes, yeast chromosomal elements, viruses, such as baculoviruses, papoviruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express polynucleotides to express a polypeptide in a recombinant microorganism can be used for expression in this regard. Therefore, any other vector that is replicable and viable in the recombinant microorganism can be used.

The appropriate DNA sequence is inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4-DNA ligase. Procedures for restriction and ligation are well known. Suitable procedures in this regard and for constructing expression vectors using alternative techniques, which also are well known, are set forth in great detail in Sambrook et al. (2000); Ausubel et al. (1995).

Linking is achieved by conventional techniques such as SOE PCR, DNA synthesis, blunt end ligation, or ligation at restriction enzyme sites. If suitable restriction sites are not available, then synthetic oligonucleotide adapters or linkers can be used (Sambrook et al., 2000; Ausubel et al., 1995).

It will be recognized that numerous promoters are functional in bacterial cells and have been described in the literature, including constitutive, inducible, developmentally regulated, and environmentally regulated promoters. Of particular interest is the use of promoters (also referred to as transcriptional initiation regions) that are functional in the appropriate microbial recombinant microorganism. For example, if *E. coli* is used as a recombinant microorganism, then exemplary promoters that can be used include, but are not limited to, the phage lambda PL promoter, the *E. coli* lac, trp and tac promoters, the SV40 early and late promoters, promoters of retroviral LTRs, the CaMV 35S promoter, coconut foliar decay virus (CFDV) DNA (U.S. Pat. No. 6,303,345), and the endogenous promoters of *P. citrorellolis*. If *Saccharomyces cerevisiae* is the host, then the sequences of interest are typically under the control of yeast promoters. A specific, non-limiting example of a useful yeast promoter includes the GAL/CYC promoter. It will be understood that numerous promoters known to a person of ordinary skill in the art which are not mentioned herein are suitable for use and can be readily employed in the manner illustrated herein. Other promoters known to control the expression of genes in prokaryotic or eukaryotic cells can be used. Expression vectors can also contain a ribosome binding site for translation initiation and a transcription terminator. The vector can also contain sequences useful for the amplification of gene expression.

Regulatory transcript termination regions can be provided in expression constructs, as well. Transcript termination regions can be provided by the vector sequence that encodes the OleA (SEQ ID NOS: 2, 4, 12, 18), OleC (SEQ ID NOS: 6, 14, 20), and/or OleD (SEQ ID NOS: 8, 16, 22) sequences or a transcript termination region which is naturally associated with the transcript initiation region can be used. Any convenient transcript termination region that is capable of terminating transcription in a recombinant microorganism can be employed in the constructs disclosed herein.

Expression and cloning vectors can, and usually do, contain a structural gene or selection marker having the necessary regulatory regions for expression in a recombinant microorganism to provide for selection of transformant cells. The gene can provide for resistance to a cytotoxic agent, for instance an antibiotic, heavy metal, toxin, complementation providing prototrophy to an auxotrophic host, viral immunity or the like. Depending upon the number of different host species into which the expression construct or components thereof are introduced, one or more markers can be employed where different conditions for selection are used for the different hosts.

Specific, non-limiting examples of suitable selection markers include genes that confer resistance to bleomycin, gentamycin, glyphosate, hygromycin, kanamycin, methotrexate, nalidixic acid, phleomycin, phosphinotricin, spectinomycin, streptomycin, sulfonamide, sulfonylureas, ampicillin/carbenicillin, chloramphenicol, or streptomycin/spectinomycin, and tetracycline. Specific, non-limiting examples of markers include, but are not limited to, alkaline phosphatase (AP), myc, hemagglutinin (HA), 13 glucuronidase (GUS), luciferase, and green fluorescent protein (GFP).

In addition, expression vectors also can contain marker sequences operatively linked to a nucleotide sequence for a protein that encodes an additional protein used as a marker. The result is a hybrid or fusion protein comprising two linked and different proteins. The marker protein can provide, for example, an immunological or enzymatic marker for the recombinant protein produced by the expression vector. Additionally, the end of the polynucleotide can be modified by the addition of a sequence encoding an amino acid sequence useful for purification of the protein produced. For example, a DNA sequence encoding an amino acid sequence conferring affinity to a particular method of chromatography can be included. Various methods have been devised for the addition of such affinity purification moieties to proteins. Representative examples can be found in U.S. Pat. Nos. 4,703,004, 4,782,137, 4,845,341, 5,935,824, and 5,594,115. Any method known in the art for the addition of nucleotide sequences encoding purification moieties can be used. For example, such methods are disclosed in Innis et al. (1990) and Sambrook et al. (2000).

More particularly, the present disclosure includes recombinant constructs that include one or more isolated nucleic acid sequences that encode OleA (e.g., SEQ ID NOS: 2, 4, 12, 18), OleC (e.g., SEQ ID NOS: 6, 14, 20), OleD (e.g., SEQ ID NOS: 8, 16, 22) or variants and homologs of these sequences. The constructs can include a vector, such as a plasmid or viral vector, into which the sequence has been inserted, either in the forward or reverse orientation. The recombinant construct can further include a regulatory sequence, including, for example, a promoter operatively linked to the sequence. Large numbers of suitable vectors and promoters are known and are commercially available. In one embodiment, the pET-21b(+), pCOLADuet-1, pCDFDuet-1, pcDNA3.1(+), and/or pCMV SPORT6.1 (Invitrogen) vectors are used. It will be understood, however, that other plasmids or vectors can be used as long as they are replicable and viable in the host. It will also be understood that recombinant DNA technology resulting in the integration of the respective DNA sequences encoding for OleA (e.g., SEQ ID NOS: 2, 4, 12, 18), OleC (e.g., SEQ ID NOS: 6, 14, 20), OleD (e.g., SEQ ID NOS: 8, 16, 22) and/or variants and homologs of these sequences into the chromosome of any living organism can result in expression and production of the respective proteins.

The polynucleotide sequence also can be part of an expression cassette that at a minimum includes a promoter, one or more nucleic acids of the present disclosure, and a transcriptional termination signal sequence functional in a recombinant microorganism. The promoter can be any of the types discussed herein. For example, an inducible promoter or constitutive promoter and the expression cassette can further include an operably linked targeting sequence or transit or secretion peptide coding region capable of directing transport of the protein produced. The expression cassette can also further include a nucleotide sequence encoding a selectable marker and/or a purification moiety.

Regulatory sequences, coding sequences, and combinations thereof, can be introduced or altered in the chromosome of the host strain. In some examples, the integration of the desired recombinant sequence into the recombinant microorganism genomic sequence does not require the use of a selectable marker such as an antibiotic. In some examples, the genomic alterations include changing the control sequence of the target genes, such as OleA, OleC, or OleD by replacing the native promoter(s) with a promoter insensitive to regulation. There are numerous approaches to do this, for example, Valle and Flores, *Methods Mol. Biol.* 267:113-122, 2006 describes a PCR-based method to over express chromosomal genes in *E. coli*. Another approach is based on the use of single-strand oligonucleotides to create specific mutations directly in the chromosome using the technology developed by Court et al., *Proc. Nat. Acad. Sci.* 100: 15748-15753, 2003. This technology is based on the use of the over expression of the beta protein from the bacteriophage lambda to enhance genetic recombination. The advantages of this approach are that synthetic oligonucleotides 70 bases long (or more) can be used to create point mutations, insertions and deletions. This method eliminates cloning steps. Furthermore, the system is so efficient that no markers are necessary to isolate the desired mutations. This approach is useful for over expressing, among other things, endogenous coding sequences such as those that encode OleA, OleC, OleD, or the fatty acid biosynthetic pathway enzymes described in FIG. 7.

D. Product Production

The disclosure provides methods of making biocrude, hydrocarbon feedstocks, aliphatic ketones, hydrocarbons, and intermediates thereof. Various recombinant microorganisms are provided that can be used to produce products having engineered carbon chain lengths, saturation sites, and branch points. Methods of making such products are also provided as well as methods of further modifying the products, such as through cracking, to create high quality biofuels and specialty chemicals.

1. Carbon Chain Characteristics

The biocrude, hydrocarbon feedstocks, aliphatic ketones, hydrocarbons, and intermediates can be engineered to have specific carbon chain characteristics by expressing various enzymes or attenuating the expression of various enzymes in the recombinant microorganism. For example, carbon chain length can be controlled by expressing various thioesterases in the recombinant microorganism while attenuating the expression of endogenous thioesterases. Similarly, various branch points can be introduced into the carbon chain by expressing various bkd genes, and the degree of saturation can also be controlled by expressing various genes, for example, by over expressing fabB. A detailed description of the various modifications which can be included in a recombinant microorganism to provide specific carbon chain characteristics and to increase fatty acid biosynthetic pathway production is provided in the published patent application, PCT/US2007/011923, which is herein incorporated in its entirety by reference.

2. Methods of Making Products and Intermediates

One of ordinary skill in the art will appreciate that substrates containing fatty acyl chain and intermediates thereof can be produced using in vitro reactions, including chemical or enzymatic conversions, as well as through in vivo reactions. Additionally, a combination of in vivo and in vitro conversions can be utilized. Moreover, specific aliphatic ketones or hydrocarbons can be produced by selectively providing selected substrates, such as fatty acids, acyl-ACP, acyl-CoA, or aliphatic ketones for the conversion.

The terms "convert" or "conversion" refer to the use of either chemical means or polypeptides in a reaction which changes a first intermediate to a second intermediate. The term "chemical conversion" refers to reactions that are not actively facilitated by polypeptides. The term "biological conversion" refers to reactions that are actively facilitated by polypeptides. Conversions can take place in vivo, in vitro, or both. When biological conversions are used, the peptides and/or cells can be immobilized on supports, such as by chemical attachment onto polymer supports. The conversions can be accomplished using any reactor known to one of ordinary skill in the art, for example in a batch or a continuous reactor.

The recombinant microorganism can convert several intermediates to subsequent intermediates or the recombinant microorganism can be fed, or placed in contact with, an intermediate that is converted to a product. In certain examples, the recombinant microorganism is placed in contact with an intermediate, such as an acyl CoA molecule and that acyl CoA molecule is converted into a product.

a. In Vitro

Given the disclosure provided herein, large scale enzyme production of the peptides OleA (e.g., SEQ ID NOS: 2, 4, 12, 18), OleC (e.g., SEQ ID NOS: 6, 14, 20), OleD (e.g., SEQ ID NOS: 8, 16, 22), and homologs thereof is now possible. Briefly, the coding sequences from any one of these peptides or homologs of these peptides (see, Table 2) can be cloned into a high expression plasmid, such as pET-21B(+) or pCOLADuet-1 (EMD Chemicals, Inc., Germany), and the plasmid can be induced into a host cell. The resulting peptides can then be purified and used in batch production.

When in vitro methods are used, the peptides supplied to the reaction will depend upon the starting material. For example, when a hydrocarbon is desired and the starting material is acyl-ACP, a thioesterase and appropriate co-reactants can be added in conjunction with peptides OleA (e.g., SEQ ID NOS: 2, 4, 12, 18), OleC (e.g., SEQ ID NOS: 6, 14, 20), and OleD (e.g., SEQ ID NOS: 8, 16, 22). Similarly, when the starting material is an aliphatic ketone, the peptides OleC (e.g., SEQ ID NOS: 6, 14, 20) and OleD (e.g., SEQ ID NOS: 8, 16, 22) can be used in the in vitro reaction.

When a first peptide is used to convert a first intermediate to a second intermediate, and then a second peptide is used to convert the second intermediate to a third intermediate, the peptides can be added to the reaction simultaneously or serially. In some examples, where the peptides are added serially, the first peptide can be removed prior to the addition of the second peptide.

Additionally, a combination of chemical conversions and biological conversions can be used to produce a desired product. For example, one of ordinary skill in the art will appreciate that two fatty acids can be condensed to make an aliphatic ketone via chemical conversion and the resulting aliphatic ketone can then be converted to a hydrocarbon using biological conversions.

b. In Vivo

Given the disclosure provided herein, biocrude, hydrocarbon feedstocks, aliphatic ketones, hydrocarbons, and intermediates thereof can be produced in a recombinant cell. The recombinant cell can produce one or more peptides encoded by OleA (e.g., SEQ ID NOS: 2, 4, 12, 18), OleC (e.g., SEQ ID NOS: 6, 14, 20), OleD (e.g., SEQ ID NOS: 8, 16, 22), and OleB (e.g., SEQ ID NO: 10) and related sequences thereof (see Table 2). One of ordinary skill in the art will appreciate that the choice of peptides to express in the recombinant cell will depend upon the desired product and the starting material provided to the cells. For example, if the cell will be supplied with aliphatic ketones and the desired product is a hydrocarbon, the recombinant cell can be engineered to encode OleC (e.g., SEQ ID NOS: 6, 14, 20), and OleD (e.g., SEQ ID NOS: 8, 16, 22).

The in vivo methods described herein can also be used in combination with chemical conversions and in vitro biological conversions. For example, a first intermediate can be converted to a second intermediate using a peptide in vitro; the second intermediate can then be fed to a cell that expresses peptides necessary for the conversion of the second intermediate to a third intermediate. In another example, a first intermediate can be converted to a second intermediate via chemical conversion, and then the second intermediate can be fed to a recombinant cell encoding the peptides necessary for subsequent conversions.

Additionally, products can be produced using two or more in vivo reaction steps. For example, a first recombinant cell can be used to convert a first intermediate to a second intermediate. The second intermediate can be released from the cell, for example through passive transport, active transport or cell lysis, and the second intermediate can then be fed to a second recombinant cell where it is converted to a third intermediate. In some examples, the third intermediate will be the desired product.

The disclosure allows for the large scale production of aliphatic ketones, hydrocarbons, and intermediates that have defined carbon chain lengths, saturation levels, and branch points. The production of such engineered molecules provides a diversity of products that can be used as fuels and specialty chemicals.

IV. Production of Fuel

The biocrude or hydrocarbon feedstock is subjected to cracking to convert the high molecular weight hydrocarbons (for example, about $C_{14}$ to about $C_{40}$, about $C_{16}$ to about $C_{46}$, or about $C_{19}$ to about $C_{31}$, etc.) to cracked products which are lower molecular weight hydrocarbons (for example, about $C_1$ to about $C_{18}$, about $C_2$ to about $C_{14}$, about $C_3$ to about $C_{12}$, etc.). In certain embodiments, the cracking could selectively target the double bond positions for cleavage in the olefin(s) included in the biocrude or hydrocarbon feedstock. In other embodiments, the cracking targets both single bond and double bond positions. For example, a $C_{26}$ hydrocarbon with a single internal double bond could be cleaved to make two products, such as a $C_{12}$ alkane and a $C_{14}$ alkane. In another example, a $C_{26}$ hydrocarbon with two internal double bonds could be cleaved to make three products. Accordingly, the biocrude or hydrocarbon feedstock could provide an avenue for obtaining a diverse, but controllable, set of cracked products. The biocrude or hydrocarbon feedstock (e.g., an olefin-containing feedstock) is especially useful for producing high value products for jet fuel (e.g., $C_{14}$ to $C_{18}$), diesel (e.g., $C_8$ to $C_{14}$), and gasoline (e.g., $C_5$ to $C_{10}$). Illustrative methods of thermal cracking, hydrocracking, and catalytic cracking that can be used to further modify the cracked products produced are described herein, but other methods may also be used.

Cracking is an established and widely used process in the petroleum refining industry for converting hydrocarbonaceous feeds, such as petroleum oils of relatively high boiling point, to more valuable lower boiling products, including gasoline and middle distillates such as, kerosene, jet fuel, and heating oil. However, there are several drawbacks to cracking with petroleum feedstocks (in addition to the non-renewable characteristic of petroleum). Petroleum feedstock can contain a high amount of sulfur which can cause several problems, such as pollution and reforming catalyst poisoning. Petroleum feedstocks also include a broad range of compounds necessitating upstream removal processes, such as distillation. The biocrude or hydrocarbon feedstocks described herein may include a lower amount of sulfur, acid, salt, metal contaminants and/or nitrogen relative to petroleum feedstocks. The lower amounts of these contaminants should extend the life of the cracking catalyst and reduce refining costs. In addition, the biocrude or hydrogen feedstock can be tailored to contain a more narrow range of compounds compared to a petroleum feedstock. The predictability of the chemical composition and product distribution of the cracked product could be enhanced by controlling the content of the biocrude or hydrogen feedstock through recombinant engineering.

In addition, catalytic cracking of petroleum feedstocks typically is performed at a temperature of greater than 500° C. In certain embodiments of the presently disclosed processes the cracking can be performed at less than 500° C., such as down to 300°-350° C. Performing the cracking at such lower temperatures reduces the overall refining costs of producing biofuels.

Current cracking technologies for the production of light olefins (e.g., ethylene, propylene and, optionally, butylenes), gasoline and other cracked products, such as light paraffins and naphtha, can be classified into the categories of thermal cracking (also known as steam cracking), catalytic cracking, and hydrocracking.

Steam or thermal cracking, a robust technology that does not utilize catalyst, produces the more valuable ethylene as the primary light olefin product. It is particularly suitable for cracking paraffinic feedstocks to a wide range of products, including hydrogen, light olefins, light paraffins, and heavier liquid hydrocarbon products, such as pyrolysis gasoline, steam cracked gas oil, etc. Steam cracking utilizes sustained high cracking temperatures (about 850° C.) and high energy input. Sulfur addition is required to passivate the furnace metal surfaces on a continuous basis.

Catalytic cracking and hydrocracking technologies employ solid acid catalysts, such as zeolites, to promote cracking reactions. Hydrocracking also involves contacting the feedstock with a catalyst in the presence of hydrogen. Hydrocracking is a thermal catalytic process in which hydrogenation accompanies cracking. It is characterized by the rupture of carbon-carbon bonds and is accompanied by hydrogen saturation of the fragments to produce lower boiling products.

Catalytic cracking is preferred, but not required, for cracking the biocrude or hydrocarbon feedstock. The catalytic cracking is carried out in the absence of added hydrogen or in the absence of a substantial consumption of hydrogen. The presence of the carbon-carbon double bond(s) in the biocrude or hydrocarbon feedstock enables catalytic cracking at lower temperatures (e.g., 350° C. and below) and with a less expensive amorphous alumina-silica catalyst.

In general, catalytic cracking involves contacting the biocrude or hydrocarbon feedstock with at least one suitable catalyst. In particular, the biocrude or hydrocarbon feedstock can be contacted with at least one cracking catalyst at cracking conditions to produce a product stream comprising lower molecular weight hydrocarbons, such as $C_1$-$C_{18}$ hydrocarbons. In certain embodiments, the lower molecular weight hydrocarbons are alkanes and/or benzenes. Catalytic cracking typically can be classified as fluid catalytic cracking (FCC), moving-bed catalytic cracking or Thermofor catalytic cracking. Any, or a combination of, these unit processes may be used with the biocrude or hydrocarbon feedstocks disclosed herein. The cracking conditions (temperature, catalyst: hydrocarbon feedstock (or biocrude) ratio, flow rate, pressure, etc.) can be selected based upon the desired hydrocarbon conversion percentage and/or desired fraction distribution in the cracked product.

The cracking can be performed at any temperature. Illustrative temperatures include 100-600° C., more particularly 150-500° C., and most particularly 200-350° C. However, in certain embodiments, the cracking is performed at about 350° C. or less, more preferably at about 325° C. or less, and most preferably at about 300° C. or less. In certain examples, the biocrude or hydrocarbon feedstock is subjected to heat from a reactor environment in which the reactor temperature is set at the above-identified temperature(s). Cracking is an endothermic reaction that will lower the reaction mixture temperature as it progresses. Hence, the biocrude or hydrocarbon feedstock and/or catalyst may be pre-heated prior to mixing within the reactor. The pre-heating may be at a temperature that is higher or lower than the desired reaction temperature. Heat exchanger arrangement(s) may be used to pre-heat the biocrude or the hydrocarbon feedstock and/or supply the reaction heat.

The catalyst: hydrocarbon feedstock (or biocrude) wt ratio may vary depending upon the other operating conditions and the particular catalyst. For example, the catalyst: hydrocarbon feedstock (or biocrude) wt ratio may be about 30:1-1:1, about 25:1-1:1, about 20:1-2:1, about 18:1-3:1, etc.

Listed below are illustrative ranges of operating conditions for Fluid (FCC), Thermafor (TCC), and Houdry (HCC) Catalytic Cracking Units:

| | FCC | TCC | HCC |
|---|---|---|---|
| Reactor space velocity (lb/hr/lb) | 1.1-13.4 | 1-3 | 1.5-4 |
| Catalyst/feed ratio | 5-16 | 2-7 | 3-7 |
| Catalyst requirement, lb/bbl feed | .15-.25 | .06-.13 | .06-.13 |
| Reactor temp (C.) | 474-510 | 449-510 | 468-510 |
| Reactor pressure, psig | 8-30 | 8-12 | 9-10 |

The catalyst may be selected from any catalyst that can convert higher molecular weight hydrocarbons into lower molecular weight hydrocarbons. In general, cracking catalysts are an active amorphous clay-type catalyst and/or a high activity, crystalline molecular sieve. Illustrative catalysts include, but are not limited to, zeolite, aluminum hydrosilicate, treated bentonite clay, fuller's earth, bauxite, amorphous silica-alumina and mixtures or combination thereof.

Zeolites are the most commonly used molecular sieves in FCC processes. Suitable large pore zeolite components include synthetic zeolites, such as X-type and Y-type zeolites, mordenite and faujasite. Medium pore zeolites are exemplified by ZSM-5, ZSM-11, ZSM-12, ZSM-23, ZSM-35, ZSM-38, ZSM-48, and other similar materials. Other suitable medium pore zeolites include ferrierite, erionite, and ST-5, developed by Petroleos de Venezuela, S. A.

Catalytic cracking catalysts may comprise a zeolite component and a matrix component. The zeolite is a major contributor for the catalyst activity, selectivity and stability. Examples of the zeolite component include Y zeolite and beta zeolite. The zeolite usually is treated with various modifications, such as dealumination, rare earth exchange, phosphorous treatment, etc. Examples of typical matrix materials include amorphous compounds such as silica, alumina, silica-alumina, silica-magnesia, and clays such as kaolinite, halloysite or montmorillonite. The matrix component can serve several purposes. It can be used to bind the zeolite component to form catalyst particles. It can serve as a diffusion medium for the transport of feed and product molecules. It also can act as a filler which dilutes the zeolite particles to moderate the catalyst activity. In addition, the matrix can help heat transfer.

Some catalysts also contain additive catalyst(s), including, by way of non-limiting examples, octane-boosting additive, metal passivation additives, SOx reduction additives, NOx reduction additives, CO oxidation additives, coke oxidation additives, etc. The additive catalyst(s) can be either incorporated into the base catalyst matrix or used as separate catalyst particles. When used as separate catalyst particles, the additive catalyst(s) will contain, in addition to the catalytic active components, their own matrix materials, which may or may not be the same as the base catalyst matrix. Examples of the main catalytic components for octane-boosting additive catalysts include ZSM-5 zeolite, ZSM-11 zeolite, beta zeolite, etc. Examples of SOx reduction additives include magnesia, ceria-alumina, rare earths on alumina, etc. Examples of CO oxidation additives include platinum and/or palladium either directly added to the base catalyst at trace levels or dispersed on a support, such as alumina or silica alumina. Non-limiting examples of coke oxidation promoters include lanthanum and iron embedded in the base catalyst. Examples of metal passivation additives include barium titanium oxide, calcium-containing additives selected from the group consisting of calcium-titanium, calcium-zirconium, calcium-titanium-zirconium oxides and mixtures thereof, and antimony and/or tin on magnesium-containing clays.

In FCC, a pre-heated feed is brought into contact with a hot cracking catalyst in the form of a fine powder, typically having a particle size of about 10 to about 300 microns, usually about 60 to 70 microns, for the desired cracking reactions to take place. During cracking, coke and hydrocarbon material are deposited on the catalyst particles resulting in a loss of catalyst activity and selectivity. The coked catalyst particles, and associated hydrocarbon material, are subjected to a stripping process, usually with steam, to remove as much of the hydrocarbon material as technically and economically feasible. The stripped particles, containing non-strippable coke, are removed from the stripper and sent to a regenerator where the coked catalyst particles are regenerated by contact with air, or a mixture of air and oxygen, at an elevated temperature resulting in the combustion of the coke. The combustion is a strongly exothermic reaction which removes the coke and heats the catalyst to temperatures appropriate for the endothermic cracking reaction. The process is carried out in an integrated unit comprising a fluidized cracking reactor, a stripper, a regenerator, and appropriate ancillary equipment. The catalyst is continuously circulated from the reactor, or reaction zone, to the stripper and then to the regenerator and back to the reactor. The circulation rate is typically adjusted relative to the feed rate of the biocrude or hydrocarbon feedstock to maintain a heat balanced operation in which the heat produced in the regenerator is sufficient for maintaining the cracking reaction with the circulating regenerated catalyst being used as the heat transfer medium. Typical fluid catalytic cracking processes are described in the monograph Fluid Catalytic Cracking with Zeolite Catalysts, Venuto, P. B. and Habib, E. T., Marcel Dekker Inc. N.Y. 1979, which is incorporated herein by reference. As described in this monograph, catalysts that are conventionally used are based on zeolites, especially the large pore synthetic faujasites, zeolites X and Y.

Illustrative catalytic cracking catalysts can be comprised of a crystalline tetrahedral framework oxide component. This component catalyzes the breakdown of primary products from the catalytic cracking reaction into clean products, such as naphtha for fuels and olefins for chemical feedstocks. The crystalline tetrahedral framework oxide component may be selected from the group consisting of zeolites, tectosilicates, tetrahedral aluminophosphates (ALPOs), and tetrahedral silicoaluminophosphates (SAPOs). Non-limiting examples of zeolites include gmelinite, chabazite, dachiardite, clinoptilolite, faujasite, heulandite, analcite, levynite, erionite, sodalite, cancrinite, nepheline, lazurite, scolecite, natrolite, offretite, mesolite, mordenite, brewsterite, and ferrierite. Included among the synthetic zeolites are zeolites X, Y, A, L, ZK-4, ZK-5, B, E, F, H, J, M, Q, T, W, Z, alpha, beta, omega, and USY zeolites.

A combination of catalytic cracking and hydrocracking can be used with the above-described olefin-containing feedstock. For example, the biocrude or hydrocarbon feedstock could be initially subjected to catalytic cracking to a predetermined extent and subsequently subjected to hydrocracking, or the order of the unit processes could be reversed.

The cracked product may be separated, or is separable, into various fractions. For example, the cracked product may be charged to a fractionating column where it is separated into fractions. The separation may be accomplished by any separation technique, particularly distillation.

The cracking conditions and hydrocarbon feedstock (or biocrude) compound distribution may be adjusted to achieve any described conversion level. As used herein, "conversion" refers to the amount in wt % of hydrocarbons in the feed that are converted to lower molecular weight hydrocarbons. In certain embodiments, the conversion may be about 40 to about 85%, more particularly about 55 to about 75%, and most particularly about 70%. One hundred percent conversion typically is undesirable because it typically correlates with nearly 100% conversion of material to coke. A 70% conversion is desirable because it generally equates to about 50% of the cracked product being converted to $C_{5+}$ compounds.

The cracked product may contain $C_1$-$C_{18}$ hydrocarbons, as well as impurities, contaminants, higher molecular weight hydrocarbons that have not undergone conversion or only a partial conversion, and/or other by-products, such as hydrocarbon products. The $C_1$-$C_{18}$ hydrocarbons may include alkenes, alkanes, cycloalkanes, and aromatic compounds.

In certain embodiments, the cracked product may include about 50 wt % or lower of $C_4$ or lower (i.e., a light gas mixture fraction) hydrocarbons, based on the total hydrocarbon amount in the cracked product. In further embodiments, the cracked product may include at least about 50 wt % of $C_5$ or greater hydrocarbons, based on the total hydrocarbon amount in the cracked product.

In certain embodiments, the cracked product may also include various fractions, such as a gasoline, jet fuel, or diesel fractions. In one embodiment, these fractions distill at certain temperature ranges at 1 atm:

gasoline fraction at about 20 to about 210° C.;
jet fuel fraction at about 170 to about 290° C.; and/or
diesel fraction at about 180 to about 320° C.

In further embodiments, the cracked product may include various fractions based upon carbon chain length, such as $C_5$-$C_{10}$, $C_8$-$C_{14}$, or $C_{14}$-$C_{18}$. In one embodiment, these carbon chain length fractions have certain boiling point ranges at 1 atm:

$C_5$-$C_{10}$ fraction at about 30 to about 180° C.;
$C_8$-$C_{14}$ fraction at about 120 to about 260° C.; and/or
$C_{14}$-$C_{18}$ fraction at about 230 to about 320° C.

The cracked product may be completely or partially separated into the various fractions. The fractions can be used as fuels, lubricants, petrochemical feedstocks, and other uses as known in the petroleum industry.

The cracked product may by completely or partially separated into a gasoline, diesel, and/or jet fuel fractions. In one embodiment, the cracked product is comprised of at least about 10, 20, 30, 40, 50 or 60 wt. % of a gasoline fraction based upon the total amount of cracked product. In another embodiment, the cracked product is comprised of at least about 10, 20, 30, 40, 50 or 60 wt. % of a diesel fraction based upon the total amount of cracked product.

The cracked product also may be blended with at least one other fuel component. The un-separated cracked product may be blended or at least one of the fractions may be separated prior to blending. Illustrative fuel components for blending include petroleum-based fuels such as gasoline, diesel or jet fuel. Other fuel components include other fuels derived from renewable resources, such as bioethanol. In addition, additives, such as methanol, ethanol, TBA, MTBE, ETBE, or TAME, can be blended with the fuel. The cracked product/other fuel component blend may be used directly for its end purpose (as a transportation fuel) or the blend may be subjected to further refining.

In another embodiment, the biocrude or hydrocarbon feedstock may be blended with a petroleum-based crude. The resulting biocrude/petroleum crude blend can then be subjected to cracking. This blend may lower the overall cracking temperature, reduce the amount of undesired methane produced, and/or reduce coking.

EXAMPLES

Example 1

General Methods

This example describes materials and methods used in carrying out Examples 2-7. Although particular methods are described, one of skill in the art will understand that other, similar methods also can be used. In general, standard laboratory practices are used for cloning, manipulation and sequencing of nucleic acids, and purification and analysis of proteins and other molecular biological and biochemical techniques, unless otherwise stipulated. Such techniques are explained in detail in standard laboratory manuals such as Sambrook et al., *Molecular Cloning: A Laboratory Manual,* 3rd ed., vol. 1-3, Cold Spring Harbor, N.Y., 2000; and Ausubel et al., Current Protocols in Molecular Biology, Greene Publ. Assoc. & Wiley-Intersciences, 1989.

Genome Sequences

The complete genome sequence of *Stenotrophomonas maltophilia* is available to the public for two different strains. The complete genome sequence for *Stenotrophomonas maltophilia* R551-3 can be found at //genome.ornl.gov/microbial/smal/ (last accessed on May 16, 2007). The complete genome sequence for *Stenotrophomonas maltophilia* strain K279a can be found at //www.sanger.ac.uk/Projects/S_maltophilia/ (last accessed on May 16, 2007). The proteins described herein are found in both sequenced genomes, and were experimentally confirmed in ATCC strain 17679.

Bacterial Strains

The bacterial strains used herein were as follows:

*Stenotrophomonas maltophilia* (ATCC strain numbers: 17674, 17679, 17445, 17666)

*Escherichia coli* (specific strains for expression from the T7 promoter)

*E. coli* T7 Express lysY/Iq (New England Biolabs, Ipswich, Mass. 01938-2723)

*E. coli* C41(DE3) (Lucigen Corporation, Middleton, Wis. 53562)

*E. coli* C41(DE3) ΔfadE (the *E. coli* C41(DE3) strain from Lucigen Corporation, Middleton, Wis. 53562 with a deletion of the fadE gene EC 1.3.99.3, an acyl-CoA dehydrogenase, Klein. K. et al., *Eur. J. Biochem. II I* 19:442-450, 1971)

Resistance Markers

AmpR, ampicillin/carbenicillin (50 μg/mL); KanR, kanamycin (30 μg/mL); CamR, chloramphenicol (34 μg/mL); SmR, streptomycin/spectinomycin (50 μg/mL).

Polymerase Chain Reaction (PCR)

PCR was used to amplify the specified nucleic acid sequences from genomic DNA isolated from *Stenotrophomonas maltophilia* to create the expression construct. The primers used for each PCR reaction are listed in Table 3, and the inserts that correlate with the expression plasmids are listed in Table 3.

TABLE 3

| Primers | |
|---|---|
| Name | Sequence 5' to 3' |
| Gene 1: /locus—tag = "OleA" (SEQ ID NO: 29 and 30) | |
| LB118 | GATAcatATGCTCTTCAAGAATGTCTCG |
| LB119 | TCAGctcgagCCAGACCACTTCAGCCATCGAG |
| Gene 2: /locus—tag = "OleC" (SEQ ID NO: 31 and 32) | |
| LB155 | GATA*catATG*AACCGACCCTGCAATATTGC |
| LB159 | TCAGctcgagTCATGCGCGCTTCTCCAGTTCGGCGCTGGC |
| Gene 3: /locus—tag = "OleD" (SEQ ID NO: 33 and 34) | |
| LB157 | GATA*catATG*AAGATCCTGGTCACCGGTGGTGG |
| LB158 | TCAGctcgagCTATGCGGCAGATGAAGCCTTCAG |
| Gene 4: /locus—tag = "OleB" (SEQ ID NOS: 35 and 36) | |
| LB151 | GATA*catATG*TCCCAGCTTCCCGGTTACC |
| LB152 | TCAGctcgagTCAGATCGGGTTCTTGTCCAGG |

TABLE 3-continued

| Primers | |
|---|---|
| Name | Sequence 5' to 3' |
| Gene 1 and 4 as an operon (SEQ ID NOS: 29 and 36) | |
| LB118 | GATAcatATGCTCTTCAAGAATGTCTCG |
| LB152 | TCAGctcgagTCAGATCGGGTTCTTGTCCAGG |
| Gene 2 and 3 as an operon (SEQ ID NOS: 31 and 34) | |
| LB155 | GATA*catATG*AACCGACCCTGCAATATTGC |
| LB158 | TCAGctcgagCTATGCGGCAGATGAAGCCTTCAG |
| Primers used to clone additional hydrocarbon producing genes (SEQ ID NOS: 37-42) | |
| LF305 | GGATacATGttaTTCAAAAATGTATCTATC |
| LF306 | CTCGAGAAGCttaCCACACAACCTCAGCC. |
| LF307 | GGATACATGttaTTTCAGAATGTTTCTATCGC |
| LF308 | CTCGAGaagcttaCCAAACCACTTCGGCCATGCTG |
| LF313 | GGATACATGTTATTCAAGCACGTCATGATCG |
| LF314 | CTCGAGAAGCTTACCACGTAACGGACATCATAG |

TABLE 4

| Plasmids | | | |
|---|---|---|---|
| Vectors | | | Source |
| pET-21b(+) | | | EMD Chemicals, Inc., San Diego, CA |
| pCOLADuet-1 | | | EMD Chemicals, Inc., San Diego, CA |
| pCDFDuet-1 | | | EMD Chemicals, Inc., San Diego, CA |
| pETDuet-1 | | | EMD Chemicals, Inc., San Diego, CA |
| pACYCDuet-1 | | | EMD Chemicals, Inc., San Diego, CA |
| pJ201 | | | DNA2.0 Menlo Park, CA |
| Expression Constructs | Vector | Insert | |
| ORF1: OleA (SEQ ID NO: 2) | pET-21b, or pCOLADuet-1 cut with NdeI and XhoI | PCR product derived from primers LB118 and LB119 cut with NdeI and XhoI | Described herein |
| ORF2: OleC (SEQ ID NO: 4) | above vectors cut with NdeI and XhoI | PCR product derived from primers LB155 and LB159 cut with NdeI and XhoI | Described herein |
| ORF3: OleD (SEQ ID NO: 8) | above vectors cut with NdeI and XhoI | PCR product derived from primers LB157 and LB158 cut with NdeI and XhoI | Described herein |
| ORF4: OleB (SEQ ID NO: 10) | above vectors cut with NdeI and XhoI | PCR product derived from primers LB151 and LB152 cut with NdeI and XhoI | Described herein |
| ORF1 and ORF4: OleA (SEQ ID NO: 2) OleB (SEQ ID NO: 10) | above vectors cut with NdeI and XhoI | PCR product derived from primers LB118 and LB152 cut with NdeI and XhoI | Described herein |
| ORF2 and ORF3: OleC (SEQ ID NO: 6) OleD (SEQ ID NO: 8) | above vectors cut with NdeI and XhoI | PCR product derived from primers LB155 and LB158 cut with NdeI and XhoI | Described herein |
| OleA codon optimized (CO) *S. maltophilia* | pET-21d, or pCOLADuet-1 cut with NcoI and HindIII | PCR product derived from primers LB305 and LB306 cut with PciI and HindIII | Described herein |
| OleA *Xanthomonas axonopodis* | above vectors cut with NcoI and HindIII | PCR product derived from primers LB307 and LB308 cut with PciI and HindIII | Described herein |

TABLE 4-continued

| Plasmids | | | |
|---|---|---|---|
| OleA Chloroflexus aggregans | above vectors cut with NcoI and HindIII | PCR product derived from primers LB314 and LB315 cut with PciI and HindIII | Described herein |
| OleD *Xanthomonas axonopodis* | above vectors cut with NcoI and HindIII | synthetic DNA restriction fragment cut with NcoI and HindIII encoding the Xanthomonas axonopodis OleD protein | Described herein |
| OleC *Xanthomonas axonopodis* | above vectors cut with NcoI and HindIII | synthetic DNA restriction fragment cut with NcoI and HindIII encoding the *Xanthomonas axonopodis* OleC protein | Described herein |
| FadD an acyl-CoA synthetase from *Escherichia coli* str. K12 substr. W3110 Genebank Accession # BAA15609 | pCDFDuet-1 vector cut with NcoI and HindIII | PCR product from *E. coli* | Described herein |
| TesA gene (thioesterase A gene Genbank accession #AAA24664 without leader sequence (Cho and Cronan, The J of Biol. Chem., 270: 4216-9, 1995) from *E. coli* | pETDuet-1 vector cut with NdeI and AvrII | PCR product from *E. coli* | Described herein |

Cloning Methods

Standard DNA molecular biology cloning procedures were used to clone into the vectors described in the plasmid table (Sambrook et al., *Molecular Cloning: A Laboratory Manual,* 3rd ed., vol. 1-3, Cold Spring Harbor, N.Y., 2000). Restriction enzymes NdeI and XhoI were purchased from New England Biolabs.

T7 Expression Protocol

Standard induction protocols were used:

Medium: Luria Broth

Volume: 5 mL

Induction: 1 mM IPTG

Time: 6 to 24 hours

Temperature: 25° C., 30° C. or 37° C.

Cell Lysate Protocol

Standard cell lysis protocols were used:

Cell pellets were disrupted by sonication and/or by the use of the BugBuster plus benzonase reagent kit (Catalog #70750 Novagen of EMD Chemicals, Inc., San Diego, Calif.). For example, a 10 mL culture was centrifuged in a falcon tube at 3500 rpm for 15 minutes, and the resulting pellet was resuspended in 2 mL of BugBuster and 2 μL it of Benzonase.

Protein Purification Protocol

His-tagged proteins were purified using standard procedures. Proteins were purified according to the instructions found in User protocol TB054 Rev. F0106 (Novagen of EMD Chemicals, Inc., San Diego, Calif.)

Hydrocarbon Product Detection: Extraction Methods

Extraction Method 1:

Organic compounds (olefins, aliphatic ketones and hydrocarbons) were extracted from bacterial cell pellets using a methanol: hexane extraction protocol. Briefly, 5 mL of cell pellet was centrifuged in a glass test tube at 3500 rpm for 15 minutes, and the resulting pellet was resuspended in 100 μL of sterile distilled water and vortexed until homogenous. Next, 1 mL of methanol was added and mixed by vortex. The sample was then sonicated for 15 minutes to 1.5 hours in a sonicating water bath. Following the sonication, 4 mL of hexane was added and the sample was vortexed. The samples were then centrifuged at 3500 rpm for 15 minutes. The upper layer (hexane layer) was removed and added to a clean glass tube. The sample was then dried in a Speedvac for approximately 30 minutes until essentially no solvent was present. The sample was then resuspended in 100 μL of ethylacetate or chloroform, and 1 μL of the sample was run on the GC/MS.

Extraction Method 2:

For the in vitro assays olefins, aliphatic ketones and hydrocarbons were extracted from bacterial cell pellets using an ethylacetate/1% acetic acid extraction protocol. In vitro assay samples were extracted by the addition of 500 μL of ethylacetate containing 1% acetic acid. The sample was mixed by vortexing followed by centrifugation at 3500 rpm for 5 minutes to separate the aqueous and organic layers. The top layer (ethylacetate layer) was transferred to a clean tube. The sample was then dried in a Speedvac until essentially no solvent was present. The sample was resuspended in 50 μL of ethylacetate and analyzed by GC/MS. Between 1 and 10 μL were run on the GC/MS and analyzed for hydrocarbon content.

Hydrocarbon Product Detection: Detection Method

For GC/MS detection, hydrocarbons were detected and verified using the following protocol:

Run Time: 20 minutes

Column: HP-5-MS (5% diphenyl siloxane 95% dimethyl siloxane) Part No. 19091S-433E, Length: (meters) 30, I.D.: (mm) 0.25 narrow bore, Film: (μM) 0.25

MSD Scan Range: 50-800 M/Z

Inject: 1 μL Agilent 6850 inlet

Inlet: 300° C. splitless

Carrier gas: Helium

Oven Temp: 5 minute hold 100° C.; 25° C./minute to 320° C.; 5 minute hold 320° C.

Det; Agilent 5975B VL MSD

Det. Temp: 300° C.

Example 2

Expression of ORF 1, 2 and 3 (OleA (SEQ ID NO: 2), OleC (SEQ ID NO: 6), and OleD (SEQ ID NO: 8)) Results in the Production of Olefins This example demonstrates that expression of ORF 1, 2 and 3 (OleA (SEQ ID NO: 2), OleC (SEQ ID NO: 6), and OleD (SEQ ID NO: 8) in *E. coli* cells results in the production of olefins. Similar methods can be used to express these in any cell of interest.

The OleA (SEQ ID NO: 1), OleC (SEQ ID NO: 3), and OleD (SEQ ID NO: 5) nucleic acid sequences were amplified as described above from *S. maltophilia* using the following primers: the nucleic acid sequence encoding OleA (SEQ ID NO: 1) was amplified using forward primer LB118 (SEQ ID NO: 29) and reverse primer LB119 (SEQ ID NO: 30); the nucleic acid sequence encoding OleC (SEQ ID NO: 3) was amplified using forward primer LB155 (SEQ ID NO: 31) and reverse primer LB159 (SEQ ID NO: 32); OleD (SEQ ID NO: 5) was amplified using forward primer LB157 (SEQ ID NO: 33) and reverse primer LB158 (SEQ ID NO: 34).

The OleA (SEQ ID NO: 7) amplification product was inserted into pET-21b or pCOLADuet-1 using the restriction enzymes NdeI and XhoI, and the OleC (SEQ ID NO: 3) and OleD (SEQ ID NO: 5) amplification products were inserted into pET-21b or pCOLADuet-1 using the restriction enzymes NdeI and XhoI. The plasmids were then used to transform *E. coli* (T7 Express lysY/Iq) as described above, and the bacteria were cultured as described in Example 1 and induced with IPTG. Cells were pelleted, extracted, and detected by GC/MS.

Figure 3:
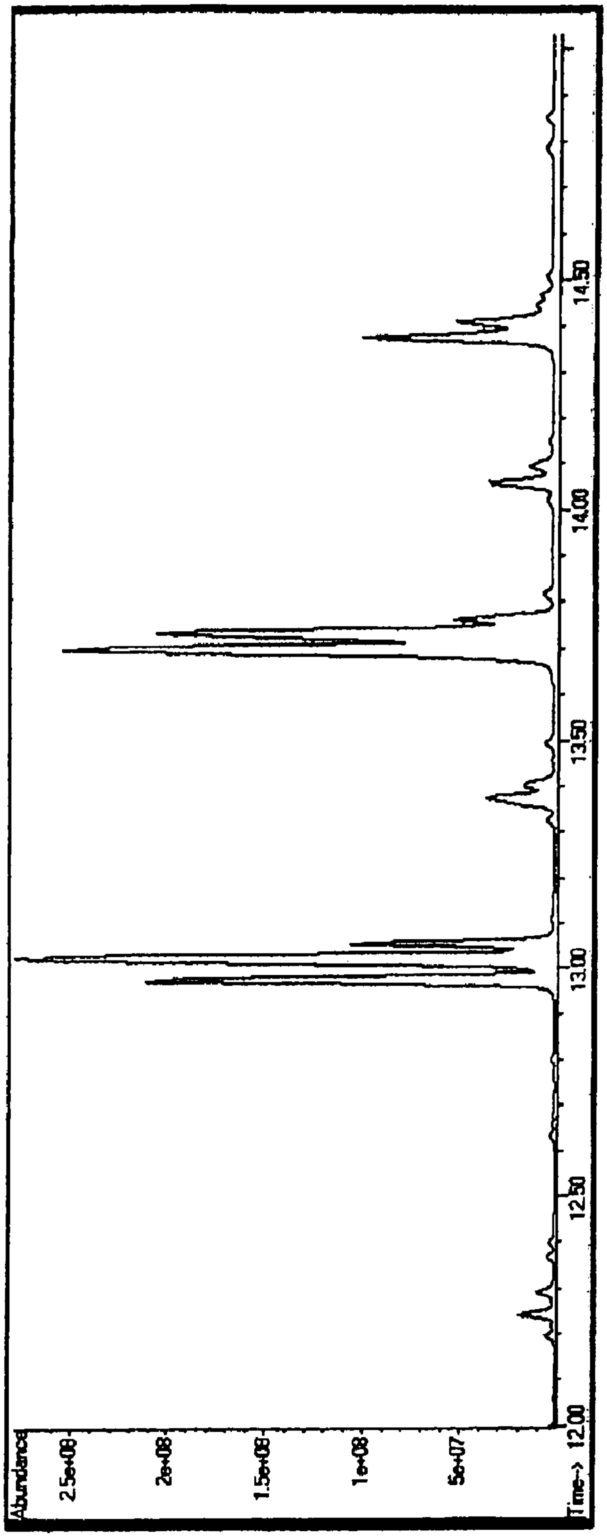
FIG. 3 is a total ion chromatogram of hydrocarbons extracted from *E. coli* expressing proteins OleA (SEQ ID NO: 2), OleC (SEQ ID NO: 6), and OleD (SEQ ID NO: 8).
Figure 5:
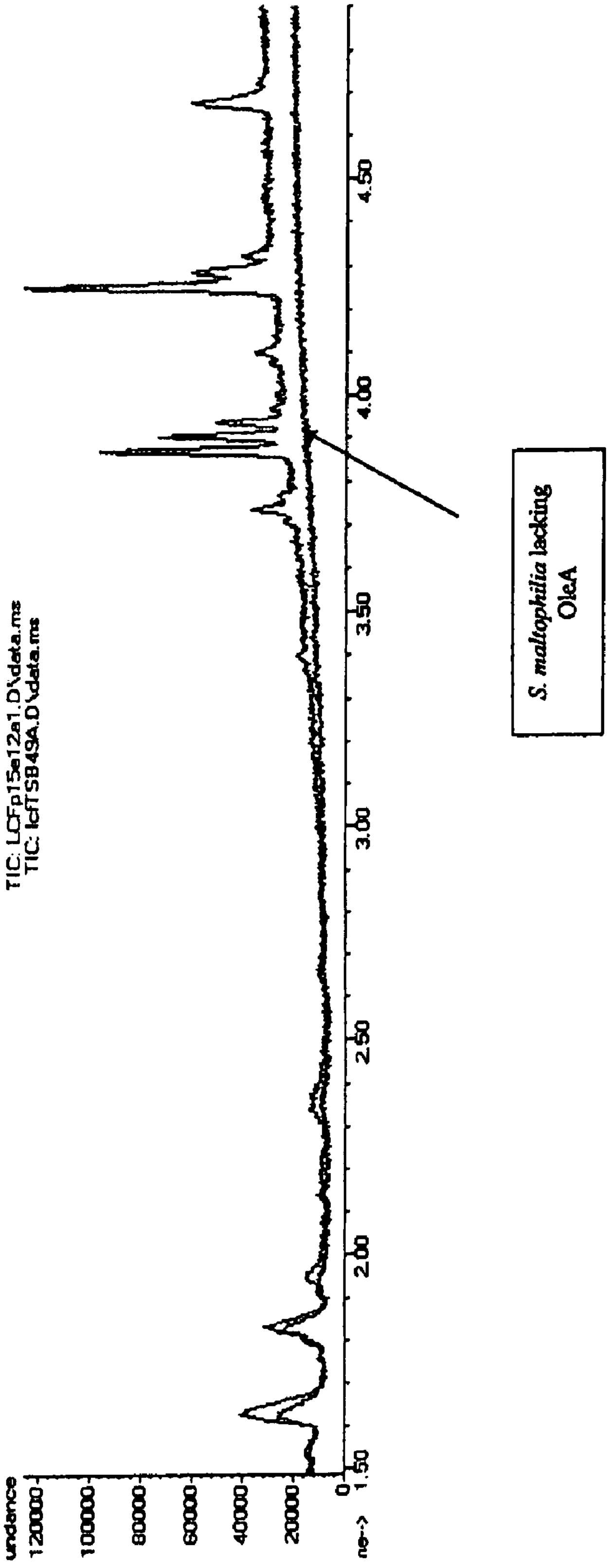
FIG. 5 is a total ion chromatogram comparing the hydrocarbons extracted from a mutant *S. maltophilia* lacking OleA (SEQ ID NO: 2) with a wild type *S. maltophilia.*

The hydrocarbons detected by GC/MS were: 1) mono, 2) di unsaturated, and 3) tri unsaturated chains that ranged from $C_{27}$ to $C_{31}$ (FIGS. 3 and 4). Thus, the olefin structures (for instance, the degree of saturation, chain length, and presence of branched or unbranched chains) depend on the host background. For instance, when *E. coli* was used as a host strain, the olefins indicated in FIG. 3 were produced. These olefins differ from those produced by *S. maltophilia* (FIG. 5). These differences are a direct reflection of the organism's ability to produce various types of fatty acyl chains (part of the fatty acid biosynthetic pathway), demonstrating that if the fatty acid biosynthetic machinery is altered, the types of olefins produced are altered.

When ORFI (OleA; SEQ ID NO: 2) is knocked out in *S. maltophilia*, the strain is no longer capable of producing olefins (FIG. 5).

Example 3

In Vitro Method of Identifying Acyl-Condensing Activity

This example demonstrates the ability to detect aliphatic ketone production using an in vitro assay combining purified enzyme (e.g., OleA protein) with purified substrate (e.g., acyl coenzyme A, acyl-ACP, etc.) in a 0.1 M phosphate buffer pH 7.0.

OleA (SEQ ID NO: 2) was expressed in *E. coli* as described in Examples 1 and 2, and the resulting recombinant bacteria were cultured, induced, pelleted, and used to make purified OleA protein as described above. The in vitro assay mixture consisted of a substrate diluted to a final concentration of 0.1 mM to 1 mM (e.g., acyl coenzyme A, acyl-ACP or a mixture of acyl coenzyme A and acyl-ACP), 20 μL of a 0.6 mg/mL solution of purified OleA protein in a 0.1 M phosphate buffer pH 7.0 with 500 mm magnesium chloride. Each assay mixture was incubated at 37° C. for 1 hour. After the incubation period, 250 μL of ethylacetate was added to each assay mixture and each assay mixture was mixed by vortex for 10 minutes. The ethylacetate fraction of the assay mixture was separated from the aqueous phase by centrifugation in a microcentrifuge at 3000 rpm for 5 minutes. 15 μL of the ethylacetate fraction (i.e., the top layer) was transferred into a GC/MS vial to which 1.5 μL of a 0.1 mg/mL solution of hexacosane solution was added as a control spike into each ethylacetate fraction before each ethyl acetate fraction was analyzed on the GC/MS.

Saturated aliphatic ketones, mono-unsaturated and di-unsaturated aliphatic ketones have been detected with carbon chain lengths ranging from 19 to 32 carbons in length. Aliphatic ketone was not detected in any of the control assay mixtures (e.g., assay mixtures containing purified enzyme without substrate and assay mixtures containing purified substrate without enzyme).

Table 5 illustrates the combinations of substrates that were tested and the types of products that were produced. Table 5 also shows the resulting aliphatic ketones detected from each respective combination of substrates provided in the assay mixture. Aliphatic ketones were formed by the following combinations of substrates: acyl-CoA with acyl-CoA, acyl-ACP with acyl-ACP and acyl-CoA with acyl-ACP (data from each combination are shown in Tables 5, 6, and 7, respectively). The substrates are shown across the top and left side of the table and each entry shows the length and unsaturation of the aliphatic ketone that was formed.

TABLE 5

| | Acyl coA | | | | |
|---|---|---|---|---|---|
| Acyl coA | C10 | C12 | C14 | C16 | C16:1 |
| C10 | C19 | N/A | C23 | N/A | N/A |
| C12 | — | C23 | C25 | | C27:1 |
| C14 | — | — | C27 | C29 | C29:1 |
| C16 | — | — | — | C31 | C31:1 |
| C16:1 | — | — | — | — | C31:2 |

N/A - have not been tested.

TABLE 6

| | Acyl ACP | | | | |
|---|---|---|---|---|---|
| Acyl ACP | C10 | C12 | C14 | C14:1 | C16:1 |
| C10 | C19 | N/A | C23 | N/A | N/A |
| C12 | — | C23 | C25 | N/A | C27:1 |
| C14 | — | — | C27 | C27:1 | C29:1 |
| C14:1 | — | — | — | C27:2 | N/A |
| C16:1 | — | — | — | — | C31:2 |

N/A - have not been tested.

TABLE 7

| Substrate | C14-ACP |
|---|---|
| C16:1-CoA | C27, C29:1, C31:2 |

Example 4

Identification of Additional OleA, OleC, and OleD Sequences

This example describes the identification of active OleA, OleC and OleD sequences using the *S. maltophilia* sequences described herein. The amino acid sequences of proteins related to the *S. maltophilia* OleA, OleC and OleD sequences were determined by using the NCBI BLAST protein alignment tool to search the nr database. To demonstrate how to identify and test for the activity of additional members of the OleA, OleC and OleD genera, genes from a closely related organism, *Xanthomonas axonopodis* (OleA, OleC and OleD), and genes from two distantly related organisms, *Chloroflexus aggregans* (OleA, OleC and OleD) and *Plesiocystis pacifica* (OleC), were cloned and tested as follows.

The plasmids used in this example were made using the same bacterial strains, resistance markers, and PCR techniques described above. For a more detailed description of the plasmids see Table 4. Similarly, the T7 expression protocol, hydrocarbon extraction methods and hydrocarbon detection methods described above were used to identify hydrocarbons and hydrocarbon intermediates.

The genes of interest were designed to be optimized for expression in *E. coli* using the Protein-2-DNA software (Gustafsson C. et al., *Trends Biotechnol* 22(7):346-353, 2004) to select a codon distribution mimicking natural highly expressed *E. coli* proteins (Henaut A and Danchin A: analysis and predictions from *Escherichia coli* sequences. In *E. coli* and *Salmonella typhimurium* cellular and molecular biology Volume 2 Edited by: Neidhardt F C, Curtiss RIII, Ingraham J, Lin E, Brooks Low et al. Washington D.C. ASM press 1996: 2047-2066). The gene(s) were synthesized by non-template PCR similar to what has previously been described (See, e.g., Dillon P J, Rosen C A: A rapid method for the construction of synthetic genes using the polymerase chain reaction. Biotechniques 1990, 9:298-300). Gene synthesis was performed by DNA2.0 (Menlo Park, Calif.).

The synthetic open reading frames were cloned into plasmid pJ201 (DNA 2.0, Menlo Park, Calif.). These genes were subcloned into pET 21d upstream of the T7 promoter in the multiple cloning site between NcoI and HindIII sites. Primers were designed to conserve the 5' and 3' ends of the protein sequences. The codon optimized version of OleA based on the amino acid sequence from *S. maltophilia* was PCR amplified from the DNA 2.0 plasmid using the LF305 and LF306 primers (see, Table 3 for primer sequences). The PCR product was digested with PciI and HindIII and cloned into the pET21d vector. The OleA open reading frame based on the amino acid sequence of *Xanthomonas axonopodis* GenBank accession #NP_640589.1 GI:21241007 was PCR amplified from the DNA 2.0 plasmid using primers LF307 and LF308. The PCR product was digested with PciI and HindIII and cloned into the pET21d vector. The OleA open reading frame based on the amino acid sequence of *Chloroflexus aggregans* DSM 9485 NCBI GenBank accession #ZP_01515932.1 GI:118047293 was PCR amplified from the DNA 2.0 plasmid using primers LF313 and LF314. The PCR product was digested with PciI and HindIII and cloned into the pET21d vector.

The synthetic versions of OleC and OleD genes from *Xanthomonas axonopodis* and *Chloroflexus aggregans* and the OleC gene from *Plesiocystis pacifica* were directly subcloned from the DNA 2.0 pJ201 vectors in front of the T7 promoter in the pCOLADuet vector using NcoI and HindIII.

The aliphatic ketone producing activity of OleA was assessed by identifying the production of aliphatic ketones when OleA was expressed in *E. coli*. Cells were transformed with the plasmid of interest, induced using the described T7 expression protocol and the pellets were extracted and analyzed for the production of aliphatic ketone by GC/MS.

The hydrocarbon synthase activity of OleC and OleD was assessed by using a complementation assay and testing for olefin production. The activity of OleC was assessed in an *E. coli* that also expressed OleA and OleD from *S. maltophilia*. More specifically, cells were transformed with three plasmids carrying OleA (*S. maltophilia*), OleC (organisms of interest) and OleD (*S. maltophilia*). They were subjected to the T7 expression protocol and the pellets were extracted and analyzed for the production of olefins by GC/MS.

Similarly, the hydrocarbon synthase activity of OleD was assessed in the presence of OleA and OleC from *S. maltophilia*. Cells are transformed with three plasmids carrying OleA (*S. maltophilia*), OleC (*S. maltophilia*) and OleD (organisms of interest). They were subjected to the T7 expression protocol, and the pellets were extracted and analyzed for the production of olefins by GC/MS.

The results from the expression of OleA showed that the three related OleA protein sequences from *Stenotrophomonas maltophilia, Xanthomonas axonopodis* and *Chloroflexus aggregans* all function to produce aliphatic ketones when expressed in *E. coli* C41(DE3). The aliphatic ketones detected by GC/MS were: 1) saturated; 2) mono unsaturated; and 3) di unsaturated. The aliphatic ketones ranged in carbon chain length from $C_{27}$ to $C_{31}$.

The results from the expression of OleC expression in combination with OleA and OleD showed that the three related OleC protein sequences from *Xanthomonas axonopodis, Chloroflexus aggregans* and *Plesiocystis pacifica* all function to produce olefins when expressed in *E. coli* C41 (DE3) expressing known functional OleA and OleD genes. The olefins detected by GC/MS were: 1) saturated; 2) mono unsaturated; and 3) di unsaturated. The olefins ranged in carbon chain length from $C_{27}$ to $C_{31}$.

Similarly, the results from the expression of OleD expression in combination with OleA and OleC showed that the two related OleD protein sequences from *Xanthomonas axonopodis* and *Chloroflexus aggregans* both function to produce olefins when expressed in *E. coli* C41(DE3) expressing known functional OleA and OleC genes. The olefins detected by GC/MS were: 1) saturated; 2) mono unsaturated; and 3) di unsaturated. The olefins ranged in carbon chain length from $C_{27}$ to $C_{31}$ (Table 8).

TABLE 8

| Protein | Organism | DNA | Aliphatic Ketone | | | | | | | |
|---|---|---|---|---|---|---|---|---|---|---|
| | | | C27 | C27:1 | C27:2 | C29 | C29:1 | C29:2 | C31:1 | C31:2 |
| OleA | *Stenotrophomonas maltophilia* ATCC17679 | native | + | + | + | + | + | + | + | + |
| OleA | *Stenotrophomonas maltophilia* R551-3 | synthetic | + | + | + | + | + | + | + | + |

TABLE 8-continued

| Protein | Organism | DNA | | | | | | | | |
|---|---|---|---|---|---|---|---|---|---|---|
| OleA | *Xanthomonas axonopodis* | synthetic | + | + | + | + | + | + | + | + |
| OleA | *Chloroflexus aggregans* | synthetic | + | + | + | + | + | + | + | + |
| | | | Olefin* | | | | | | | |
| | | | C27:1 | C27:2 | C27:3 | C29:1 | C29:2 | C29:3 | C31:2 | C31:3 |
| OleC | *Stenotrophomonas maltophilia* ATCC17679 | native | + | + | + | + | + | + | + | + |
| OleC | *Xanthomonas axonopodis* | synthetic | + | + | + | + | + | + | + | + |
| OleC | *Chloroflexus aggregans* | synthetic | + | + | + | + | + | + | + | + |
| OleC | *Plesiocystis pacifica* | synthetic | + | + | + | + | + | + | + | + |
| | | | Olefin* | | | | | | | |
| | | | C27:1 | C27:2 | C27:3 | C29:1 | C29:2 | C29:3 | C31:2 | C31:3 |
| OleD | *Stenotrophomonas maltophilia* ATCC17679 | native | + | + | + | + | + | + | + | + |
| OleD | *Xanthomonas axonopodis* | synthetic | + | + | + | + | + | + | + | + |
| OleD | *Chloroflexus aggregans* | synthetic | + | + | + | + | + | + | + | + |

*OleC was tested in the presence of OleA and OleD from *Stenotrophomonas maltophilia* ATCC17679. OleD was tested in the presence of OleA and OleC from *Stenotrophomonas maltophilia* ATCC17679.

Example 5

Identification of Amino Acid Motifs Common to OleA

This example provides 6 motifs (motifs 2-7 in Table 9) that can be used to identify additional OleA genes. One or more of these motifs can be submitted to the NR database and the result set will contain additional OleA genes.

Briefly, programs to search protein databases for specific amino acid patterns (Motifs) are available over the Internet. One such program is available on the Internet and offered by GenomeNet service through the Kyoto University Bioinformatics Center. The website, as of Aug. 1, 2007, was http://motifgenome.jp/MOTIF2.html. This motif searching program offers the user the ability to search the following databases: Swiss-Prot, PDBSTR, FIR, PRF, GENES and NR-AA. The user enters the specific amino acid pattern in the PROSITE format (Hofmann et al., *Nucleic Acids Res.* 27:215-219, 1999). Each residue must be separated by a – (minus), x represents any amino acid, [DE] means either D or E, {FWY} means any amino acid except for F, W, and Y, A(2,3) means that A appears 2 to 3 times consecutively, the pattern string must be terminated with a . (period). For example, a motif that defines the OleA protein cluster would be entered at [LF]-X-X-[IVLM]-[ATSV]-G-[IV]-X-[EAHS]-R-R-X-W. The user selects "search sequence databases for a given pattern" they then enter the above pattern in the pattern box and select the database to be searched.

TABLE 9

| SEQ ID | MOTIF * |
|---|---|
| SEQ ID NO: 23 | $[L/E]_1-X_2-X_3-[I/V/L/M]_4-[A/T/S/V]_5-G_6-[I/V]_7-X_8-[E/A/H/S]_9-R_{10}-R_{11}-X_{12}-W_{13}$ |

TABLE 9-continued

| SEQ ID | MOTIF * |
|---|---|
| SEQ ID NO: 24 | $[T/A/C]_1-[S/G/T]_2-V_3-X_4-[R/Q]_5-X_6-X_7-X_8-E_9-P_{10}-[S/A]_{11}-[T/V]_{12}-A_{13}$ |
| SEQ ID NO: 25 | $[D]_1-[V/I/L]_2-X_3-[N]_4-[A]_5-[C]_6-[L]_7-[A/G]_8$ |
| SEQ ID NO: 26 | $[L/M]_1-[T]_2-X_3-[G]_4-[S/C/A]_5-[G]_6$ |
| SEQ ID NO: 27 | $[M]_1-X_2-[T]_3-[D/S/N]_4-X_5-X_6-X_7-X_8-X_9-X_{10}-X_{11}-[G]_{12}$ |
| SEQ ID NO: 28 | $[L/F]_1-X_2-X_3-[G]_4-[D/E]_5-X_6-X_7-X_8-X_9-[L/M]_{10}-[G]_{11}-[I/V/M]_{12}-[G]_{13}-[S]_{14}-[G]_{15}-[L/I]_{16}-[N]_{17}-[C/A/T/S]_{18}-X_{19}-[M/A/V]_{20}-X_{21}-X_{22}-X_{23}-X_{24}-[W]_{25}$ |

* Each residue must be separated by – (minus), x represents any amino acid.

[D/E] means either D or E. subscript numbering indicates the position of the aminot acid within the motif.

Similarly, the motifs provided in Table 10 can be used to identify additional OleD enzymes having hydrocarbon synthase activity. These motifs can also be used to identify OleD enzymes having dehydrogenase activity.

TABLE 10

| SEQ ID | MOTIF * |
|---|---|
| SEQ ID NO: 43 | [ILVA]-[LFV]-V-T-G-[GAC]-[GSN]-G-[FLM]-[LV]-G-X-X-[LVIT]-[CVA]-X-X-L-X-X-X-G |

TABLE 10-continued

| SEQ ID | MOTIF * |
|---|---|
| SEQ ID NO: 44 | H-[NVTL]-[AG]-[AS]-[KLVIQR]-[VAPI]-[GSD]-[AVLIM]-X-G |

* Each residue must be separated by - (minus), x represents any amino acid.
[D/E] means either D or E. subscript numbering indicates the position of the aminot acid within the motif.

Similarly, the motifs provided in Table 11 can be used to identify additional OleC enzymes having hydrocarbon synthase activity.

TABLE 11

| SEQ ID | MOTIF * |
|---|---|
| SEQ ID NO: 45 | G-X-X-[DE]-[lm]-[pacs]-[tag]-f-p-[lp]-f-[asg]-l-f-x-x-a-[lm]-g. |
| SEQ ID NO: 46 | H-R-M-G-D-[VL]-[GA]-X-X-D-X(5)-W-[FM]-[CY]-G-R-K-X-[HQ]-[RI]-V. |
| SEQ ID NO: 47 | L-X-H-X-X-F-P-[VM]-D-[IV]-R-H-N-[AS]-K-I-[GF]-R-E-X-L-A-X-W-A. |

* Each residue must be separated by - (minus), x represents any amino acid.
[D/E] means either D or E. subscript numbering indicates the position of the aminot acid within the motif.

Example 6

Enhancing Production of Olefins Via Host Modifications

This example demonstrates that expression of ORF 1, 2 and 3 (OleA (SEQ ID NO: 2), OleC (SEQ ID NO: 6), and OleD (SEQ ID NO: 8), respectively) in combination with alterations in the fatty acid biosynthetic machinery in *E. coli* results in enhanced production of olefin. OleA, OleC and OleD were expressed in the *E. coli* hosts which combined the over expression of 'tesA and fadD and deletion of fadE, and the resulting recombinant bacteria were cultured, induced, pelleted, and extracted as described above. The resulting olefins detected by GC/MS were: 1) saturated; 2) mono unsaturated; and 3) di unsaturated. The olefins ranged in carbon chain length from $C_{27}$ to $C_{31}$.

Figure 6:
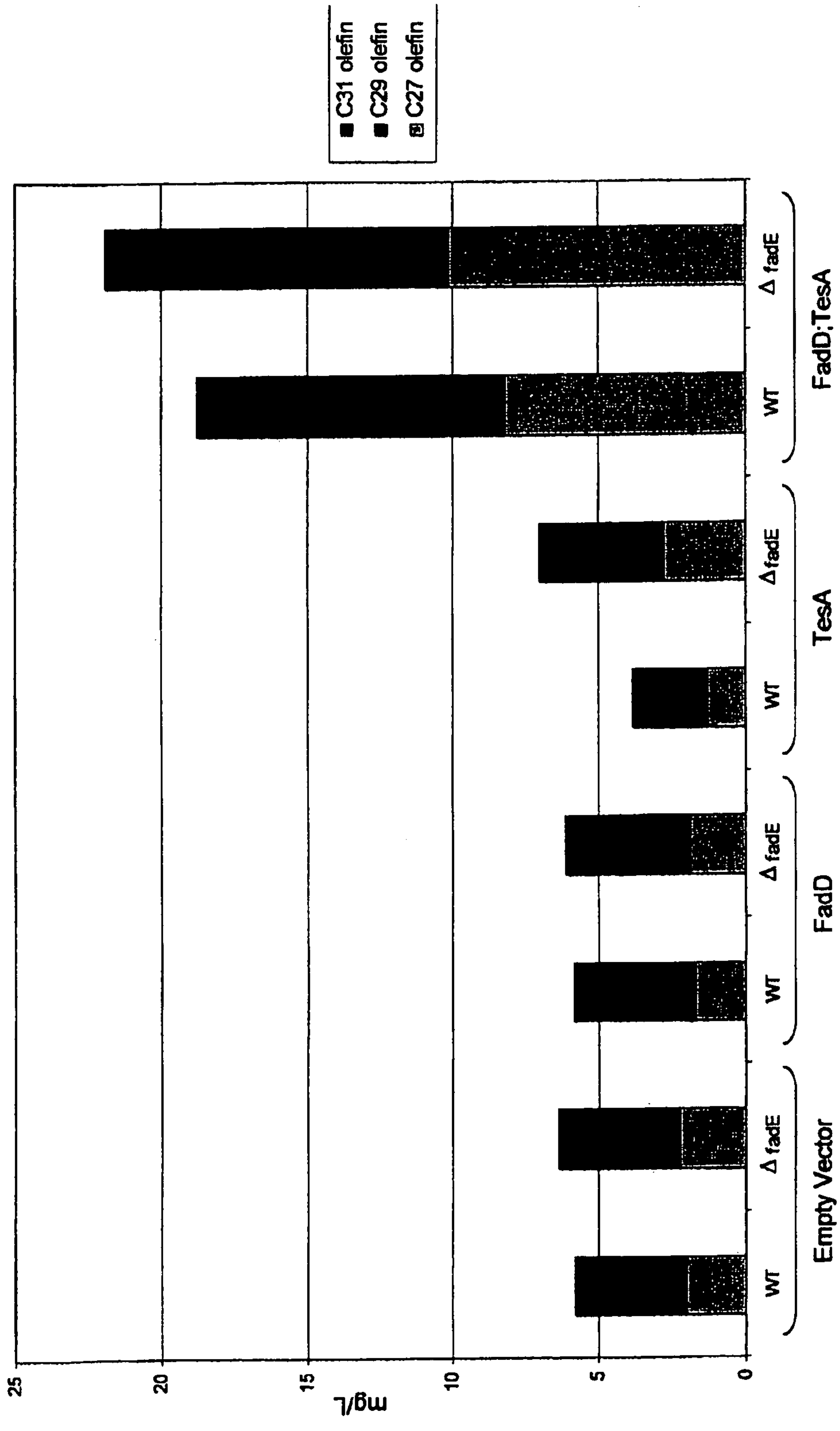
FIG. 6 shows an increase in olefin production resulted due to the expression of OleA, OleC and OleD in the *E. coli* strains which combines the over expression of 'tesA and fadD and deletion of fadE.

FIG. 6 shows an increase in olefin production resulted due to the expression of OleA, OleC and OleD in the *E. coli* strains which combined the over expression of 'tesA and fadD and deletion of fadE. These modifications achieved a 4 fold increase in olefin production.

Example 7

Recombinant Microorganism Construction

The genes that control the fatty acid biosynthetic pathway product production are conserved between microorganisms. For example, Table 12 identifies the homologs of many of the genes described herein which are known to be expressed in microorganisms that produce biocrude, such as hydrocarbons. To increase fatty acid biosynthetic pathway product production and, therefore, biocrude production in microorganisms such as those identified in Table 10, heterologous genes can be expressed. One of ordinary skill in the art will appreciate that genes that are endogenous to the micoorganisms provided in Table 10 can also be over expressed, or attenuated using the methods described herein. Moreover, genes that are described in FIG. 7 can be expressed or attenuated in microorganisms that endogenously produce fatty acid biosynthetic pathway products to allow for the production of specific fatty acid biosynthetic pathway products with defined carbon chain length, saturation points, and branch points.

For example, exogenous nucleic acid sequences encoding acetyl-CoA carboxylase are introduced into *K. radiotolerans*. The following genes comprise the acetyl-CoA carboxylase protein product in *K. radiotolerans*; acetyl CoA carboxylase, alpha subunit (accA/ZP_00618306), acetyl-CoA carboxylase, biotin carboxyl carrier protein (accB/ZP_00618387), acetyl-CoA carboxylase, biotin carboxylase subunit (accC/ZP_00618040), and acetyl-CoA carboxylase, beta (carboxyltranferase) subunit (accD/ZP_00618306). These genes are cloned into a plasmid such that they make a synthetic acetyl-CoA carboxylase operon (accABCD) under the control of a *K. radiotolerans* expression system such as the expression system disclosed in Ruyter et al., *Appl Environ Microbiol.* 62:3662-3667, 1996. Transformation of the plasmid into *K. radiotolerans* will enhance fatty acid production. The hydrocarbon producing strain of *K. radiotolerans* can also be engineered to make branched, unsaturated hydrocarbons having specific carbon chain lengths using the methods disclosed herein.

TABLE 12

| Hydrocarbon recombinant microorganisms | | | |
|---|---|---|---|
| Organism | Gene Name | Accession No./Seq ID/Loci | EC No. |
| *Desulfovibrio desulfuricans* G20 | accA | YP_388034 | 6.4.1.2 |
| *Desulfovibrio desulfuricans* G22 | accC | YP_388573/YP_388033 | 6.3.4.14, 6,4.1.2 |
| *Desulfovibrio desulfuricans* G23 | accD | YP_388034 | 6.4.1.2 |
| *Desulfovibrio desulfuricans* G28 | fabH | YP_388920 | 2.3.1.180 |
| *Desulfovibrio desulfuricans* G29 | fabD | YP_388786 | 2.3.1.39 |
| *Desulfovibrio desulfuricans* G30 | fabG | YP_388921 | 1.1.1.100 |
| *Desulfovibrio desulfuricans* G31 | acpP | YP_388922/YP_389150 | 3.1.26.3, 1.6.5.3, 1.6.99.3 |
| *Desulfovibrio desulfuricans* G32 | fabF | YP_388923 | 2.3.1.179 |
| *Desulfovibrio desulfuricans* G33 | gpsA | YP_389667 | 1.1.1.94 |
| *Desulfovibrio desulfuricans* G34 | ldhA | YP_388173/YP_390177 | 1.1.1.27, 1.1.1.28 |
| *Erwinia* (*micrococcus*) *amylovora* | accA | 942060-943016 | 6.4.1.2 |
| *Erwinia* (*micrococcus*) *amylovora* | accB | 3440869-3441336 | 6.4.1.2 |
| *Erwinia* (*micrococcus*) *amylovora* | accC | 3441351-3442697 | 6.3.4.14, 6.4.1.2 |
| *Erwinia* (*micrococcus*) *amylovora* | accD | 2517571-2516696 | 6.4.1.2 |
| *Erwinia* (*micrococcus*) *amylovora* | fadE | 1003232-1000791 | 1.3.99.— |

TABLE 12-continued

| Hydrocarbon recombinant microorganisms | | | |
|---|---|---|---|
| Organism | Gene Name | Accession No./Seq ID/Loci | EC No. |
| *Erwinia (micrococcus) amylovora* | plsB(D311E) | 333843-331423 | 2.3.1.15 |
| *Erwinia (micrococcus) amylovora* | aceE | 840558-843218 | 1.2.4.1 |
| *Erwinia (micrococcus) amylovora* | aceF | 843248-844828 | 2.3.1.12 |
| *Erwinia (micrococcus) amylovora* | fabH | 1579839-1580789 | 2.3.1.180 |
| *Erwinia (micrococcus) amylovora* | fabD | 1580826-1581749 | 2.3.1.39 |
| *Erwinia (micrococcus) amylovora* | fabG | CAA74944 | 1.1.1.100 |
| *Erwinia (micrococcus) amylovora* | acpP | 1582658-1582891 | 3.1.26.3, 1.6.5.3, 1.6.99.3 |
| *Erwinia (micrococcus) amylovora* | fabF | 1582983-1584221 | 2.3.1.179 |
| *Erwinia (micrococcus) amylovora* | gpsA | 124800-125810 | 1.1.1.94 |
| *Erwinia (micrococcus) amylovora* | ldhA | 1956806-1957789 | 1.1.1.27, 1.1.1.28 |
| *Kineococcus radiotolerans* SRS30216 | accA | ZP_00618306 | 6.4.1.2 |
| *Kineococcus radiotolerans* SRS30216 | accB | ZP_00618387 | 6.4.1.2 |
| *Kineococcus radiotolerans* SRS30216 | accC | ZP_00618040/ ZP_00618387 | 6.3.4.14, 6.4.1.2 |
| *Kineococcus radiotolerans* SRS30216 | accD | ZP_00618306 | 6.4.1.2 |
| *Kineococcus radiotolerans* SRS30216 | fadE | ZP_00617773 | 1.3.99.— |
| *Kineococcus radiotolerans* SRS30216 | plsB(D311E) | ZP_00617279 | 2.3.1.15 |
| *Kineococcus radiotolerans* SRS30216 | aceE | ZP_00617600 | 1.2.4.1 |
| *Kineococcus radiotolerans* SRS30216 | aceF | ZP_00619307 | 2.3.1.12 |
| *Kineococcus radiotolerans* SRS30216 | fabH | ZP_00618003 | 2.3.1.180 |
| *Kineococcus radiotolerans* SRS30216 | fabD | ZP_00617602 | 2.3.1.39 |
| *Kineococcus radiotolerans* SRS30216 | fabG | ZP_00615651 | 1.1.1.100 |
| *Kineococcus radiotolerans* SRS30216 | acpP | ZP_00617604 | 3.1.26.3, 1.6.5.3, 1.6.99.3 |
| *Kineococcus radiotolerans* SRS30216 | fabF | ZP_00617605 | 2.3.1.179 |
| *Kineococcus radiotolerans* SRS30216 | gpsA | ZP_00618825 | 1.1.1.94 |
| *Kineococcus radiotolerans* SRS30216 | ldhA | ZP_00618879 | 1.1.1.27, 1.1.1.28 |
| *Rhodospirillum rubrum* | accA | YP_425310 | 6.4.1.2 |
| *Rhodospirillum rubrum* | accB | YP_427521 | 6.4.1.2 |
| *Rhodospirillum rubrum* | accC | YP_427522/YP_425144/YP_427028/ YP_426209/ YP_427404 | 6.3.4.14, 6.4.1.2 |
| *Rhodospirillum rubrum* | accD | YP_428511 | 6.4.1.2 |
| *Rhodospirillum rubrum* | fadE | YP_427035 | 1.3.99.— |
| *Rhodospirillum rubrum* | aceE | YP_427492 | 1.2.4.1 |
| *Rhodospirillum rubrum* | aceF | YP_426966 | 2.3.1.12 |
| *Rhodospirillum rubrum* | fabH | YP_426754 | 2.3.1.180 |
| *Rhodospirillum rubrum* | fabD | YP_425507 | 2.3.1.39 |
| *Rhodospirillum rubrum* | fabG | YP_425508/YP_425365 | 1.1.1.100 |
| *Rhodospirillum rubrum* | acpP | YP_425509 | 3.1.26.3, 1.6.5.3, 1.6.99.3 |
| *Rhodospirillum rubrum* | fabF | YP_425510/YP_425510/ YP_425285 | 2.3.1.179 |
| *Rhodospirillum rubrum* | gpsA | YP_428652 | 1.1.1.94 |
| *Rhodospirillum rubrum* | ldhA | YP_426902/YP_428871 | 1.1.1.27, 1.1.1.28 |
| *Vibrio furnissii* | accA | 1, 16 | 6.4.1.2 |
| *Vibrio furnissii* | accB | 2, 17 | 6.4.1.2 |
| *Vibrio furnissii* | accC | 3, 18 | 6.3.4.14, 6.4.1.2 |
| *Vibrio furnissii* | accD | 4, 19 | 6.4.1.2 |
| *Vibrio furnissii* | fadE | 5, 20 | 1.3.99.— |
| *Vibrio furnissii* | plsB(D311E) | 6, 21 | 2.3.1.15 |
| *Vibrio furnissii* | aceE | 7, 22 | 1.2.4.1 |
| *Vibrio furnissii* | aceF | 8, 23 | 2.3.1.12 |
| *Vibrio furnissii* | fabH | 9, 24 | 2.3.1.180 |
| *Vibrio furnissii* | fabD | 10, 25 | 2.3.1.39 |
| *Vibrio furnissii* | fabG | 11, 26 | 1.1.1.100 |
| *Vibrio furnissii* | acpP | 12, 27 | 3.1.26.3, 1.6.5.3, 1.6.99.3 |
| *Vibrio furnissii* | fabF | 13, 28 | 2.3.1.179 |
| *Vibrio furnissii* | gpsA | 14, 29 | 1.1.1.94 |

TABLE 12-continued

| Hydrocarbon recombinant microorganisms | | | |
|---|---|---|---|
| Organism | Gene Name | Accession No./Seq ID/Loci | EC No. |
| *Vibrio furnissii* | ldhA | 15, 30 | 1.1.1.27, 1.1.1.28 |
| *Stenotrophomonas maltophilia* R551-3 | accA | ZP_01643799 | 6.4.1.2 |
| *Stenotrophomonas maltophilia* R551-3 | accB | ZP_01644036 | 6.4.1.2 |
| *Stenotrophomonas maltophilia* R551-3 | accC | ZP_01644037 | 6.3.4.14, 6.4.1.2 |
| *Stenotrophomonas maltophilia* R551-3 | accD | ZP_01644801 | 6.4.1.2 |
| *Stenotrophomonas maltophilia* R551-3 | fadE | ZP_01645823 | 1.3.99.— |
| *Stenotrophomonas maltophilia* R551-3 | plsB(D311E) | ZP_01644152 | 2.3.1.15 |
| *Stenotrophomonas maltophilia* R551-3 | aceE | ZP_01644724 | 1.2.4.1 |
| *Stenotrophomonas maltophilia* R551-3 | aceF | ZP_01645795 | 2.3.1.12 |
| *Stenotrophomonas maltophilia* R551-3 | fabH | ZP_01643247 | 2.3.1.180 |
| *Stenotrophomonas maltophilia* R551-3 | fabD | ZP_01643535 | 2.3.1.39 |
| *Stenotrophomonas maltophilia* R551-3 | fabG | ZP_01643062 | 1.1.1.100 |
| *Stenotrophomonas maltophilia* R551-3 | acpP | ZP_01643063 | 3.1.26.3, 1.6.5.3, 1.6.99.3 |
| *Stenotrophomonas maltophilia* R551-3 | fabF | ZP_01643064 | 2.3.1.179 |
| *Stenotrophomonas maltophilia* R551-3 | gpsA | ZP_01643216 | 1.1.1.94 |
| *Stenotrophomonas maltophilia* R551-3 | ldhA | ZP_01645395 | 1.1.1.27, 1.1.1.28 |
| *Synechocystis* sp. PCC6803 | accA | NP_442942 | 6.4.1.2 |
| *Synechocystis* sp. PCC6803 | accB | NP_442182 | 6.4.1.2 |
| *Synechocystis* sp. PCC6803 | accC | NP_442228 | 6.3.4.14, 6.4.1.2 |
| *Synechocystis* sp. PCC6803 | accD | NP_442022 | 6.4.1.2 |
| *Synechocystis* sp. PCC6803 | fabD | NP_440589 | 2.3.1.39 |
| *Synechocystis* sp. PCC6803 | fabH | NP_441338 | 2.3.1.180 |
| *Synechocystis* sp. PCC6803 | fabF | NP_440631 | 2.3.1.179 |
| *Synechocystis* sp. PCC6803 | fabG | NP_440934 | 1.1.1.100, 3.1.26.3 |
| *Synechocystis* sp. PCC6803 | fabZ | NP_441227 | 4.2.1.60 |
| *Synechocystis* sp. PCC6803 | fabI | NP_440356 | 1.3.1.9 |
| *Synechocystis* sp. PCC6803 | acp | NP_440632 | |
| *Synechocystis* sp. PCC6803 | fadD | NP_440344 | 6.2.1.3 |
| *Synechococcus elongatus* PCC7942 | accA | YP_400612 | 6.4.1.2 |
| *Synechococcus elongatus* PCC7942 | accB | YP_401581 | 6.4.1.2 |
| *Synechococcus elongatus* PCC7942 | accC | YP_400396 | 6.3.4.14, 6.4.1.2 |
| *Synechococcus elongatus* PCC7942 | accD | YP_400973 | 6.4.1.2 |
| *Synechococcus elongatus* PCC7942 | fabD | YP_400473 | 2.3.1.39 |
| *Synechococcus elongatus* PCC7942 | fabH | YP_400472 | 2.3.1.180 |
| *Synechococcus elongatus* PCC7942 | fabF | YP_399556 | 2.3.1.179 |
| *Synechococcus elongatus* PCC7942 | fabG | YP_399703 | 1.1.1.100, 3.1.26.3 |
| *Synechococcus elongatus* PCC7942 | fabZ | YP_399947 | 4.2.1.60 |
| *Synechococcus elongatus* PCC7942 | fabI | YP_399145 | 1.3.1.9 |
| *Synechococcus elongatus* PCC7942 | acp | YP_399555 | |
| *Synechococcus elongatus* PCC7942 | fadD | YP_399935 | 6.2.1.3 |

For Table 10, Accession Numbers are from GenBank, Release 159.0 as of Apr. 15, 2007, EC Numbers are from KEGG, Release 42.0 as of April 2007 (plus daily updates up to and including May 9, 2007), results for Erwinia amylovora strain Ea273 are taken from the Sanger sequencing center, completed shotgun sequence as of May 9, 2007, positions for Erwinia represent locations on the Sanger psuedo-chromosome sequences from Vibrio furnisii M1 are from the LS9 VFM1 pseudochromosome, v2 build, as of Sep. 28, 2006, and include the entire gene, and may also include flanking sequence

Example 8

Production of Biocrude for Cracking

This example describes the production of biocrude using a recombinant microorganism. One of ordinary skill in the art will appreciate that there are many alternative recombinant microorganisms that can be used to produce biocrude, such as those described throughout the specification, including in the Examples section.

The general methods described in Example 1 above were used in the production of biocrude and the detection of hydrocarbon products.

Briefly, PCR primers LB118 (SEQ ID NO: 29) and LB152 (SEQ ID NO: 36) were used to amplify the sequence containing the combination of OleA OleB (SEQ ID NO: 47). PCR primers LB155 (SEQ ID NO: 31) and LB158 (SEQ ID NO: 34) were used to amplify the OleC/OleD combination, which is shown in SEQ ID NO: 48 from genomic DNA isolated from *Stenotrophomonas maltophilia*. PCR products and vectors (pETDuet and pCOLADuet) were digested with NdeI and XhoI. The digested PCR products and vectors were gel purified and combined in a ligation reaction. The ligations were then transformed into *E. coli* C41(DE3). After confirmation of plasmid constructs, the purified constructs were transformed together into a single strain. The result was the creation of the recombinant microorganism identified as *E. coli* C41(DE3) AfadE with pETDuet-OleA OleB (SEQ ID NO: 48) and pCOLADuet-OleC OleD (SEQ ID NO: 49). This strain was used to produce olefins.

High density fermentations of the *E. coli* C41(DE3) ΔfadE with pETDuet-OleA OleB and pCOLADuet-OleC OleD strain were carried out to obtain sufficient biocrudc samples for subsequent use in catalytic cracking experiments. Bioreactor fermentations were carried out in a 2 liter stirred bioreactor (Sartorius A B, Aplus series, Weender Landstrasse 94-108 D-37075 Goettingen, Germany) with an initial volume of 1 L F1 media (0.5% w/v glucose) as described by Pfeifer et al. (Pfeifer et al. Appl Environ Microbiol. 68: 3287-3292, 2002). Briefly, 100 mg of carbenicilin and 100 mg of kanomycin were added to the bioreactor. The pH was maintained at 7.2 with 1 M $H_2SO_4$ and 5 M $NH_4OH$ and the temperature was maintained at 37° C. Dissolved oxygen was maintained at 30% by adjusting the agitation speed. Air flow was maintained at 2.0 Lpm. The bioreactor was inoculated with 100 mL of culture grown to stationary phase at 37° C. in F1 media. Upon exhaustion of glucose, an F1 feed stream (43% w/v glucose) was started and maintained at 0.2 mL per minute. Once the $OD_{600}$ reached 30, the fermentation was induced with 1 mM IPTG. The fermentation when ended after 96 hours when the cells were harvested for extraction.

The fermentation broth was spun at 4000×g for 30 minutes to pellet out the cells. The cells were then resuspended in 400 mL of a 50% methanol/water mixture. The cells were sonicated in a sonicating water bath for 30 minutes at 50° C. Next, 2 L of hexane was added to the cell mixture and agitated vigorously to obtain good liquid-liquid contact. The organic water solution was spun down at 4000×g for 30 minutes and the hexane phase was siphoned off. The organic layer was distilled to remove the hexane. The remaining residue was resuspended in 10 mL of hexane and loaded onto a silica column where flash chromatography was carried out. The biocrude was eluted from the column with 500 mL of hexane. This solution was distilled again to remove the hexane solvent. The remaining biocrude was 99% pure based on GC/MS analysis, and no residual hexane was detected. The resulting hydrocarbons detected by GC/MS were: 1) saturated; 2) mono unsaturated; and 3) di unsaturated. The hydrocarbons ranged in carbon chain length from $C_{27}$ to $C_{31}$.

Example 9

Cracking of Biocrude

Biocrude samples produced according to Example 8 were processed by a micro-catalytic cracking technique using the "Quatra-C" device as described in Benson et al., *J. Chromatography*, A, 1172:204-08, 2007. This device allows a quick determination of the reactivity and selectivity of substrates for probe reactions over certain catalysts.

Figure 8:
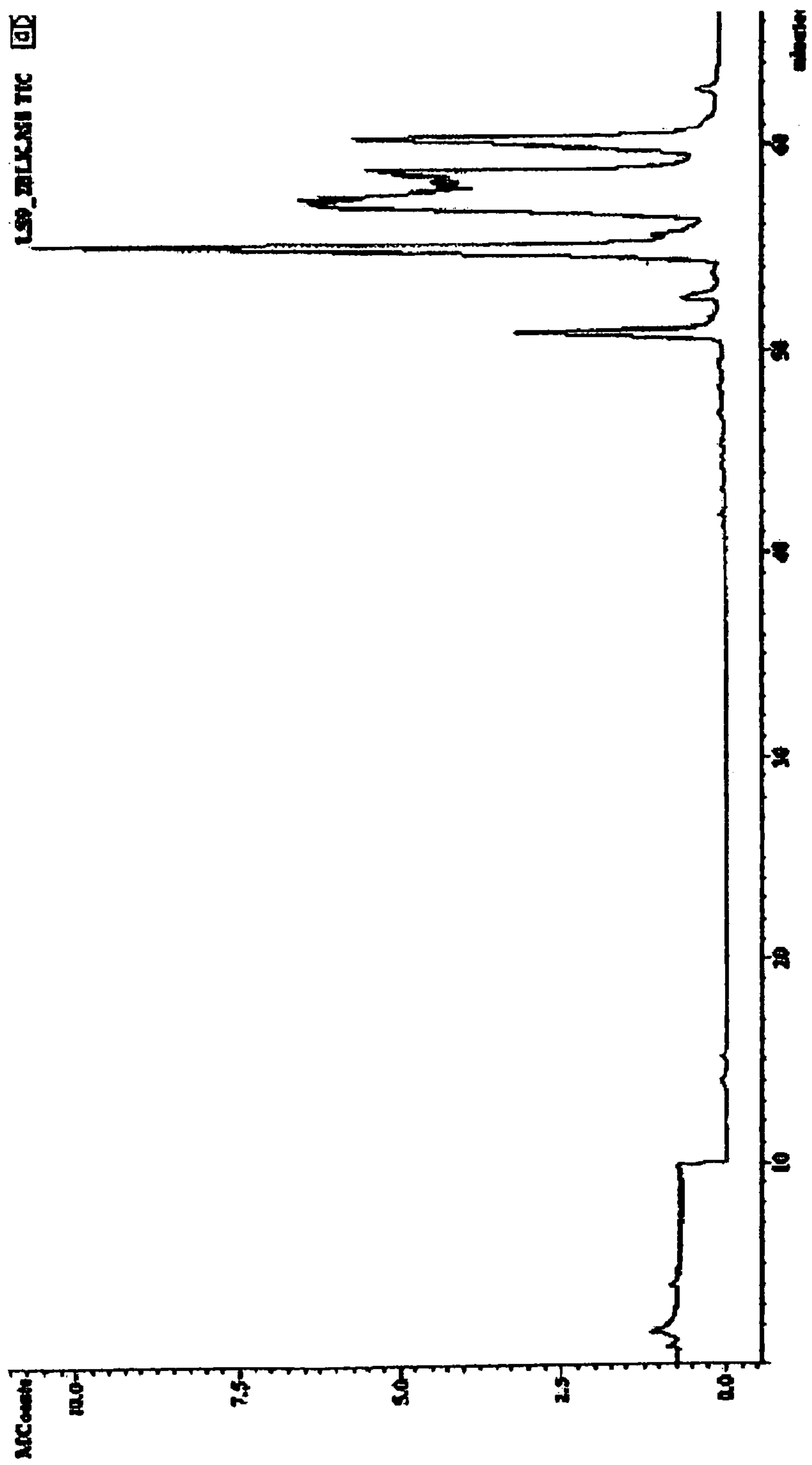
FIG. 8 is a GC/MS for a biocrude sample that does not include any cracking catalyst and was not subjected to cracking.

A heterogeneous catalyst, $H^+$ZSM-5 ($SiO_2/Al_2O_3$=23 mol/mol), obtained from Zeolyst International (Valley Forge, Pa., USA), was used to crack the biocrude and thereby characterize this substance for its ability to be cracked by solid acid catalysts. The catalyst was received in the ammonium form and then calcined at 550° C. for 12 hours in air using a muffle furnace to produce the acidic form. The $H^+$ZSM-5 catalyst used in this study had a particle diameter of ~1 μm, surface area of 425 $m^2$/g, and pore diameter of 5.5 Å. The experiments were carried out using 20 mg catalyst at 400° C. and a carrier gas stream showing a flow rate of 20 mL/min helium. The ID of the tube holding the catalyst=3.9 mm, giving a flow velocity of 168 cm/min. Into this carrier gas, 1 mg of the biocrude was introduced as a means to contact the hydrocarbons with the solid catalysts. For each biocrude sample, a blank run was completed by injecting the biocrude sample into the instrument without any catalyst present. This injection will confirm the non-catalytic activity so that the conversion/selectivity of the catalytic runs can be assigned to the catalyst. The blank run (i.e., no catalyst present) for the biocrude sample is shown in FIG. 8. The peaks eluting between 50-60 minutes is the hydrocarbon and the small peaks eluting at earlier retention times could be impurities or some thermally-induced products. The break in the baseline at 10 minutes reflects the change in the mass spectrometer scan range. The scan is for m/e between 10-80 for time less than 10 minutes and for the remainder of the spectrum the m/e= is between 50-200. The detector response is different in these two regions. The detector response is more sensitive in the first 10 minutes. In this way, the mass spectrometer interrogation can be customized for the likely products eluting during these two time periods.

Figure 9:
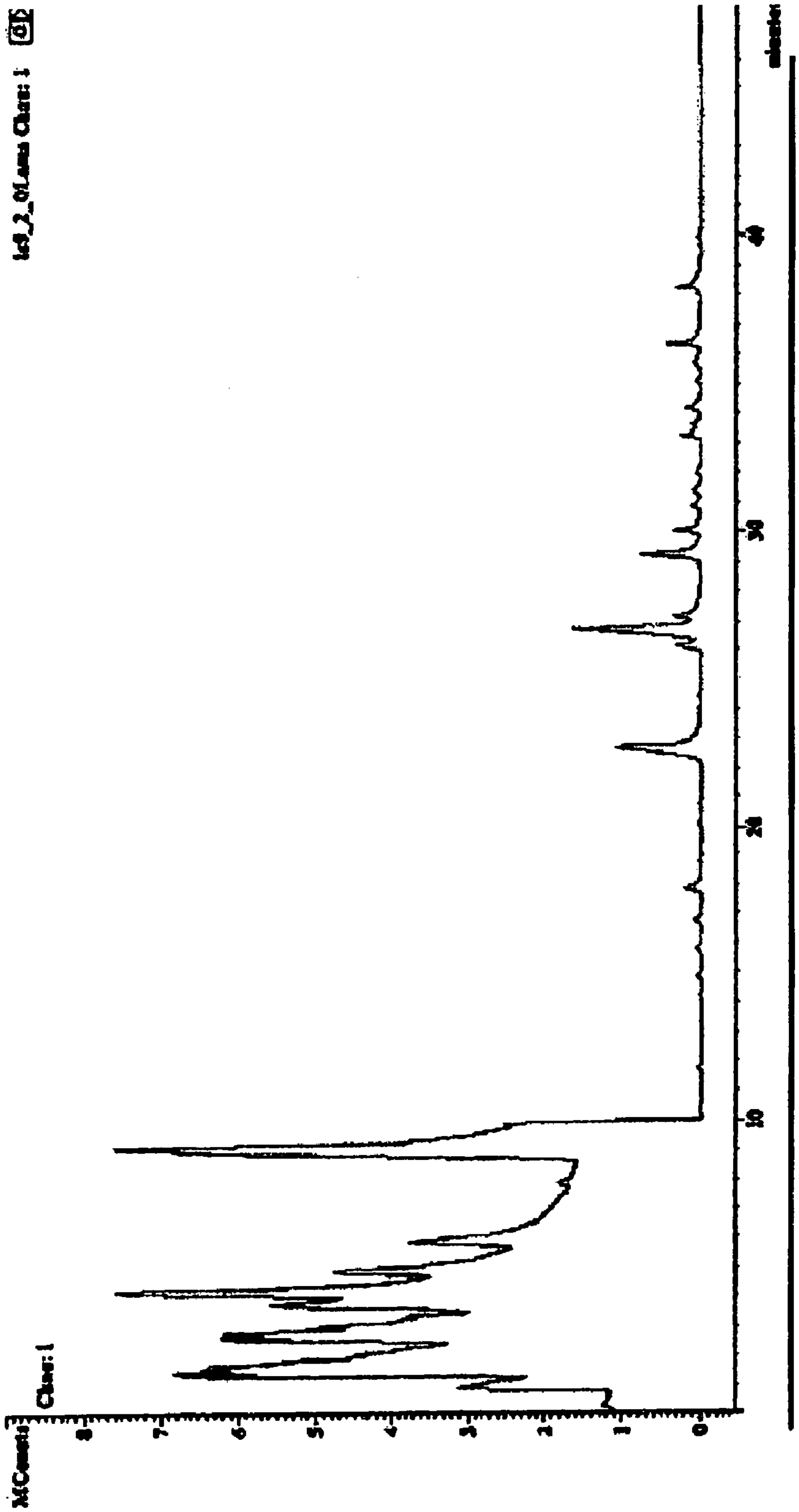
FIG. 9 is a GC/MS for conversion of a biocrude sample using a H+ZSM-5 cracking catalyst.
Figure 10:
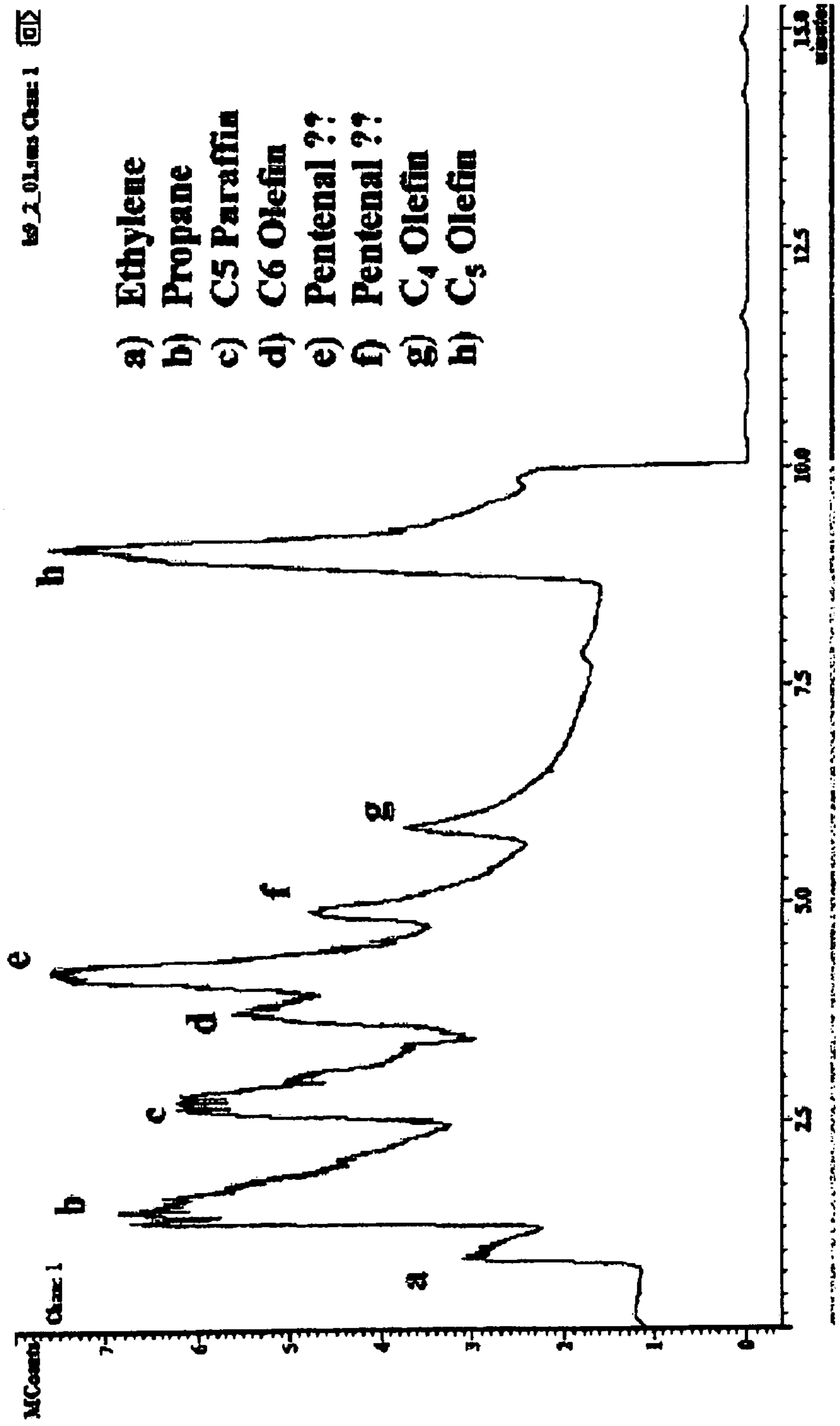
FIG. 10 is a GC/MS showing a low molecular product distribution for a cracked product.

The same biocrude sample was then introduced over the acid catalyst (FIG. 9) to reveal a number of products arising from the cracking of the biocrude sample. The unconverted biocrude elutes after 50 minutes. The lower-molecular weight products of the cracking elute at retention times shorter than 50 minutes. The relative sizes of the peaks suggests that significant conversion of the biocrude is represented by this spectrum. Some of the peaks in this spectrum have been identified as a collection of olefins (FIG. 10). The lightest products are ethylene, isomers of butane and pentane, along with isomers of pentenes, hexenes and heptenes. These are the expected results for cracking a hydrocarbon or hydrocarbon mixture over this catalyst under these conditions.

Figure 11:
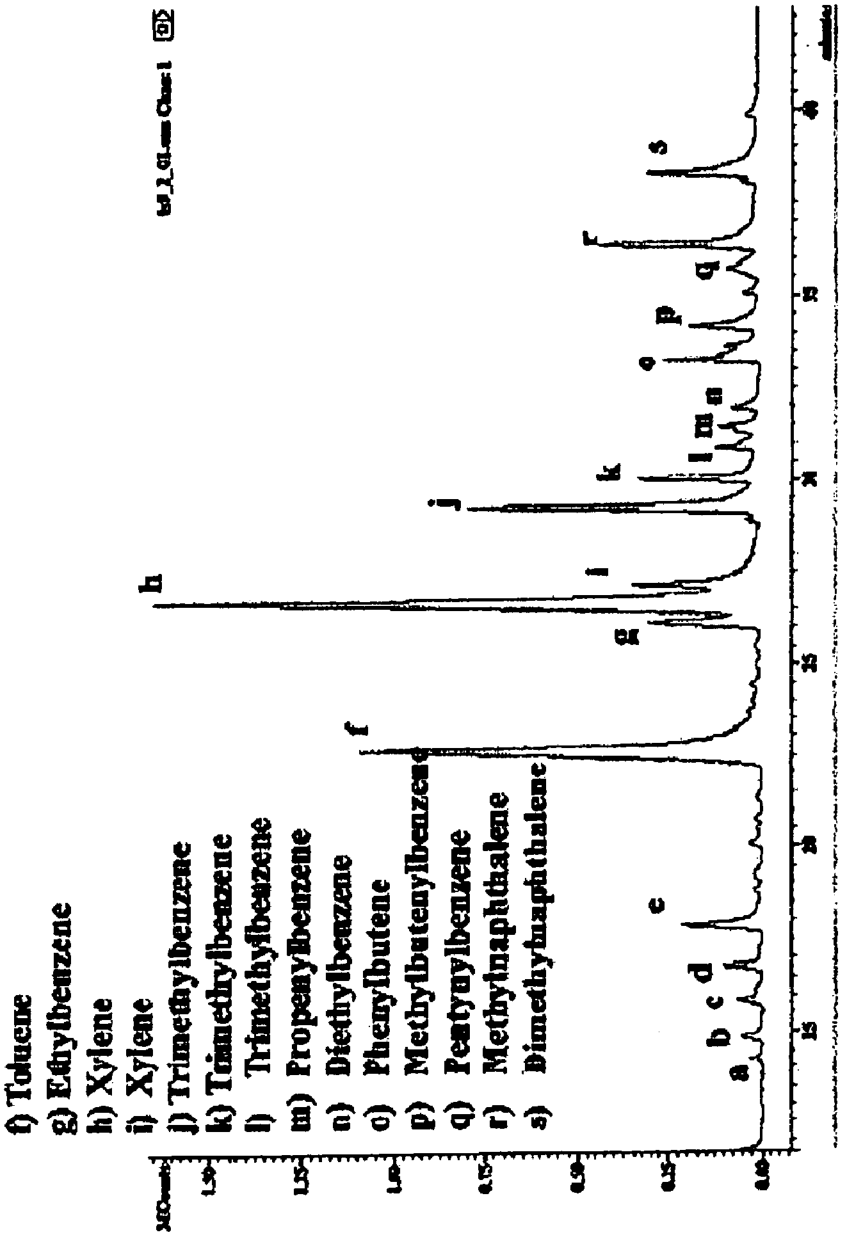
FIG. 11 is a GC/MS showing a high molecular weight product distribution for a cracked product.

A detailed spectrum of the heavier products from the same injection is shown in FIG. 11. Some of these products have been identified as toluene, ethylbenzene, the isomers of xylene and trimethylbenzene. Other aromatics appearing in this spectrum may be C4- and C5-substituted benzenes and substituted naphthalenes. These products are expected to arise from the action of the $H^+$ZSM-5 catalyst to oligomerize lower molecular weight olefins, such as propylene.

Additional experiments were conducted to determine which cracked products from the biocrude sample constituted the gasoline and diesel fractions. In order to make this determination, a gasoline standard (Modified DRO Mix, Supelco) and a diesel standard (GRO Mix, Supelco) were introduced over the acid catalyst. The gasoline standard eluted between 13-19 minutes. The diesel fraction eluted between 20-43 minutes. Using the experimental results from the gasoline and diesel standards, it was concluded that cracked products from the biocrude sample that eluted between 13-19 minutes were suitable for use as gasoline and cracked products from the biocrude sample that eluted between 20-43 minutes were suitable for use as diesel. The relative weight percent of the gasoline and diesel fractions from catalytically cracking the biocrude sample at 300° C. and 350° C. is shown in Table 11.

The GC/MS set-up described above was used to analyze the cracking behavior of the biocrude sample at different temperatures using $H^{+}$ZSM-5, faujasite Y, and amorphous silica-alumina. Different catalyst to biocrude ratios were also tested. The catalyst conditions described above were used here. The percent conversion observed is given in Table 13.

TABLE 13

Biocrude conversion under different cracking conditions

| Catalyst | Temperature ° C. | Catalyst: Biocrude Ratio | % Conversion | Gasoline Fraction (%) | Diesel Fraction (%) |
|---|---|---|---|---|---|
| H + ZSM-5 | 350 | 7 | 100 | | |
| H + ZSM-5 | 350 | 4 | 100 | | |
| faujasite j | 350 | 7 | 96 | | |
| amorphous silica-alumina | 350 | 3.8 | 83 | 40 | 32 |
| amorphous silica-alumina | 300 | 3.8 | 72 | 16 | 20 |

The data in Table 13 demonstrates that the biocrude material cracks efficiently under mild conditions. Complete conversion of the biocrude sample was obtained with H+ZSM-5 and faujasite j (both highly acidic catalysts) at low temperatures. Most refineries operate catalytic crackers at over 500° C. The less acidic and less expensive amorphous silica-alumina yielded desired conversion at 300° C. Complete conversion is undesirable because it typically results in the formation of light gasses and coke. Conversions around 70% are considered optimal (Nate, and V. W. Weekman, *AICHE Journal,* 16, 371, 1970).

The amorphous silica-alumina catalyst at 300° C. with a biocrude to catalyst ratio of 3.8 cracked the biocrude sample into hundreds of different hydrocarbon compounds, as is typically observed with this catalyst. The percentage of hydrocarbons obtained with five or more carbons was 49%. This material is typically used in gasoline and diesel. The other 51% of the cracked material constituted of light gasses (C1-C4 compounds).

Example 10

Cracking Fatty Acid Esters

Microorganisms can be engineered to produce fatty acid esters with exogenous alcohol feeding by implementing the following genetic manipulations. First, if the organism contains a fatty acid degradation pathway, the gene responsible for the first oxidation step can be deleted. For example, in *E. coli* the fadE gene can be deleted. A thioesterase must also be expressed to cleave off growing fatty acid chains from acyl carrier proteins. In *E. coli*, an example of such a thioesterase is tesA. The fatty acid should be re-activated by a coenzyme A ligase to form an acyl-CoA compound by over expressing a gene, such as fadD from *E. coli*. Lastly, an ester synthase can be expressed in the ester producing strain. One example of such a gene is the wax ester synthase/acyl-CoA:diacylglycerol acyltransferase from *Acinetobacter* sp. strain ADP1. Under appropriate expression conditions and with the feeding of appropriate alcohols, such as methanol, ethanol, propanol, etc fatty acid esters can be formed. It is well known in the art that each of these steps need not occur in the same organism. Several organisms can be used for some or all of these in vivo conversions. Moreover, some or all of these steps can be performed in vitro.

The fatty acid esters produced by this method can then be catalytically cracked to produce a cracked product. Previous studies have described catalytic cracking conditions (catalyst, temperature, catalyst to oil ratio, etc.) necessary to convert palm oil into gasoline and other liquid fuels (See, for example, Farouq et al., *Fuel Processing Technology* 85:1283-1300, 2004, which is incorporated herein in its entirety). Palm oil, as well as most vegetable oils, consists of three fatty acids linked to glycerol through three ester linkages. Fatty acid esters, such as fatty acid methyl esters, possess similar chemical functional groups as vegetable oils (e.g., ester linkages and in some cases double bonds in the fatty chain). The chemical similarity between fatty acid esters and vegetable oils implies that the fatty acid esters will form liquid fuels under conditions described to catalytically crack palm oil. An example of such a condition as described in the above reference uses HZSM-5 catalyst at 450° C., with a weight hourly space velocity (WHSV) of 2.5 h−1, an oil-to-catalyst ratio of 7.2. These conditions resulted in a 96.8 wt. % conversion of the palm oil and yielded a gasoline fraction of 46 wt. %.

Having illustrated and described the principles of the disclosure in multiple embodiments and examples, it should be apparent that the disclosure can be modified in arrangement and detail without departing from such principles. The disclosure encompasses all modifications coming within the spirit and scope of the following claims:

What is claimed is:

1. A method for making low molecular weight hydrocarbons from a biocrude, which method comprises:

(a) obtaining a recombinant microorganism comprising one or more polynucleotides encoding one or more polypeptides having acetyl-CoA carboxylase (accABCD) activity (EC 6.4.1.2, 6.3.4.14), wherein the one or more polynucleotides are exogenous to the recombinant microorganism or wherein one or more endogenous polynucleotides encoding one or more polypeptides having accABCD activity are overexpressed in the recombinant microorganism;

(b) culturing the recombinant microorganism in a culture medium containing a carbohydrate as the carbon source under conditions effective to express the one or more polynucleotides, wherein the recombinant microorganism produces a biocrude; and (c) cracking the biocrude resulting in low molecular weight hydrocarbons.

2. The method of claim 1, wherein the recombinant microorganism further comprises one or more polynucleotides encoding a polypeptide having OleABCD activity, thioesterase activity (EC 3.1.2.14 or EC 3.1.1.5), acyl-CoA synthetase (fadD) activity (EC 2.3.1.86), fatty alcohol foaming acyl-CoA reductase (FAR) activity (EC 1.1.1.*), acyl-CoA reductase activity (EC 1.2.1.42) and ester synthase activity (EC 2.3.1.-, 2.3.1.20).

3. The method of claim 2, wherein the biocrude is substantially free of any compounds that include oxygen.

4. The method of claim 2, wherein the biocrude includes greater than about 90 wt % alkene compounds, based on the total weight of the biocrude.

5. The method of claim 2, which method comprises catalytically cracking the biocrude at a temperature of 350° C. or lower.

6. The method of claim 2, wherein the cracking comprises catalytic cracking.

7. The method of claim 2, wherein the cracking does not include hydrocracking or steam cracking.

8. The method of claim 6, wherein the cracking comprises contacting the biocrude with a catalyst selected from zeolite, aluminum hydrosilicate, treated bentonite clay, fuller's earth, bauxite, amorphous silica-alumina and mixtures or combinations thereof.

9. The method of claim 8, wherein the catalyst is an amorphous silica-alumina.

10. The method of claim 2, wherein the cracking is performed at a temperature of 350° C. or lower.

11. The method of claim 2, wherein the cracking is performed at a temperature of 300° C. or lower.

12. The method of claim 2, wherein the cracking converts $C_{19}$ to $C_{31}$ hydrocarbons in the biocrude to $C_1$ to $C_{18}$ hydrocarbons.

13. The method of claim 2, wherein the cracking converts about 65 to about 75 wt. % of hydrocarbons in the biocrude to low molecular weight hydrocarbons.

14. The method of claim 1, wherein the recombinant microorganism further comprises a polynucleotide encoding a polypeptide having ester synthase activity (EC 2.3.1.-, 2.3.1.20), wherein the recombinant microorganism over expresses the ester synthase.

15. The method of claim 2, wherein the cracked product includes a $C_5$ to $C_{10}$ fraction having a boiling point range of about 30 to about 180° C. at 1 atm.

16. The method of claim 2, wherein the cracked product includes a $C_8$ to $C_{14}$ fraction having a boiling point range of about 120 to about 260° C. at 1 atm.

17. The method of claim 2, wherein the cracked product includes a $C_{14}$ to $C_{18}$ fraction having a boiling point range of about 230 to about 320° C. at 1 atm.

18. The method of claim 2, further comprising mixing the biocrude with petroleum crude prior to cracking, and then cracking the resulting biocrude/petroleum crude mixture.

19. The method of claim 2, wherein the biocrude includes at least about 99 wt % alkene compounds, based on the total weight of the biocrude.

20. The method according to claim 2, further comprising separating the hydrocarbons.

21. The method of claim 20, wherein culturing and separating is continuous.

22. The method of claim 20, wherein separating comprises contacting the fermentation media with an organic composition and allowing the hydrocarbon to separate into the organic composition.

23. The method of claim 2, wherein the recombinant microorganism is *E. coli, S. maltophilia, K. radiotolerans, Rhodococcus, Saccharomyces cerevisiae, Aspergillus, Trichoderma, Neurospora, Fusarium* or *Chrysosporium.*

24. The method of claim 6, wherein the biocrude comprises a hydrocarbon feedstock including greater than about 50 wt % $C_{19}$-$C_{31}$ compounds, based on the total weight of the biocrude.

25. The method of claim 24, wherein the hydrocarbon feedstock includes greater than about 80 wt % $C_{19}$-$C_{31}$ compounds.

26. The method for cracking of claim 2, wherein the biocrude comprises a hydrocarbon feedstock including $C_{19}$ to $C_{31}$ hydrocarbons having at least one alkene moiety.

27. The method of claim 26, wherein the hydrocarbon feedstock includes $C_{22}$ to $C_{31}$ hydrocarbons having at least one alkene moiety.

* * * * *